United States Patent
Radjy

(10) Patent No.: US 10,942,162 B2
(45) Date of Patent: Mar. 9, 2021

(54) SENSOR DEVICE AND ANTENNA, AND SYSTEMS AND METHODS FOR OBTAINING AND TRANSMITTING MEASUREMENTS OF SELECTED CHARACTERISTICS OF A CONCRETE MIXTURE

(71) Applicant: QUIPIP, LLC, Pittsburgh, PA (US)

(72) Inventor: Farrokh F. Radjy, Pittsburgh, PA (US)

(73) Assignee: QUIPIP, LLC, Pittsburgh, PA (US)

( * ) Notice: Subject to any disclaimer, the term of this patent is extended or adjusted under 35 U.S.C. 154(b) by 54 days.

(21) Appl. No.: 16/141,432

(22) Filed: Sep. 25, 2018

(65) Prior Publication Data

US 2019/0101523 A1    Apr. 4, 2019

Related U.S. Application Data

(60) Provisional application No. 62/687,276, filed on Jun. 20, 2018, provisional application No. 62/565,318, filed on Sep. 29, 2017.

(51) Int. Cl.

| | |
|---|---|
| *G01N 33/38* | (2006.01) |
| *H01Q 1/22* | (2006.01) |
| *H01Q 7/00* | (2006.01) |
| *H01Q 1/38* | (2006.01) |

(52) U.S. Cl.
CPC ............ *G01N 33/383* (2013.01); *H01Q 1/38* (2013.01); *H01Q 7/00* (2013.01); *H01Q 1/225* (2013.01); *H01Q 1/2291* (2013.01)

(58) Field of Classification Search
CPC ...... G01N 22/00; G01N 22/04; G01N 27/021; G01N 27/048; G01N 33/383; G01R 1/067; G01R 29/08
See application file for complete search history.

(56) References Cited

U.S. PATENT DOCUMENTS

| | | | |
|---|---|---|---|
| 2002/0005725 A1* | 1/2002 | Scott | G01N 22/00 |
| | | | 324/637 |
| 2002/0180417 A1 | 12/2002 | Colby et al. | |
| 2012/0158333 A1 | 6/2012 | Li et al. | |
| 2016/0018383 A1 | 1/2016 | Radjy | |
| 2018/0011076 A1* | 1/2018 | Radjy | G01N 33/383 |
| 2018/0045621 A1* | 2/2018 | Radjy | G01N 1/28 |

OTHER PUBLICATIONS

International Search Report and Written Opinion dated Dec. 27, 2018 from corresponding International Application No. PCT/US2018/052888.

* cited by examiner

*Primary Examiner* — Brandi N Hopkins

(74) *Attorney, Agent, or Firm* — Lucas & Mercanti, LLP

(57) ABSTRACT

A system includes a sensor device having a sensor adapted to generate measurement data relating to a characteristic of a concrete mixture, a transmitter adapted to transmit a first signal based on the measurement data, and a conductive wire forming a coil having a plurality of loops around the sensor device and a wire antenna. The coil is adapted to generate an electric current in response to the first signal. The antenna is adapted to transmit a second signal based on the electric current. The system is embedded in a concrete mixture and a portion of the antenna is exposed above the surface of the concrete mixture. A current is induced in the coil due to electromagnetic induction. A second signal is transmitted via the wire antenna. The second signal is received and transmitted to a processor. The processor may analyze and/or store the signal.

20 Claims, 58 Drawing Sheets

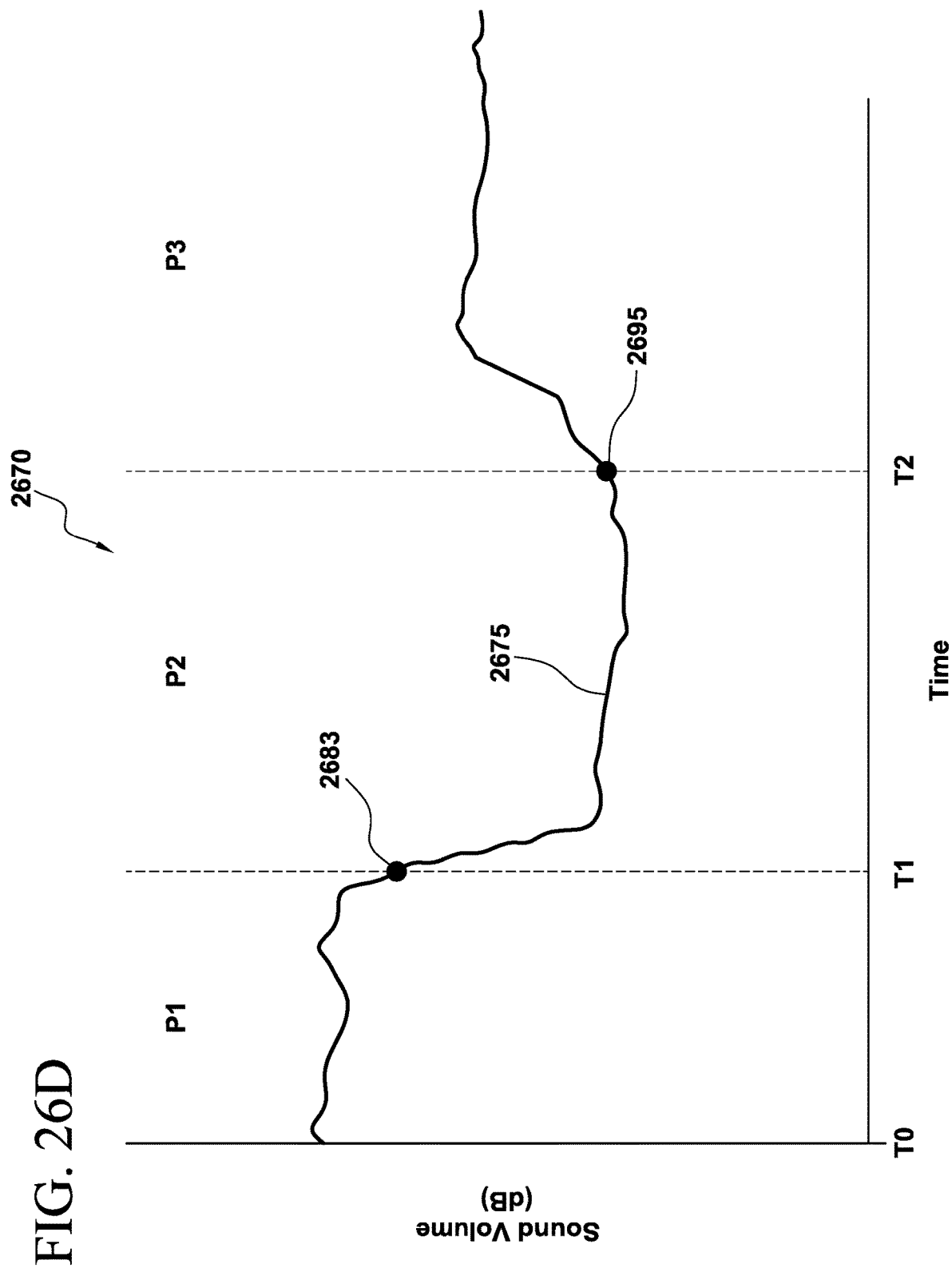

SENSOR DEVICE AND ANTENNA, AND SYSTEMS AND METHODS FOR OBTAINING AND TRANSMITTING MEASUREMENTS OF SELECTED CHARACTERISTICS OF A CONCRETE MIXTURE

CROSS REFERENCE TO RELATED APPLICATION

This application claims priority from U.S. Provisional Application No. 62/565,318 filed Sep. 29, 2017 and from U.S. Provisional Application No. 62/687,276 filed Jun. 20, 2018, the contents of which are incorporated herein by reference.

TECHNICAL FIELD

This specification relates generally to the construction field, and more particularly to a sensor device and antenna, and systems and methods for obtaining and transmitting measurements of selected characteristics of a concrete mixture.

BACKGROUND

Concrete is generally used within the industry to refer to a mixture of cement, sand, stone, and water which upon aging turns into a hardened mass. The term concrete, as used in the specification and claims herein, means not only concrete as it is generally defined in the industry (cement, sand and stone), but it also means mortar (cement, sand and water) and cement (cement and water which hardens into a solid mass upon aging).

In the construction field, after a batch of concrete has been produced for use at a particular site, it is useful to be able to obtain data concerning certain performance characteristics such as the in-place strength of the batch, maturity, and other characteristics. Accurate prediction of concrete performance can increase the quality of the end product, and can provide other benefits such as allowing the use of accelerated construction schedules.

Several methods for testing and monitoring in-place strength of a concrete mass have been incorporated into the American Standard Testing Methods, including ASTM C805 (The Rebound Number Method—the so-called Swiss Hammer Method), ASTM C597 (The Pulse Velocity (Sonic) Method), and ASTM C900 (The Pullout Strength Method).

In accordance with standards set forth in ASTM C31 (Standard Practice for Making and Curing Concrete Test Specimens in the Field), the compressive strength of concrete is measured to ensure that concrete delivered to a project meets the requirements of the job specification and for quality control. In order to test the compressive strength of concrete, cylindrical test specimens are cast in test cylinders and stored in the field until the concrete hardens.

In accordance with the standards, typically 4×8-inch or 6×12-inch test cylinders are used, and the concrete specimens are stored in a carefully selected location for a predetermined period of time. When making cylinders for acceptance of concrete, the field technician must test properties of the fresh concrete including temperature, slump, density (unit weight) and air content.

SUMMARY

In accordance with an embodiment, a sensor device includes a housing, the housing having an opening allowing substances to pass from an exterior of the housing to an interior of the housing, a printed circuit board disposed in the housing, the printed circuit board including a humidity sensor and at least one electronic component, a tube having a first end and a second end, the tube comprising a waterproof material, wherein the first end of the tube surrounds the humidity sensor, wherein a first seal is formed by between the first end of the tube and the printed circuit board, wherein the second end of the tube is located proximate the hole, and a material layer disposed between the second end of the tube and the hole, wherein the material layer comprises a waterproof and breathable material, wherein a second seal is formed between the material layer and the housing, wherein a third seal is formed between the material layer and the second end of the tube. The hole and the material layer allow water vapor to pass from the exterior to the humidity sensor. The first seal, the second seal, and the third seal prevent the water vapor from reaching the at least one electronic component.

In one embodiment, the printed circuit board further comprises one of a temperature sensor, an accelerometer, a pH sensor, an inductance sensor, an impedance or resistivity sensor, a sonic sensor, a pressure sensor, a conductivity sensor, a salinity sensor, a humidity sensor, and an elevation sensor.

In another embodiment, the printed circuit board further includes a transmitter.

In another embodiment, the tube comprises one of plastic and rubber.

In another embodiment, the tube has a diameter of between 0.25 cm and 1.0 cm.

In accordance with another embodiment, a sensor device includes a housing, the housing having an opening that allows water vapor to pass between an exterior of the housing and an interior of the housing but prevents liquid from passing between the exterior and the interior. The sensor device also includes a printed circuit board disposed in the housing, the printed circuit board including a humidity sensor adapted to obtain humidity measurements, one or more second sensors adapted to obtain measurement data, and a processor adapted to: detect a change in the humidity measurements from a first level to a second level, activate the one or more second sensors in response to the change in the humidity measurements, and a transmitter adapted to transmit the humidity measurements and the measurement data.

In one embodiment, the opening comprises a hole in the housing, the hole having a diameter between 0.5 millimeters and 1.0 millimeter.

In another embodiment, the housing comprises a first portion and a second portion, the first and second portions being engaged, and the opening is disposed between the first and second portions.

In another embodiment, the printed circuit board further comprises one of a temperature sensor, an accelerometer, a pH sensor, an inductance sensor, an impedance or resistivity sensor, a sonic sensor, a pressure sensor, a conductivity sensor, a salinity sensor, a humidity sensor, and an elevation sensor.

In accordance with another embodiment, a method is described. The method includes detecting, by a sensing device, a first humidity level representing a humidity of a first environment, embedding the sensing device within a concrete mixture, detecting, by the sensing device, a second humidity level associated with the concrete mixture, determining a change in humidity between the first humidity level and the second humidity level, and activating a selected component of the sensing device in response to detection of the change in humidity.

In one embodiment, the selected component comprises one of a temperature sensor, an accelerometer, a pH sensor, an inductance sensor, an impedance or resistivity sensor, a sonic sensor, a pressure sensor, a conductivity sensor, a salinity sensor, a humidity sensor, and an elevation sensor.

In accordance with another embodiment, a sensor device is provided. The sensor device includes a housing, the housing having a hole allowing substances to pass from an exterior of the housing to an interior of the housing, a printed circuit board disposed in the housing, the printed circuit board including one of a temperature sensor and a humidity sensor, a material layer disposed between the hole and the printed circuit board, wherein the material layer comprises a waterproof and breathable material, and a support element disposed between the printed circuit board and the material layer, the support element adapted to separate the printed circuit board and the material layer. The hole and the material layer allow water vapor to pass from the exterior to the interior of the housing.

In accordance with another embodiment, a sensor device includes a humidity sensor. Before being placed into a concrete mixture, selected components of the sensor device (such as a temperature sensor, a pH sensor, a motion sensor, an accelerometer, etc.) are deactivated. The humidity sensor obtains humidity measurements, and the humidity measurement data is monitored by a processor. At the time when the sensor is inserted into a concrete mixture, the processor detects a change in the humidity measurements. For example, a spike in humidity may be detected. In response to the change in humidity, one or more components of the sensor device are activated. For example, other sensors may be activated in order to obtain measurements of temperature and other characteristics of the concrete mixture.

In accordance with another embodiment, a sensor device includes a sonic sensor adapted to measure sonic signals (sound waves). Before being placed into a concrete mixture, selected components of the sensor device (such as a temperature sensor, a pH sensor, a motion sensor, an accelerometer, etc.) are deactivated. The sonic sensor obtains measurements of sonic signals around the sensor device, and the sonic signal measurement data is monitored by a processor. At the time when the sensor is inserted into a concrete mixture, the processor detects a change in the strength of the sonic signal. For example, after the sensor is inserted into the concrete mixture, a signal loss may be detected as sonic signals (sound waves) are blocked by the concrete mixture. In response to the change in the strength of the sonic signal, one or more components of the sensor device are activated.

In one embodiment, components of a sensor device, such as the housing and other parts, may be formed of a thermosetting resin or a thermoplastic.

In one embodiment, a sensor device (such as any of those described herein) may have a housing with a square or rectangular shape, with a first side having a length between about 1.5 inch and about 2.0 inches, a second side having a length between about 1.5 inch and about 2.0 inches, and a thickness between about one-eight inch and one-half inch. In a preferred embodiment, a sensor device has a housing with a square shape with sides having a length of about one and three-fourths (1.75) inches, and a thickness of about three-sixteenth (3/16) inches.

In accordance with another embodiment, a system includes a sensor device having a sensor adapted to generate measurement data relating to a characteristic of a concrete mixture, and a transmitter adapted to transmit a first signal based on the measurement data. The system also includes a conductive wire forming a coil having a plurality of loops around the sensor device and a wire antenna. The coil is adapted to generate an electric current in response to the first signal. The antenna is adapted to transmit a second signal based on the electric current. The system is embedded in a concrete mixture and a portion of the antenna is exposed above the surface of the concrete mixture. The sensor device obtains measurement data and transmits a signal related to the measurement data. A current is induced in the coil due to electromagnetic induction. A second signal is transmitted via the wire antenna. The second signal is received and transmitted to a processor. The processor may analyze and/or store the signal.

In one embodiment, the coil includes at least five loops.

In another embodiment, the conductive wire comprises a metal. The conductive wire may be an insulated metal wire.

In another embodiment, the sensor device comprises a printed circuit board having a plurality of sensors. The plurality of sensors may include one of: a temperature sensor, an acceleration sensor, a motion sensor, a pH sensor, an inductance sensor, an impedance sensor, a resistivity sensor, a pressure sensor, a conductivity sensor, a salinity sensor, a humidity sensor, and an elevation sensor.

In another embodiment, the printed circuit board is disposed in a case.

In another embodiment, the sensor device is covered by a layer of a protective material. The protective material may be rubber or plastic, or a different material.

In accordance with another embodiment, a sensor device includes a housing, a sensor adapted to obtain a measurement, a wire extending from the housing, the wire having a length, the wire adapted to function as an antenna, and a transmitter adapted to transmit a signal via the wire, the signal having a wavelength related to the length of the wire. In some embodiments, the sensor device may include more than one wire extending from the housing.

In one embodiment, the signal includes information relating to the measurement.

In another embodiment, the wavelength of the signal is one of: twice the length of the wire, the length of the wire, one-half the length of the wire, and one-fourth the length of the wire.

In another embodiment, a communication system includes a concrete mixture, a sensor device embedded in the concrete mixture, and a wireless router adapted to receive signals from the sensor device. The wire(s) may be embedded entirely in the concrete mixture, or may extend above the surface of the concrete mixture.

In one embodiment, the sensor includes one of a temperature sensor, an accelerometer, a pH sensor, an inductance sensor, an impedance or resistivity sensor, a sonic sensor, a pressure sensor, a conductivity sensor, a salinity sensor, a humidity sensor, and an elevation sensor.

In accordance with another embodiment, a device includes a printed circuit board comprising one or more sensors adapted to obtain measurement data and a first antenna adapted to transmit a first signal based on the measurement data, a layer of a waterproof protective material covering at least a portion of the printed circuit board, and a conductive wire having a first portion that is wound around the printed circuit board to form a plurality of coils and a second portion that functions as a second antenna. The plurality of coils of the conductive wire responds to the first signal due to inductive coupling, thereby generating a second signal. The second antenna transmits the second signal. The protective material may be rubber or plastic, for example.

In one embodiment, the device is embedded in a concrete mixture.

These and other advantages of the present disclosure will be apparent to those of ordinary skill in the art by reference to the following Detailed Description and the accompanying drawings.

BRIEF DESCRIPTION OF THE DRAWINGS

FIG. 26D is a graph showing measurements of a sonic signal versus time in accordance with an embodiment.

DETAILED DESCRIPTION

It has been observed that embedding sensors into a concrete mixture can be a useful method for obtaining certain measurements relating to the concrete mixture. For example, embedding a temperature sensor in a concrete mixture can facilitate the gathering of temperature data, which can be useful in predicting the strength or maturity of the concrete mixture. Similarly, embedding a humidity sensor in a concrete mixture can facilitate the gathering of humidity data, which can also be useful in predicting the strength or maturity of the concrete mixture. When embedded in a concrete mixture, it is preferable that a humidity sensor be directly exposed to the water vapor within the concrete in order to directly measure the humidity of the concrete.

However, it has been observed that many types of sensors, such as temperature sensors, motion sensors, etc., are susceptible to damage when exposed to humidity. In addition, any electronics in a sensor may also be damaged by humidity. Therefore, it is often preferable to provide a protective seal for certain sensors (e.g., temperature sensors, motion sensors, etc.) and for any electronics on a sensor before embedding such sensors into a concrete mixture.

Accordingly, there is a need for improved systems, apparatus, and methods for embedding a humidity sensor into a concrete mixture in a manner that exposes the humidity sensor to the humidity of the concrete mixture, while protecting any electronic circuitry on the sensor, and any other attached sensors from exposure to the humidity of the concrete.

Figure 1:
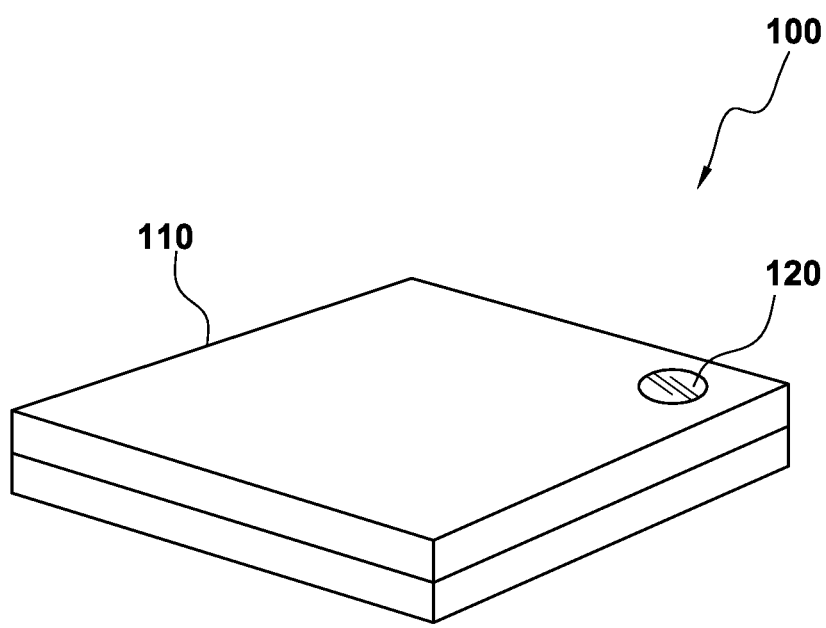
FIG. 1 shows a sensor in accordance with an embodiment.

FIG. 1 shows a sensor 100 in accordance with an embodiment. Sensor 100 includes a housing 110. Housing 110 includes a hole 120.

Figure 2:
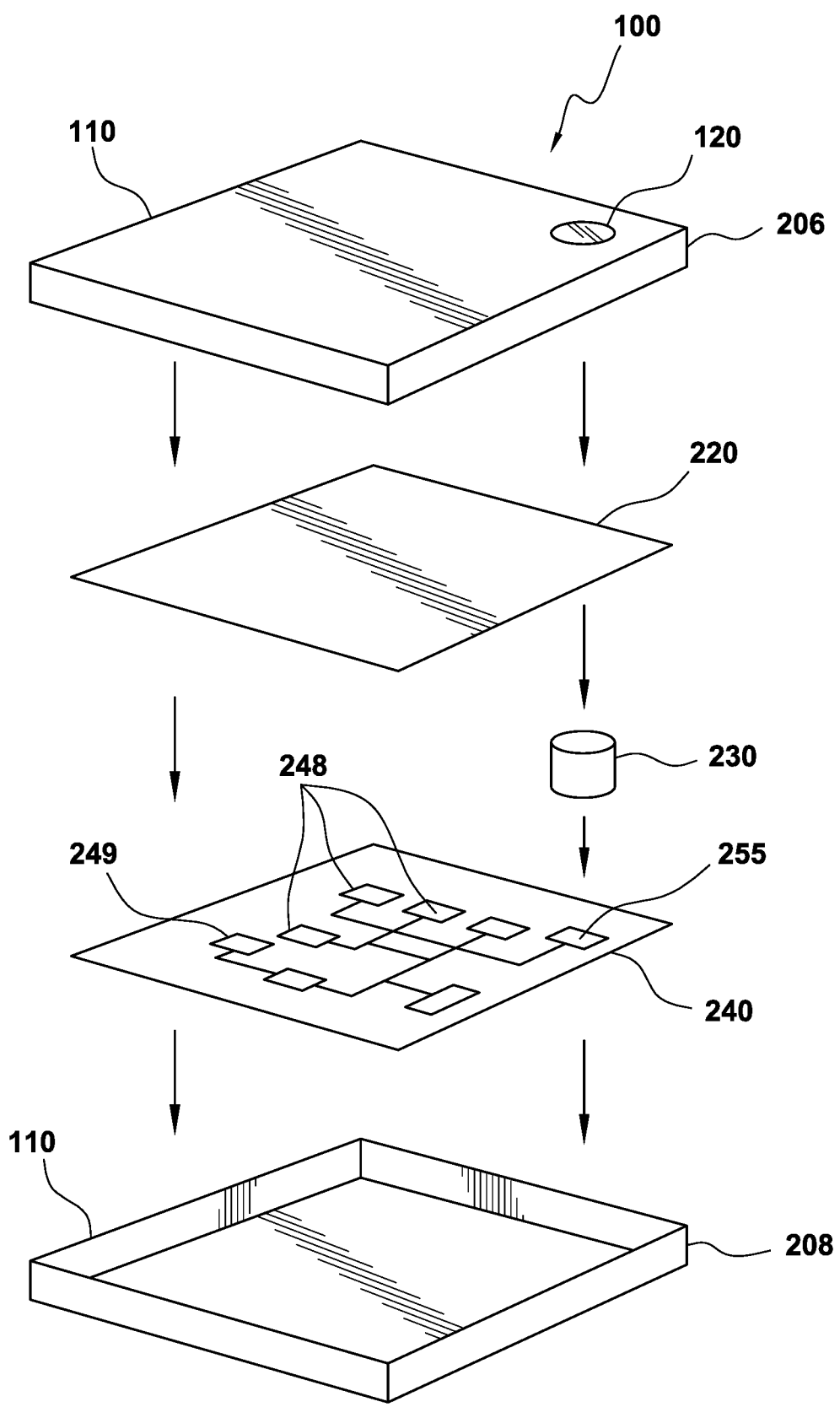
FIG. 2 shows components of the sensor of FIG. 1.

FIG. 2 shows components of the sensor of FIG. 1. Sensor 100 includes upper portion 206 and lower portion 208 of housing 110. Housing 110 may comprise plastic, metal, or other suitable material. Sensor may have a width between 0.5 inch and 3 inches, for example. Other dimensions may be used.

Sensor 100 also includes a layer 220 of waterproof material, a protective tube 230, and a printed circuit board (PCB) 240. PCB 240 includes a plurality of elements 248, which may include circuit components such as resistors, capacitors, amplifiers, etc., and/or one or more sensors adapted to obtain measurements relating to one or more characteristics such as temperature, motion, etc. For example, PCB 240 may include one or more of the following: a temperature sensor, a salinity sensor, a conductivity sensor, a motion sensor, a pH sensor, an acceleration sensor, a sonic sensor, etc. PCB 240 also includes a transceiver 249, which may include an antenna capable of sending and receiving data via wireless communication, for example. PCB 240 also includes a humidity sensor 255. PCB 240 may also include a battery or other power source.

PCB 240 fits into bottom portion 208. Tube 230 fits onto and over humidity sensor 255. A first end of tube that contacts PCB 240 surrounds humidity sensor 255. PCB 240 and tube 230 are constructed in such a manner that a seal is formed between tube 230 and PCB 240 when tube 230 is fitted onto and over humidity sensor 255. A second end of tube has a diameter that is larger than hole 120; therefore the second end surround hole 120.

Waterproof layer 220 fits above tube 230 between the second end of tube 230 and hole 120. Waterproof layer 220 includes a waterproof, breathable material. Therefore, waterproof layer 220 allows water vapor that enters hole 120 to pass through waterproof layer 220, but prevents water (or a concrete mixture) from passing through. Waterproof layer 220 may be formed from a waterproof, breathable fabric membrane such as Gore-Tex or other similar material. Upper portion 206 fits onto lower portion 208, creating a protective seal.

Figure 3:
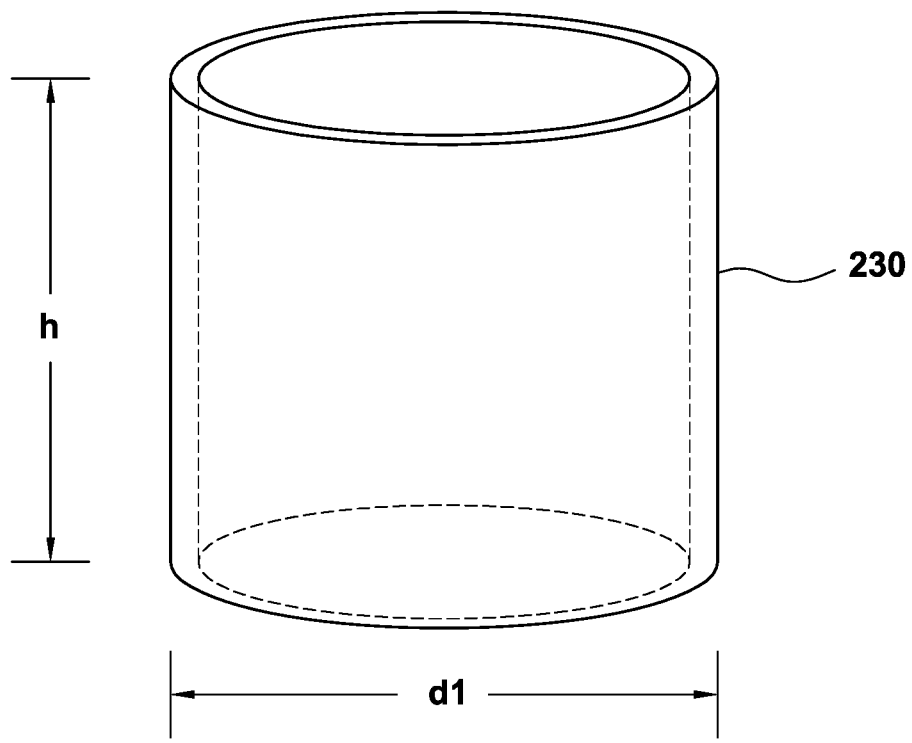
FIG. 3 shows a protective tube in accordance with an embodiment.

FIG. 3 shows protective tube 230 in accordance with an embodiment. Tube 230 may be formed of a waterproof material such as a plastic, rubber, or other material. Tube 230 has a diameter d1 that is determined by the size of humidity sensor 255. Tube 230 surrounds humidity sensor 255; therefore the diameter d1 of tube 230 is greater than the greatest dimension of humidity sensor 255. In one embodiment, diameter d1 of tube 230 is between 0.25 cm and 1.0 cm. Other diameters may be used.

Figure 4:
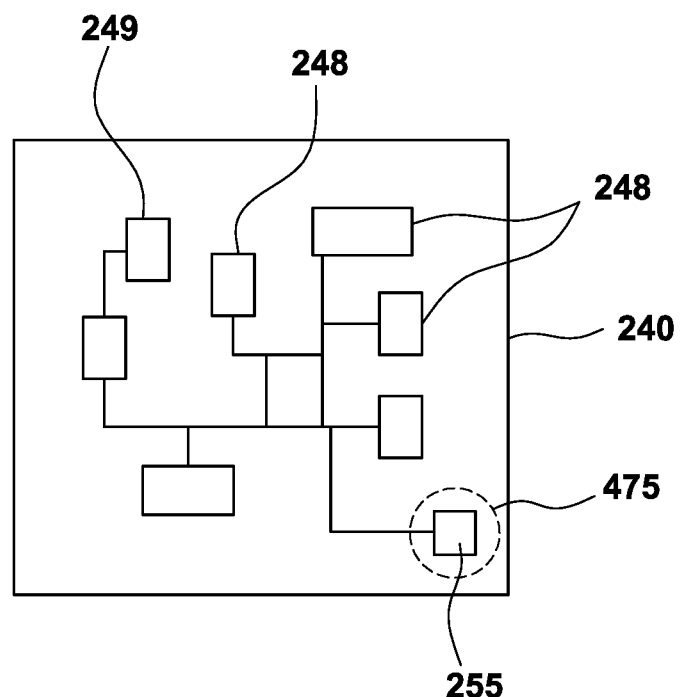
FIG. 4 shows a printed circuit board in accordance with an embodiment.

FIG. 4 shows PCB 240 in accordance with an embodiment. PCB 240 includes a groove 475 surrounding humidity sensor 255. Groove 475 is adapted to receive and support and end of tube 230.

Figure 5:
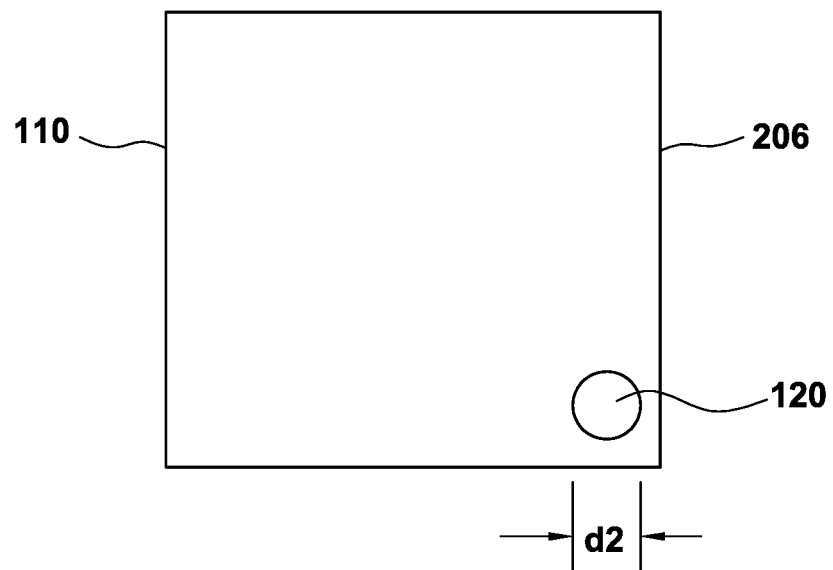
FIG. 5 shows a top view of an upper portion of a sensor in accordance with an embodiment.

FIG. 5 shows a top view of upper portion 206 in accordance with an embodiment. Hole 120 has a diameter d2. Diameter d2 is preferably equal to or smaller than diameter d1 of tube 230. However, any diameter may be used.

Figure 6:
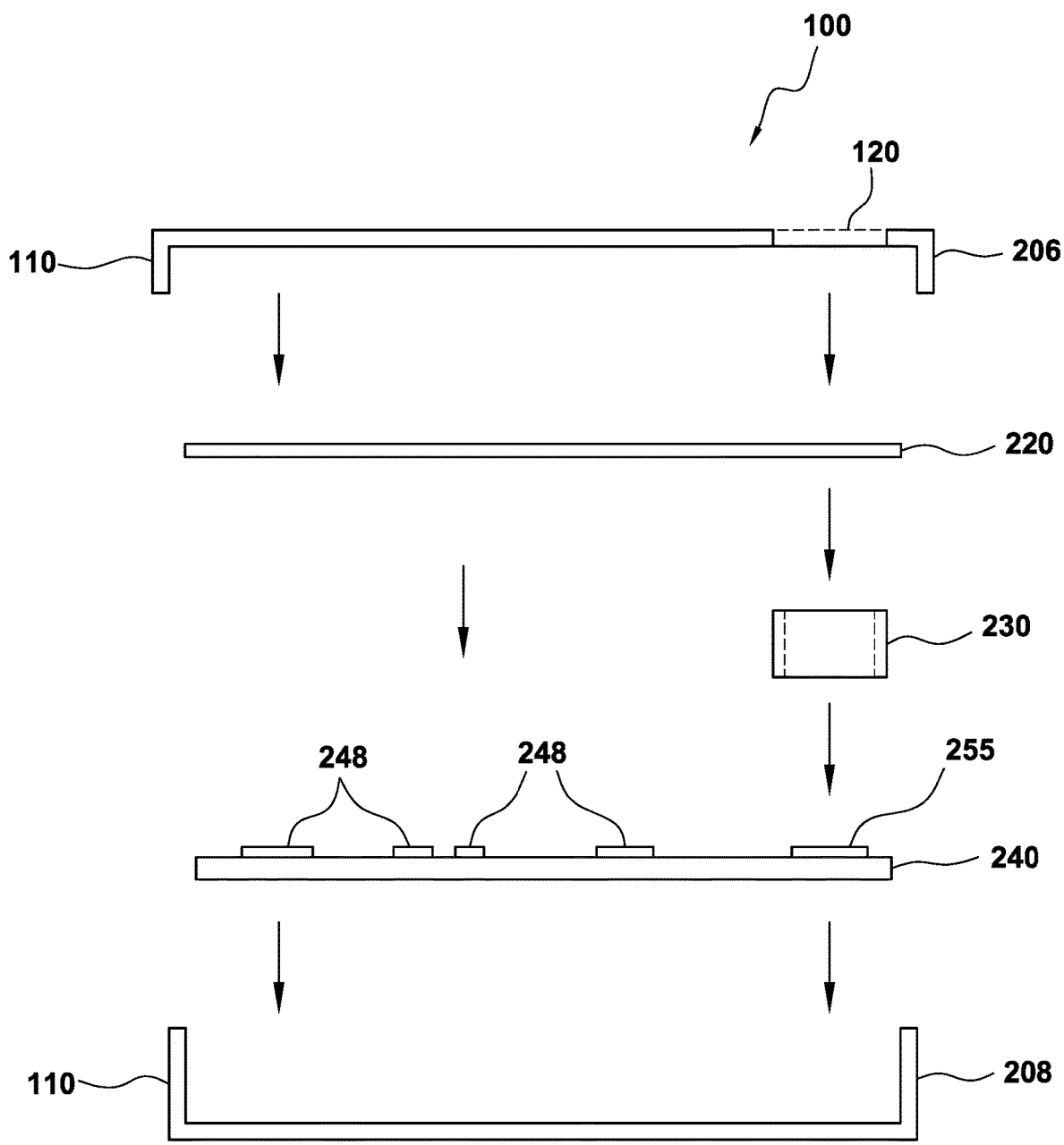
FIGS. 6-7 show cross-sectional views of components of a sensor in accordance with an embodiment.
Figure 7:
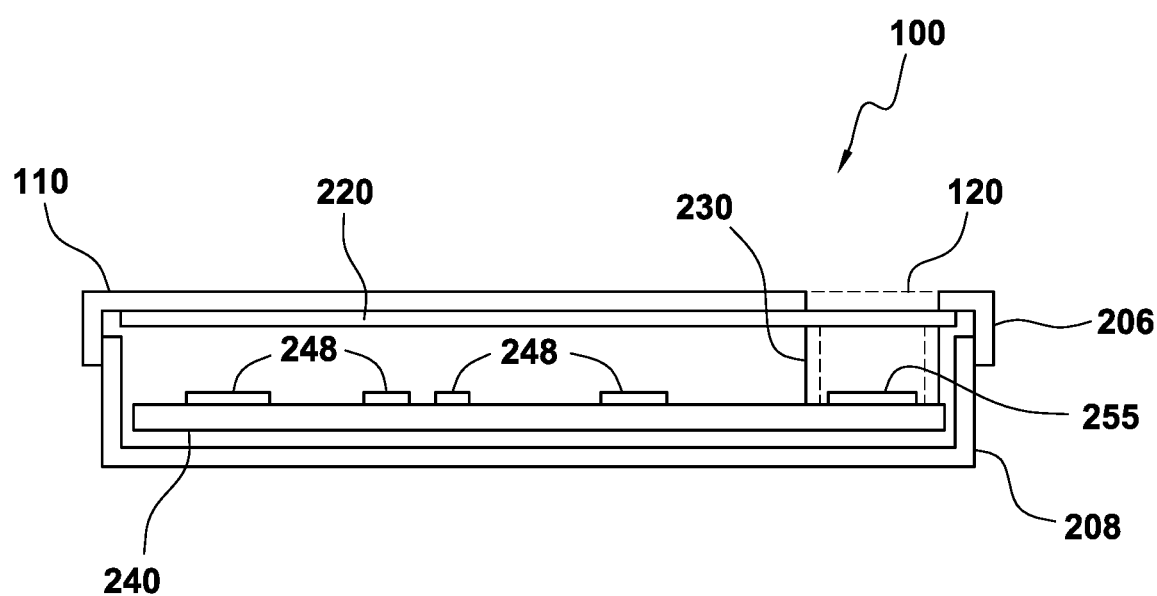

FIGS. 6 and 7 show cross-sectional views of components of sensor 100 in accordance with an embodiment. PCB 240 fits into bottom portion 208. Tube 230 fits onto and over humidity sensor 255. PCB 240 and tube 230 are constructed in such a manner that a first seal is formed between tube 230 and PCB 240 when tube 230 is fitted onto and over humidity sensor 255. Waterproof layer 220 fits above tube 230. Upper portion 206 fits onto lower portion 208, creating a protective seal between upper portion 206 and lower portion 208. As upper portion 206 is closed, a seal also forms between tube 230 and waterproof layer 220. FIG. 7 shows a cross sectional view of components of sensor 100 after upper portion 206 has been fitted onto lower portion 208.

Advantageously, as upper portion 206 is closed over lower portion 208, a first seal is formed between tube 230 and PCB 240, a second seal is formed between tube 230 and waterproof layer 220, and a third seal is formed between waterproof layer 220 and upper portion 206. After these seals are formed, tube 230 defines a volume between hole 120 and humidity sensor 255 that is partially exposed to the surrounding environment. Hole 120 allows water vapor to enter the interior of sensor 100 and reach humidity sensor 255, enabling humidity sensor 255 to measure the humidity of the surrounding environment. Waterproof layer 220 is breathable and allows water vapor to pass through to humidity sensor 255; however, waterproof layer 220 prevents any water (or concrete mixture) from passing through to the interior of sensor 100. In addition, tube 230 advantageously prevents any water vapor that enters through hole 120 from reaching other components of sensor 100. For example, tube 230 protects components 248 (and transceiver 249) from the humidity of the surrounding environment.

In accordance with an embodiment, sensor 100 may be used to obtain measurements of humidity of a concrete mixture. In one embodiment, sensor 100 may be placed on top of the surface of a concrete mixture, with hole 120 facing down (into the concrete mixture). In another embodiment, sensor 100 may be embedded within a concrete mixture. For example, sensor 100 may be embedded several inches or several feet beneath the surface of a concrete mixture.

Figure 8:
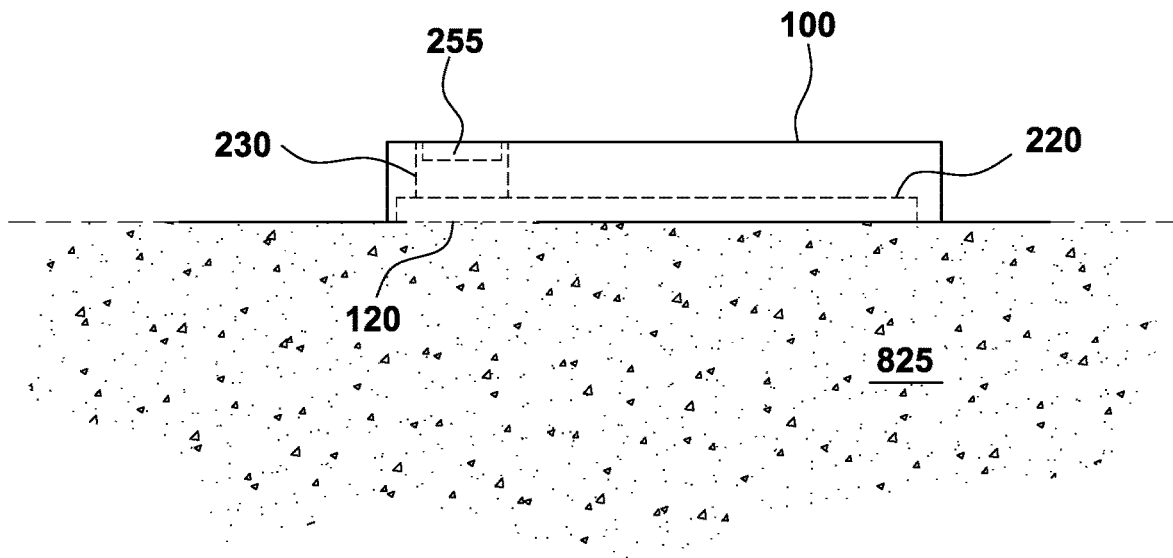
FIG. 8 shows a sensor disposed on a surface of a concrete mixture in accordance with an embodiment.

FIG. 8 shows sensor 100 disposed on a surface of a concrete mixture 825 in accordance with an embodiment. Hole 120 faces downward, proximate the surface of concrete 825. Because hole 120 faces downward, water vapor from concrete mixture 825 readily passes through hole 120, and through layer 220, and reaches humidity sensor 255. Humidity sensor 255 may obtain humidity measurements of the humidity of concrete mixture 825. Sensor 100 may transmit the humidity measurements to a second device via wireless transmission, for example.

Figure 9:
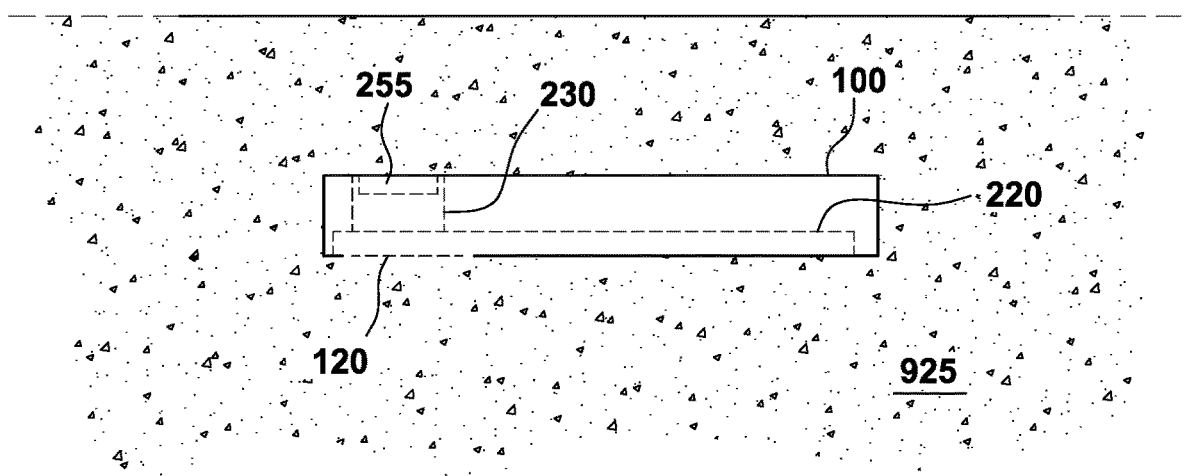
FIG. 9 shows a sensor embedded beneath the surface of a concrete mixture in accordance with an embodiment.

FIG. 9 shows sensor 100 embedded beneath the surface of a concrete mixture 925 in accordance with an embodiment. Hole 120 faces downward. Water vapor from concrete mixture 925 readily passes through hole 120, and through layer 220, and reaches humidity sensor 255. Humidity sensor 255 may obtain humidity measurements of the humidity of concrete mixture 925. Sensor 100 may transmit the humidity measurements to a second device via wireless transmission, for example. In the illustrative embodiment, sensor 100 may transmit data wirelessly through a layer of concrete.

Figure 10:
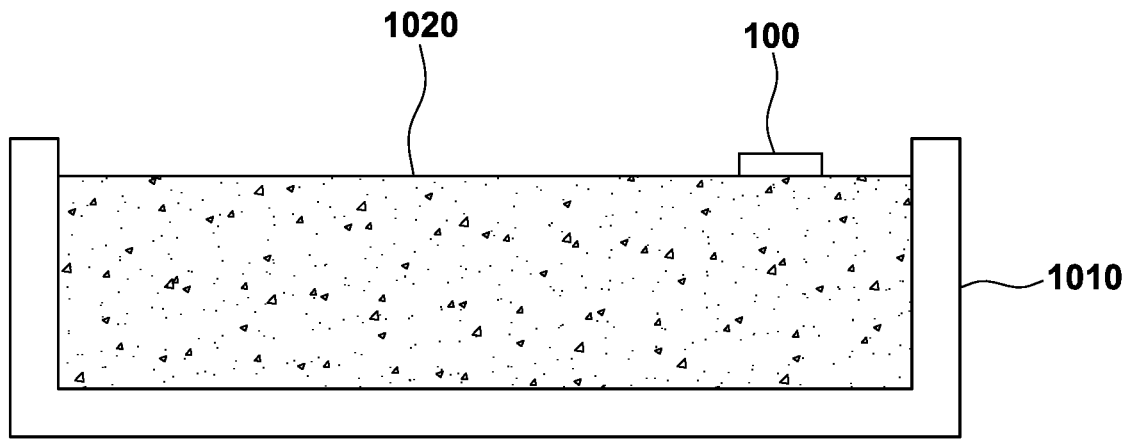
FIG. 10 shows a concrete mixture in a form in accordance with an embodiment.

Sensor 100 may be used in this manner at a construction site, for example. FIG. 10 shows a concrete mixture 1020 in a form 1010 in accordance with an embodiment. Sensor 100 is disposed on the surface of the concrete. Sensor 100 may obtain measurements of the humidity of concrete mixture 1020. Sensor 100 may transmit the humidity measurements to a second device via wireless transmission.

Figure 11:
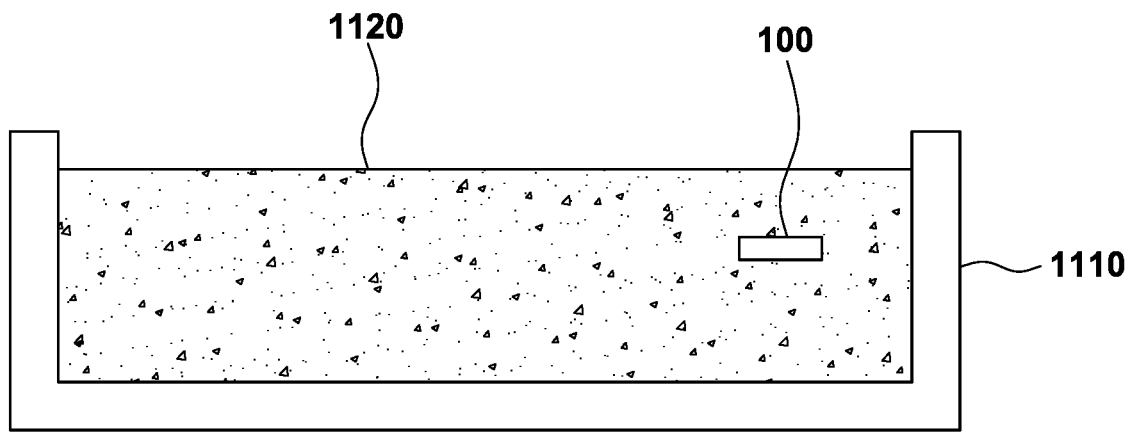
FIG. 11 shows a concrete mixture in a form in accordance with another embodiment.

FIG. 11 shows a concrete mixture 1120 in a form 1110 in accordance with another embodiment. Sensor 100 is embedded under the surface of the concrete. Sensor 100 may obtain measurements of the humidity of concrete mixture 1120. Sensor 100 may transmit the humidity measurements to a second device via wireless transmission.

Figure 12:
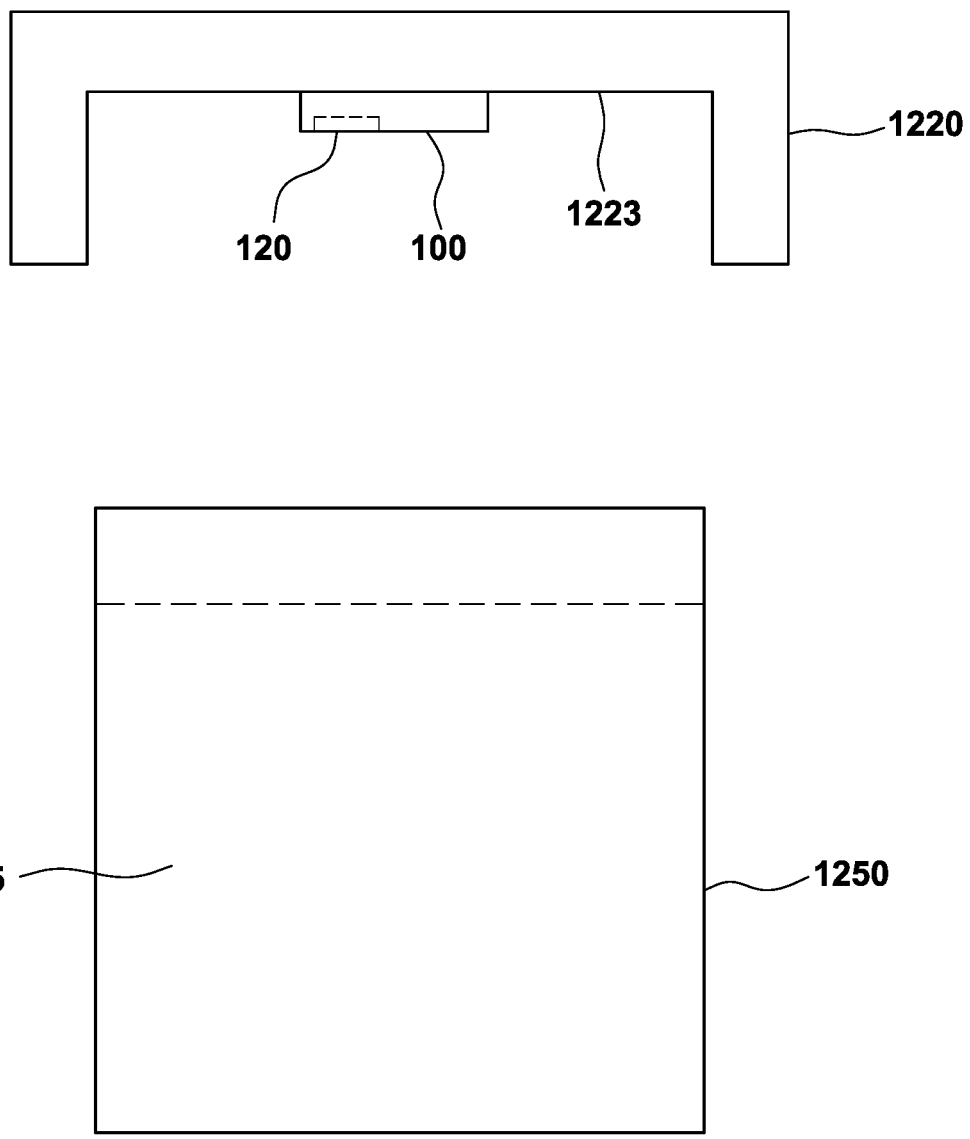
FIG. 12 shows a test cylinder and a cap in accordance with an embodiment.

In another embodiment, a sensor may be attached to a cap and placed on a standard test cylinder used to test specimens of concrete. FIG. 12 shows a test cylinder and a cap in accordance with an embodiment. Test cylinder 1250 may be a 4×8-inch or 6×12-inch test cylinder, for example. Test cylinder 1250 contains a specimen of concrete 1275. A cap 1220 is constructed to fit onto test cylinder 1250. Sensor 100 is attached to an interior surface 1223 of cap 1220. Sensor 100 is oriented so that hole 120 faces downward.

Figure 13:
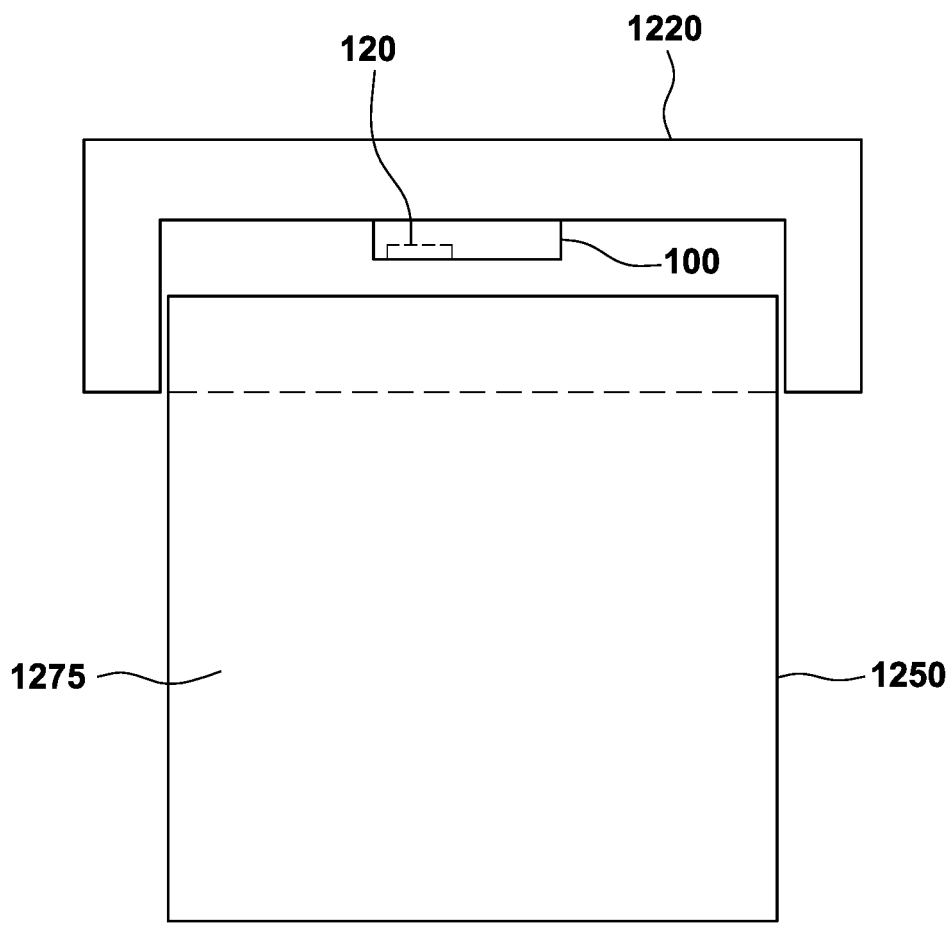
FIG. 13 shows a test cylinder and a cap placed on the test cylinder in accordance with an embodiment.

Cap 1220 may be placed onto test cylinder 1250, as shown in FIG. 13. Cap 1220 may form a seal when placed onto test cylinder 1250. After cap 1220 has been placed onto test cylinder 1250, sensor 100 may obtain measurements of humidity. Because hole 120 faces downward, humidity generated by concrete 1275 may enter sensor 100 through hole 120. A sensor attached to a cap such as cap 1220 may be used in a similar manner to obtain measurements of other characteristics of a concrete mixture contained in a test cylinder, such as temperature, motion, etc.

Devices, systems, apparatus and methods for using a sensor device attached to a cap placed on a concrete test cylinder to obtain measurements of one or more characteristics of a concrete mixture contained in the test cylinder are described, for example, in U.S. patent application Ser. No. 15/414,401, filed Jan. 24, 2017 and entitled "SYSTEMS, APPARATUS AND METHODS FOR OBTAINING MEASUREMENTS CONCERNING THE STRENGTH AND PERFORMANCE OF CONCRETE MIXTURES," which is hereby incorporated by reference herein in its entirety and for all purposes.

Figure 14:
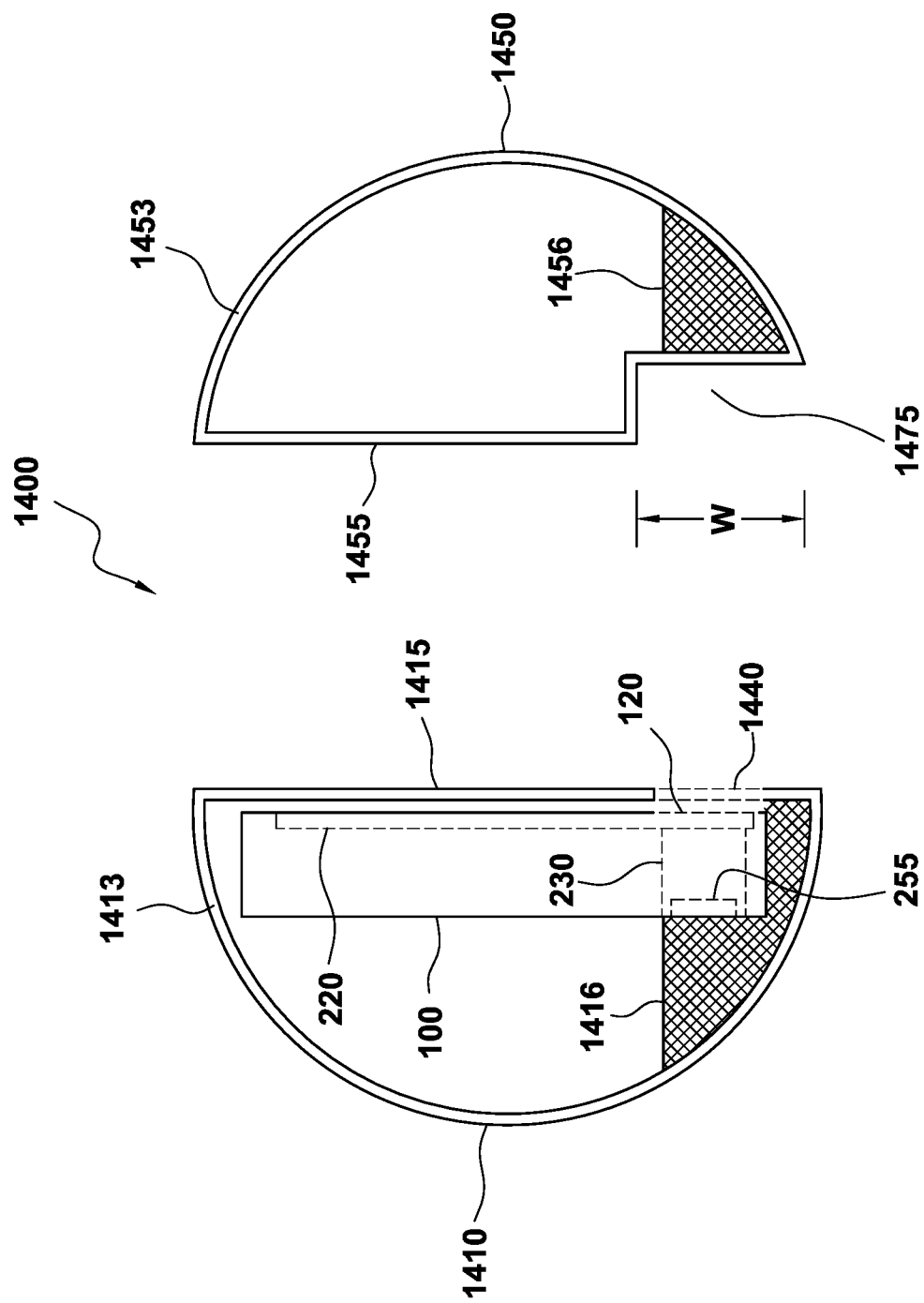
FIG. 14 shows a cross-sectional view of components of a sensing device in accordance with an embodiment.

In other embodiments, sensor 100 may be placed within a sensing device. FIG. 14 shows a cross-sectional view of components of a sensing device in accordance with an embodiment. Sensing device 1400 includes a first portion 1410 and a second portion 1420. First portion 1410 has a hemispherical shaped side 1413 and a flat side 1415. Flat side 1415 has a hole 1440 that is approximately the same size as hole 120 of sensor 100. Sensor 100 is disposed within first portion 1410, proximate the flat side 1415, such that hole 120 of sensor 100 is proximate hole 1440. A predetermined quantity of a substance such as lead is disposed inside of first portion 1410, on the side near hole 120 and hole 1440.

Second portion 1450 has a hemispherical shaped side 1453 and a flat side 1455. Flat side 1455 has a notch 1475 on one side. A width W of notch 1475 is greater than the width of hole 1440. A predetermined quantity of a substance such as lead is disposed inside of second portion 1450, on the side near notch 1475.

Figure 15:
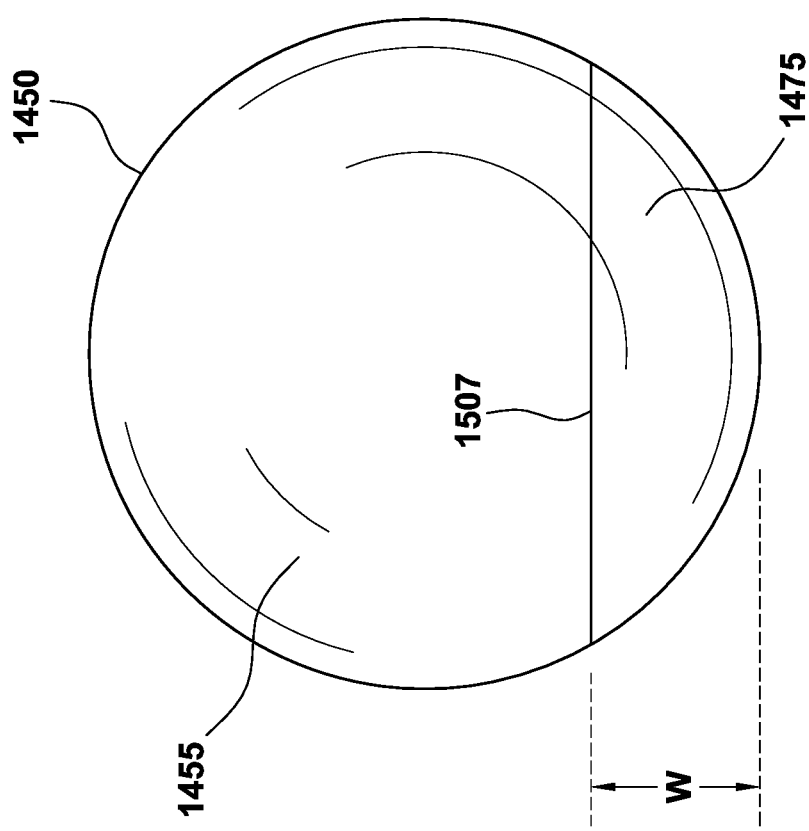
FIG. 15 shows a view of a flat side of a portion of the sensing device of the embodiment of FIG. 14.

FIG. 15 shows a view of flat side 1455 of second portion 1450 of sensing device 1400 in accordance with the embodiment of FIG. 14. Notch 1475 runs longitudinally across flat side 1455, defining a chord 1507.

First portion 1410 and second portion 1450 may be joined to form sensing device 1400. Specifically, flat side 1415 of first portion 1410 is attached to flat side 1455 of second portion 1450.

Figure 16:
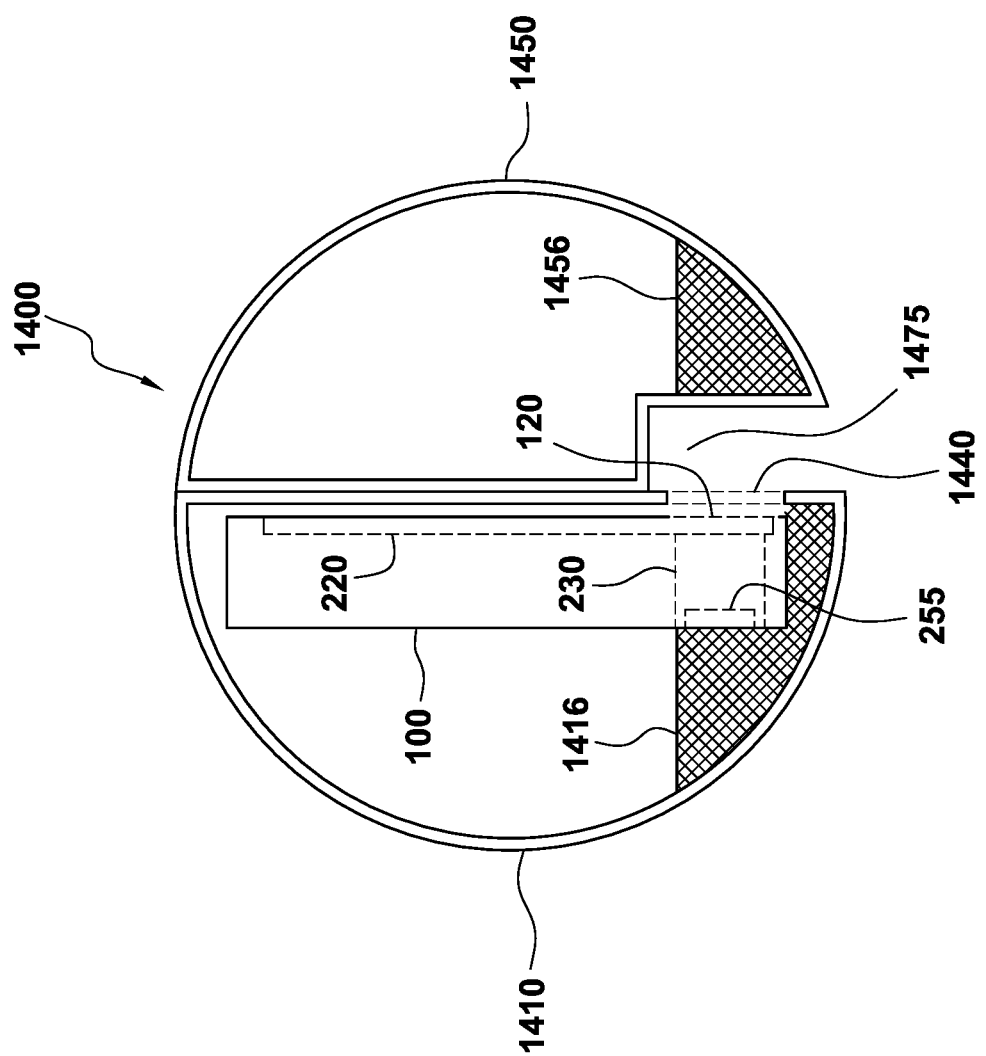
FIG. 16 shows a cross-sectional view of a sensing device in accordance with an embodiment.

FIG. 16 shows a cross-sectional view of sensing device 1400 in accordance with an embodiment. Sensing device 1400 has a spherical, or approximately spherical, shape. Notch 1475 ensure that hole 1440 is exposed to the surrounding environment.

In accordance with an embodiment, sensing device 1400 may be inserted, or partially inserted, into a concrete mixture. While in the concrete mixture, sensor 100 within sensing device 1400 may obtain measurements of the humidity of the concrete mixture.

Figure 17:
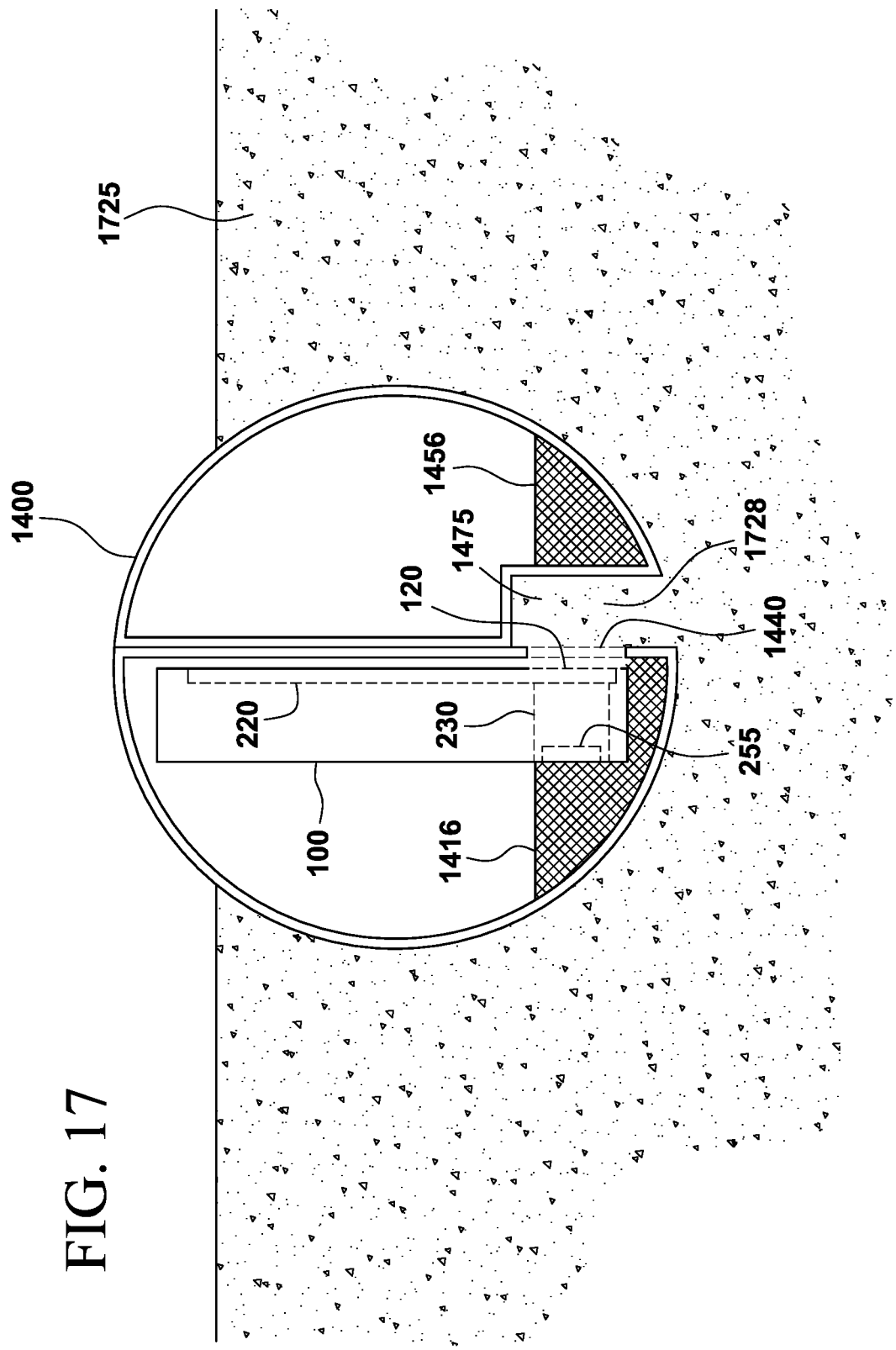
FIG. 17 shows a sensing device embedded in a concrete mixture in accordance with an embodiment.

FIG. 17 shows sensing device 1400 embedded in a concrete mixture 1725 in accordance with an embodiment. For example, sensing device 1400 may be inserted into a concrete mixture within a form at a construction site. The weight of material 1416 and material 1456 cause sensing device to orient itself with the notch 1475 on the underside of the device. Therefore, notch 1475 is embedded within the concrete mixture. A portion 1728 of the concrete enters notch 1475. Humidity from the concrete within notch 1475 enters hole 1440 of sensing device 1400, and enters hole 120 of sensor 100. Humidity sensor 255 may therefore measure the humidity of concrete 1725. Sensor 100 may transmit the humidity measurements via wireless transmission to a remote device.

Figure 18:
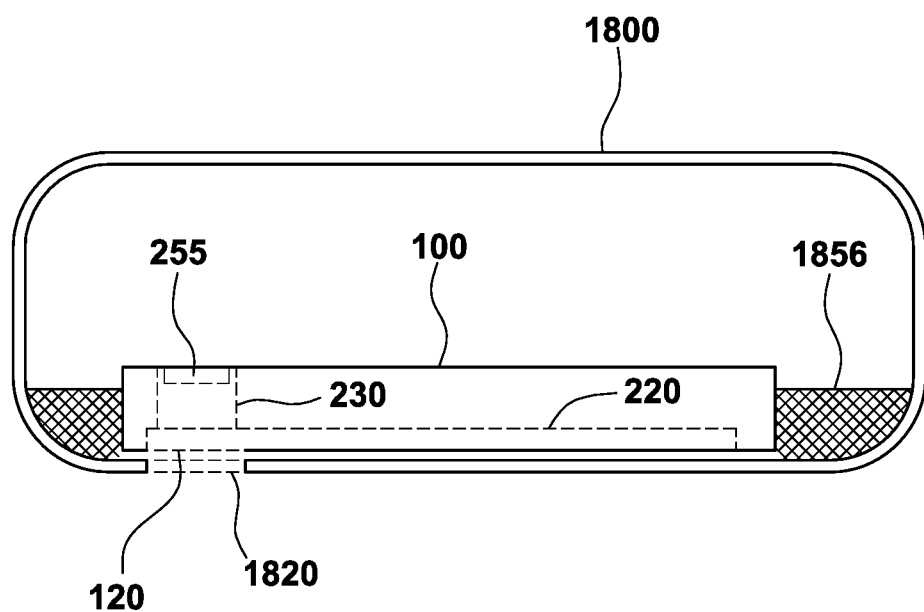
FIG. 18 shows a sensing device in accordance with another embodiment.

In another embodiment, sensor 100 may be disposed within a sensing device having a different shape, such as a rectangular prism, a triangular prism, a cube, a disc, etc. FIG. 18 shows a sensing device 1800 in accordance with another embodiment. Sensing device 1800 has a cuboid shape (a rectangular prism with rounded edges). A hole 1820 is disposed on one side of sensing device 1800. Hole 120 of sensor 100 is disposed proximate to hole 1820 of sensing device 1800. In this manner, humidity of the surrounding environment may enter through hole 1820 and hole 120 and reach humidity sensor 255.

In accordance with an embodiment, data obtained by sensor 100 may be transmitted via a network to a processor. The processor analyzes the data and generates a prediction relating to a characteristic of a concrete mixture based on the data. For example, humidity measurements obtained by sensor 100 may be used to generate a prediction of strength or maturity of a concrete mixture. Data from multiple sensors may be received and used to generate multiple predictions.

Figure 19:
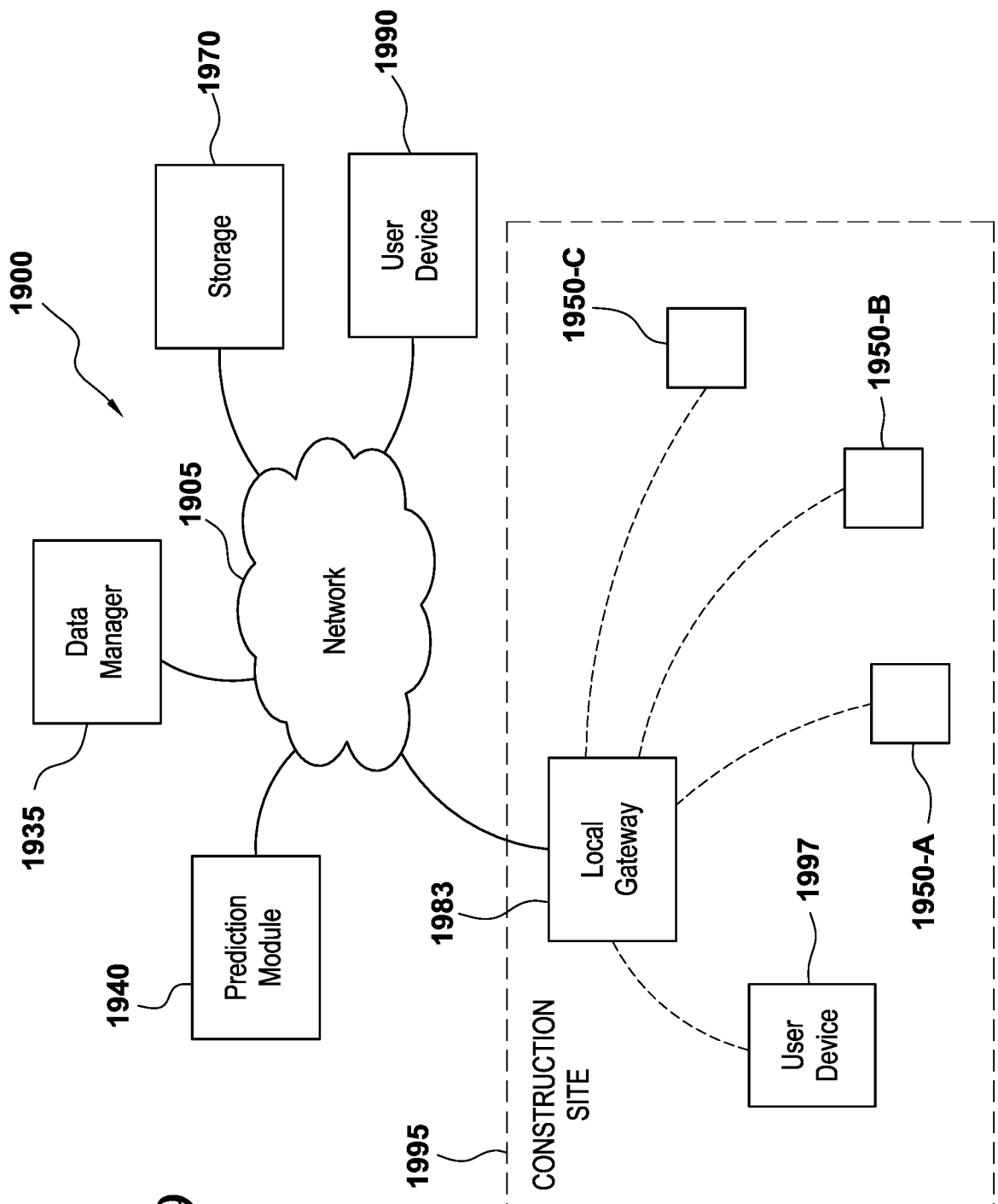
FIG. 19 shows a communication system in accordance with an embodiment.

FIG. 19 shows a communication system in accordance with an embodiment. Communication system 1900 includes a network 1905, which may include the Internet, for example, a data manager 1935, a prediction manager 1940, and a storage 1970. Communication system 1900 also includes a user device 1990, which may be a personal computer, a laptop device, a cell phone, a tablet device, etc.

Communication system 1900 also includes a local gateway 1983, which is connected to network 1905. Local gateway 1983 may include a wireless modem, for example. Local gateway 1983 is located at a construction site 1995, and is linked to a plurality of sensing devices 1950-A, 1950-B, 1950-C, etc., which are disposed at various locations at the construction site. Each sensing device 1950 includes a sensor similar to sensor 100. Each sensing device 1950 may be similar to sensing device 1400 described herein, for example.

Sensing devices 1950 are disposed at various sites at a construction site. For example, a sensing device 1950-A may be embedded in a first concrete form, sensing device 1950-B may be embedded in a second concrete form, etc. Using methods and apparatus similar to those described above, each sensing device 1950 obtains humidity measurements related to a respective concrete mixture. Each sensing device 1950 transmits measurement data to data manager 1935 via local gateway 1983 and network 1905. For example, each sensing device 1950 may transmit measurement data wirelessly to local gateway 1983, which transmits the measurement data to data manager 1935 via network 1905. Each sensing device 1950 may also transmit an identifier uniquely identifying itself. For example, an RFID tag embedded in each sensing device 1950 may transmit identification information. Communication system 1900 may include any number of sensing devices.

In one embodiment, multiple sensing devices 1950 may be located at a single location (e.g., a single construction site). In another embodiment, multiple sensing devices 1950 may be located at multiple locations (e.g., at multiple construction sites).

Communication system 1900 also includes a user device 1997, which may be a personal computer, laptop device, tablet device, cell phone, or other processing device which is located at a construction site and used by a technician at the site. User device 1997 may communicate with network 1905, with local gateway 1983, with a sensing device 1950, and/or with other devices within communication system 1900.

Data manager 1935 receives humidity measurement data from one or more sensing devices 1950 and may analyze the measurement data. In the illustrative embodiment, data manager 1935 transmits the measurement data to prediction manager 1940 (or otherwise makes the data available to prediction manager 1940). Prediction manager 1940 may generate predictions concerning the behavior of one or more concrete specimens. For example, prediction manager 1940 may receive humidity data from sensing device 1950-A and, based on the measurement data, generate predictions regarding the water-to-cementitious ratio, durability, strength, slump, maturity, etc., of the concrete mixture in which sensing device 1950-A is located. In one embodiment, the measurement data received by data manager 1935 is provided to a real-time model to project setting behavior and strength for the entire batch of concrete. In another embodiment, the measurement data is continually subject to statistical analysis to generate real-time projections, control charts, etc. Data manager 1935 may store the measurement data and/or the prediction data in storage 1970. For example, measurements and/or prediction data may be stored in a database. Other data structures may be used to store measurement and/or prediction data.

In one embodiment, data manager 1935 may transmit measurement data and/or prediction information relating to water-to-cementitious ratio, durability, strength, slump, maturity, etc. to a user device such as user device 1990 or user device 1997 to enable a technician to access and view the information. For example, user device 1990 and/or user device 1997 may display measurement data and/or prediction data on a web page, or in another format.

In one embodiment, storage 1970 includes a cloud storage system. Data obtained by a sensing device 1950 may be transmitted to and saved in storage 1970 in real-time. A cloud implementation such as that illustrated by FIG. 19 may allow data from projects in multiple regions or multiple countries to be auto-consolidated in a single database.

Figure 20:
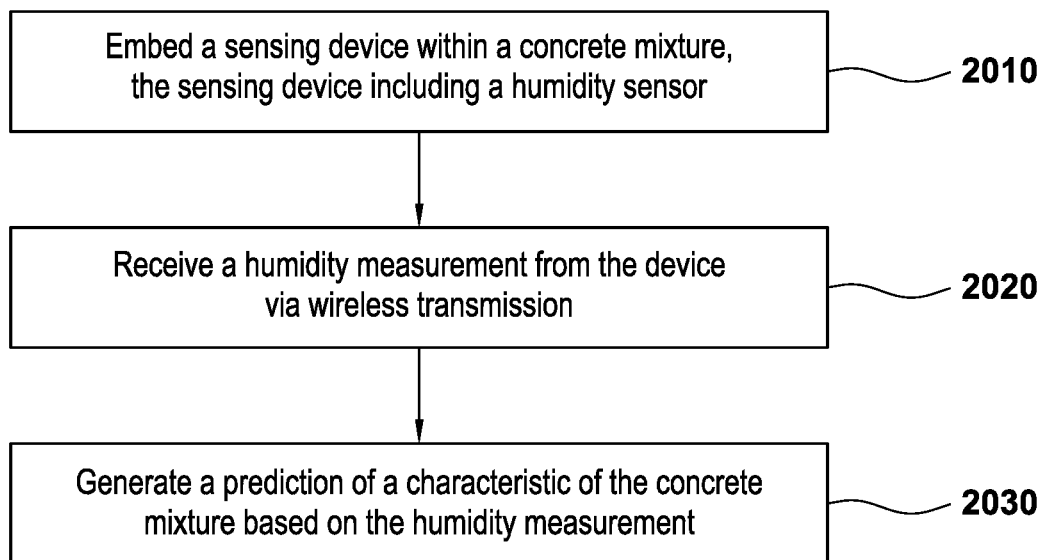
FIG. 20 is a flowchart of a method in accordance with an embodiment.

FIG. 20 is a flowchart of a method in accordance with an embodiment. At step 2010, a sensing device is embedded within a concrete mixture, the sensing device including a humidity sensor. At step 2020, a humidity measurement is received from the device via wireless transmission. At step 2030, a prediction of a characteristic of the concrete mixture is generated based on the humidity measurement.

Figure 21A:
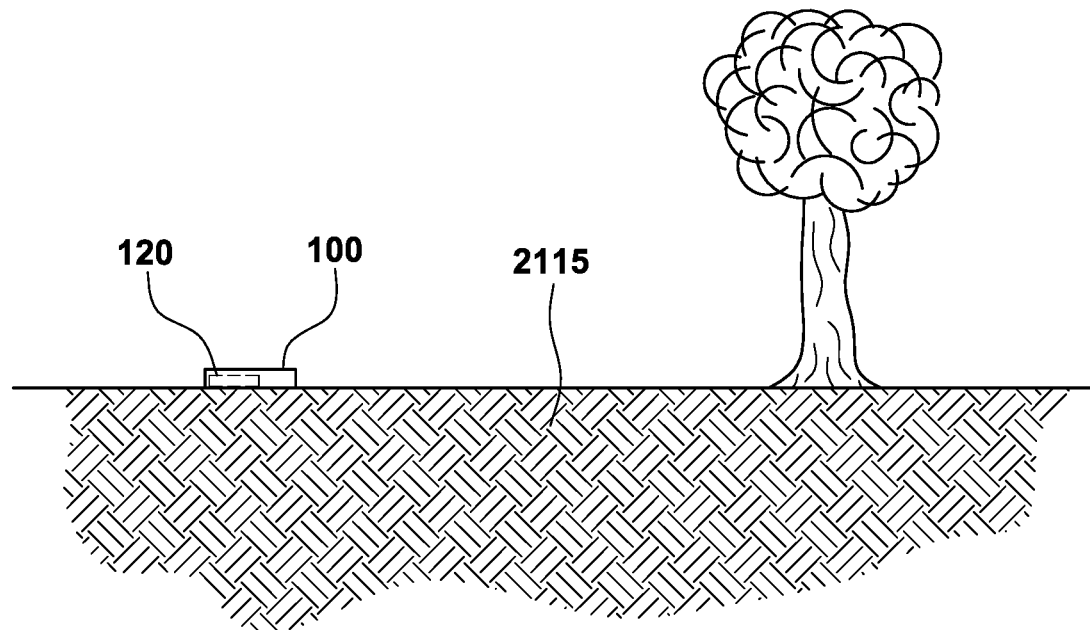
FIG. 21A shows a sensor disposed on the surface of soil in accordance with an embodiment.
Figure 21B:
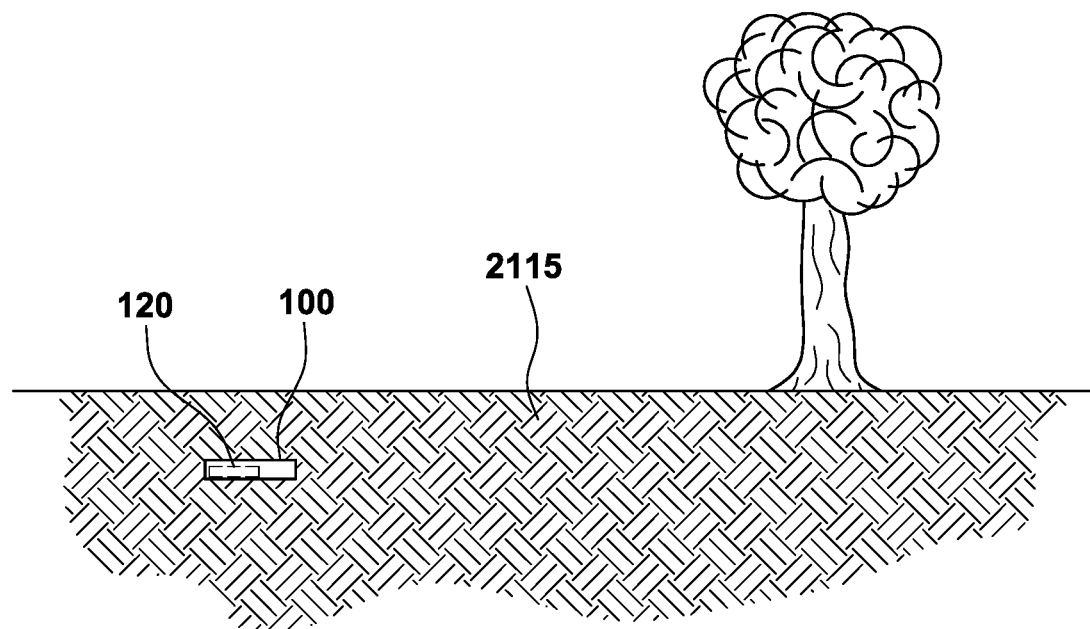
FIG. 21B shows a sensor embedded under the surface of soil in accordance with an embodiment.

While embodiments have been discussed herein in the context of the concrete production and testing and construction industries, systems, methods, and apparatus described herein may be used in other fields and for other uses, as well. For example, a sensor similar to sensor 100 described herein, and/or a sensing device such as sensing device 1400 described herein, may be used in an agricultural setting to determine the humidity of soil. For example, a sensor may be placed on top of the soil, or buried several inches or feet under the soil. FIG. 21A shows sensor 100 disposed on the surface of soil 2115 in accordance with an embodiment. FIG. 21B shows sensor 100 embedded under the surface of soil 2115 in accordance with another embodiment. In the manner described herein, sensor 100 may obtain measurements of the humidity of soil 2115, and transmit the measurement data to a remote device via wireless transmission. A prediction of a characteristic of soil 2115 may then be generated based on the measurement data.

In other embodiments, sensors and sensing devices described herein may be used to analyze other substances including, without limitation, water, water mixtures, chemical products, paint, petroleum-based substances, food products, etc.

In various embodiments, the method steps described herein, including the method steps described in FIG. 20, may be performed in an order different from the particular order described or shown. In other embodiments, other steps may be provided, or steps may be eliminated, from the described methods.

Systems, apparatus, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be used within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIG. 20, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 22:
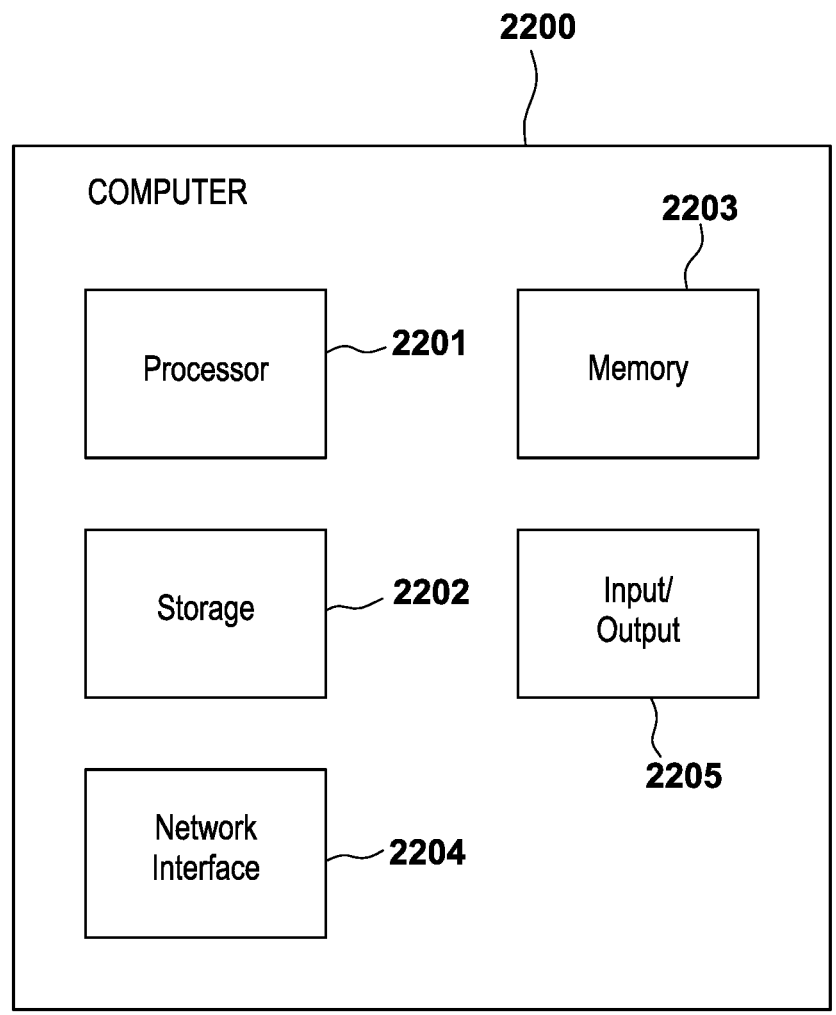
FIG. 22 shows a high-level block diagram of an exemplary computer that may be used to implement certain embodiments.

A high-level block diagram of an exemplary computer that may be used to implement systems, apparatus and methods described herein is illustrated in FIG. 22. Computer 2200 includes a processor 2201 operatively coupled to a data storage device 2202 and a memory 2203. Processor 2201 controls the overall operation of computer 2200 by executing computer program instructions that define such operations. The computer program instructions may be stored in data storage device 2202, or other computer readable medium, and loaded into memory 2203 when execution of the computer program instructions is desired. Thus, the method steps of FIG. 20 can be defined by the computer program instructions stored in memory 2203 and/or data storage device 2202 and controlled by the processor 2201 executing the computer program instructions. For example, the computer program instructions can be implemented as computer executable code programmed by one skilled in the art to perform an algorithm defined by the method steps of FIG. 20. Accordingly, by executing the computer program instructions, the processor 2201 executes an algorithm defined by the method steps of FIG. 20. Computer 2200 also includes one or more network interfaces 2204 for communicating with other devices via a network. Computer 2200 also includes one or more input/output devices 2205 that enable user interaction with computer 2200 (e.g., display, keyboard, mouse, speakers, buttons, etc.).

Processor 2201 may include both general and special purpose microprocessors, and may be the sole processor or one of multiple processors of computer 2200. Processor 2201 may include one or more central processing units (CPUs), for example. Processor 2201, data storage device 2202, and/or memory 2203 may include, be supplemented by, or incorporated in, one or more application-specific integrated circuits (ASICs) and/or one or more field programmable gate arrays (FPGAs).

Data storage device 2202 and memory 2203 each include a tangible non-transitory computer readable storage medium. Data storage device 2202, and memory 2203, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 2205 may include peripherals, such as a printer, scanner, display screen, etc. For example, input/output devices 2205 may include a display device such as a cathode ray tube (CRT) or liquid crystal display (LCD) monitor for displaying information to the user, a keyboard, and a pointing device such as a mouse or a trackball by which the user can provide input to computer 2200.

Any or all of the systems and apparatus discussed herein, including sensor 100, sensing device 1400, data manager 1935, prediction module 1940, storage 1970, local gateway 1983, user device 1990, and user device 1997, and components thereof, may be implemented using a computer such as computer 2200.

One skilled in the art will recognize that an implementation of an actual computer or computer system may have other structures and may contain other components as well, and that FIG. 22 is a high level representation of some of the components of such a computer for illustrative purposes.

In accordance with another embodiment, a sensor is embedded in a layer of concrete (e.g., within a concrete floor or other surface). A second layer of a selected material (e.g., rubber) is deposited on top of the concrete layer. The second layer may be deposited on the concrete to function as a protective layer or for another reason. The sensor obtains measurements of one or more characteristics of the concrete and transmits the information. A second device receives the measurement data and may predict a second characteristic of the concrete based on the measurement data.

Figure 23A:
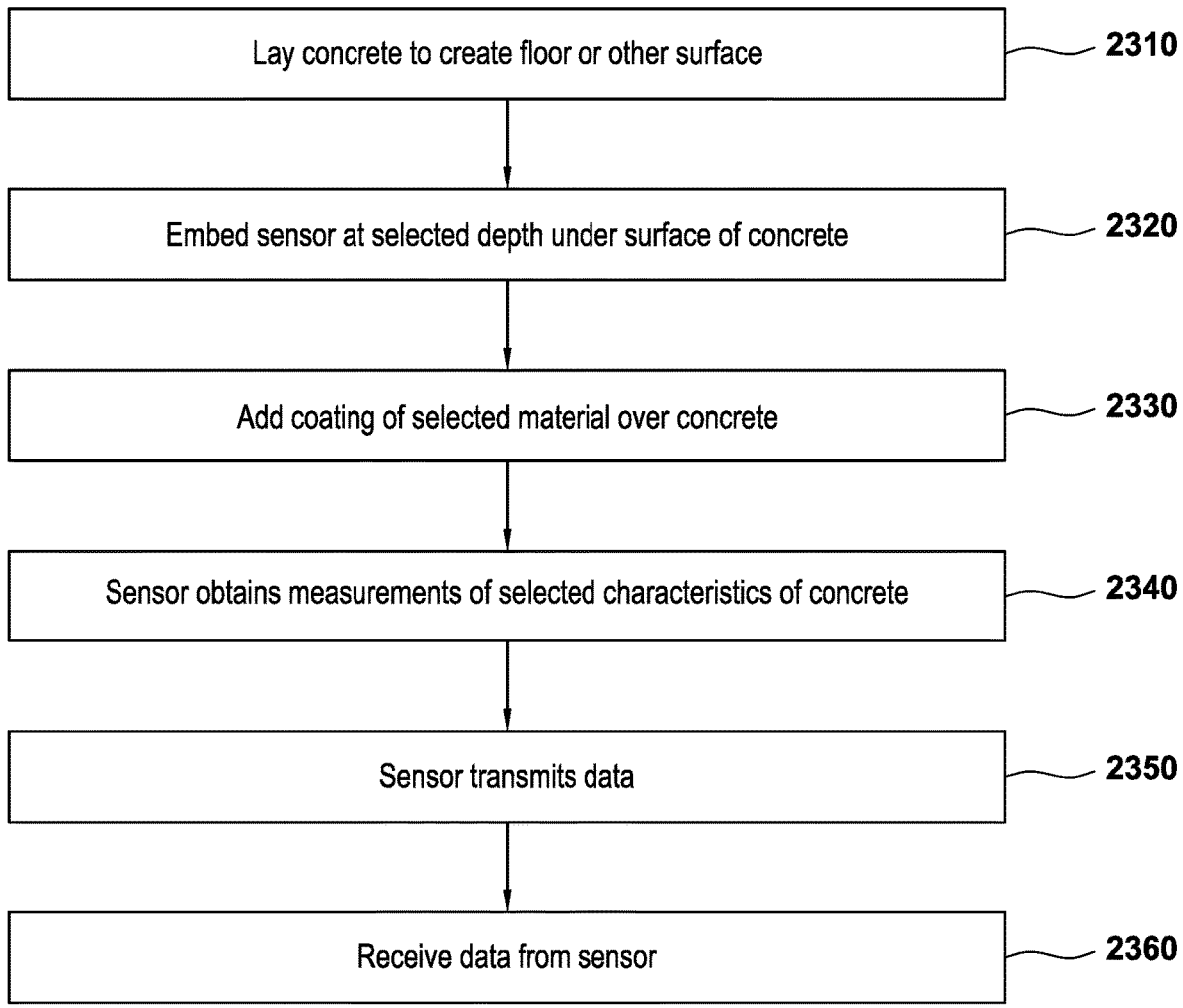
FIG. 23A is a flowchart of a method of obtaining data relating to characteristics of a concrete mixture in accordance with an embodiment.

FIG. 23A is a flowchart of a method of determining one or more characteristics of concrete in accordance with an embodiment. At step 2310, concrete is laid to create a floor or other surface. At step 2320, a sensor is embedded under the surface of the concrete at a selected depth. For example, the sensor may be embedded at a depth of approximately one inch. A sensor may be embedded at other depths. At step 2330, a coating of a selected material is added over the concrete.

Figure 23B:
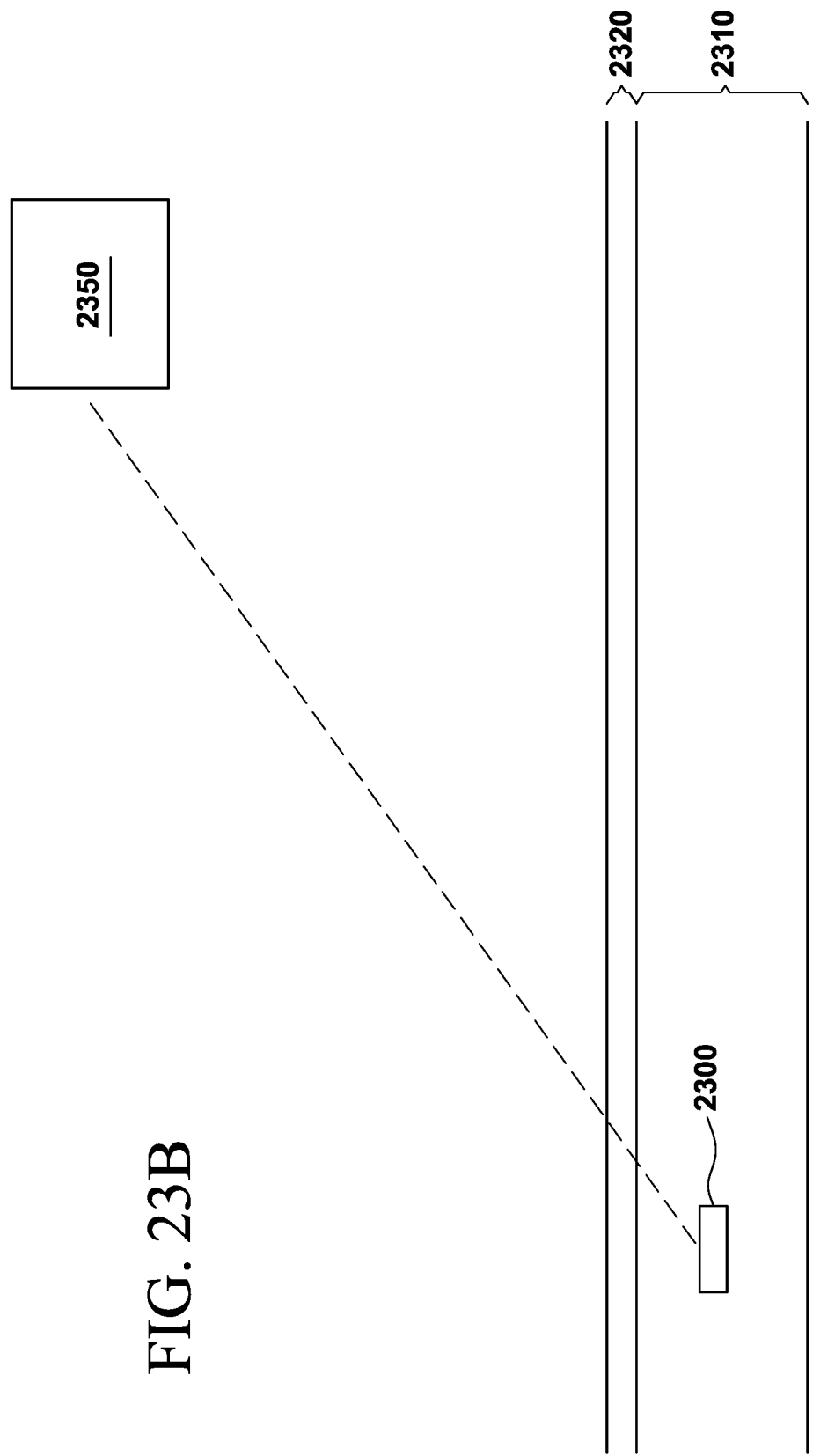
FIG. 23B shows a concrete structure in accordance with an embodiment.

FIG. 23B shows the construction of a concrete floor in accordance with an embodiment. Concrete layer 2310 is laid down. Sensor 2300 is embedded in the concrete. Sensor 2300 may be similar to sensor 100 of FIG. 1 and FIG. 2, for example. A layer 2320 of a selected material is laid down on top of the concrete layer 2310. For example layer 2320 may include rubber or another material.

At step 2340, the sensor obtains measurement data of one or more selected characteristics of the concrete. In the illustrative embodiment, sensor 2300 obtains measurement data pertaining to one or more characteristics of the concrete in layer 2310. For example, sensor 2300 may obtain data pertaining to temperature, humidity, salinity, pH levels, sonic signals, conductivity, etc. At step 2350, the sensor transmits the measurement data. Sensor 2300 transmits the measurement data wirelessly. At step 2360, a second device receives the measurement data from the sensor. In the illustrative embodiment, a second device 2350 receives the measurement data. As discussed elsewhere herein, the measurement data may be used to predict one or more characteristics of the concrete in layer 2310.

The inventors have observed that use of sensor devices, such as sensor 100 of FIG. 1 and FIG. 2, to obtain data relating to a concrete mixture is sometimes complicated by the difficulty of determining when to activate the sensor device (i.e., when to activate the various sensors of the sensor device so that the sensors begin to generate data pertaining to characteristics of the concrete and transmit the measurement data) and the further difficulty of actually activating the sensor device at a desired time. On the one hand, it is undesirable to activate the sensor device before the sensor device has been embedded in the concrete. On the other hand, it is undesirable to activate the sensor device long after the sensor device has been embedded in the concrete. Ideally, the sensor device should be activated at the moment the sensor device is embedded in the concrete mixture.

The inventors have further observed that a sensor device typically experiences a spike in humidity when first embedded in a concrete mixture. The humidity within a concrete mixture is typically significantly higher than the humidity of the outside environment. The inventors have determined that this difference can be utilized to determine when to activate a sensor device.

Thus, in accordance with an embodiment, a sensor device includes a housing and a plurality of sensors disposed in the housing. The plurality of sensors include a humidity sensor and one or more second sensors adapted to obtain measurements of selected characteristics of a concrete mixture, such as temperature, salinity, pH levels, sonic signals, motion, elevation, acceleration, conductivity, etc. For example, the plurality of sensors may include one or more of the following: a temperature sensor, a salinity sensor, a conductivity sensor, a motion sensor, a pH sensor, an acceleration sensor, a sonic sensor, etc. The housing includes an opening adapted to permit humidity to enter the housing but prevent liquid (and concrete) from entering the housing. The opening may be a hole in the housing, for example. For example, the dimensions of the hole may be sufficiently small so that the surface tension of water prevents water and concrete from passing through the hole. For example, the hole may have a width of one millimeter or smaller. The humidity sensor within the sensor device is disposed proximate the hole.

Figure 24A:
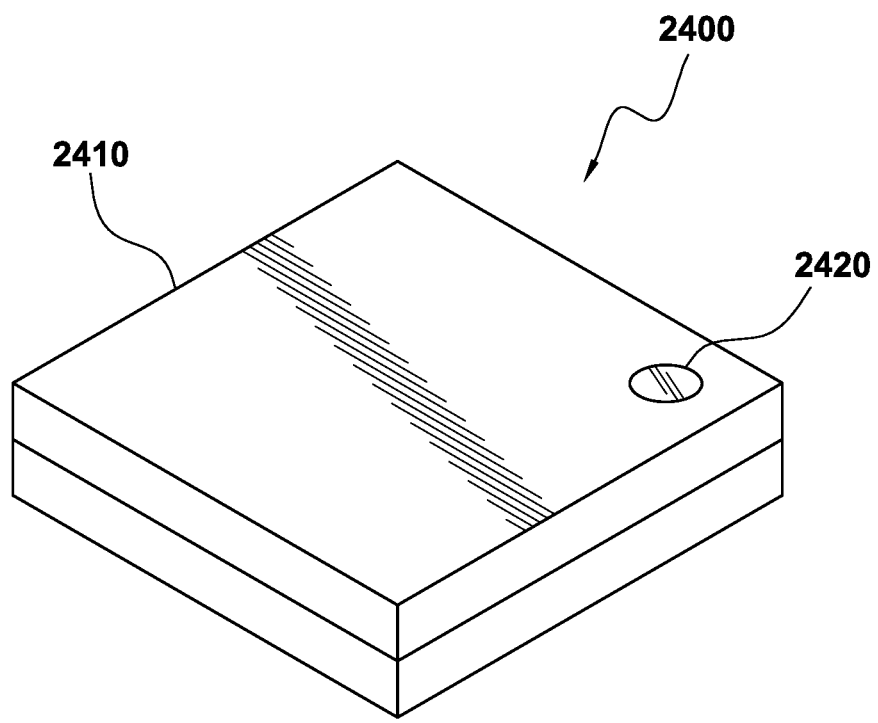
FIG. 24A shows a sensor device in accordance with an embodiment.

FIG. 24A shows a sensor device 2400 in accordance with an embodiment. Sensor device 2400 includes a housing 2410. Housing 2410 includes an opening. In the illustrative embodiment, the opening is a hole 2420. Hole 2420 allows water vapor to pass through; however, the diameter of hole 2420 is sufficiently small so that water and concrete cannot pass through the hole. For example, the hole may have a width of one millimeter or smaller. For example, hole 2420 may have a diameter of between 0.5 millimeters and 1.0 millimeter.

Figure 24B:
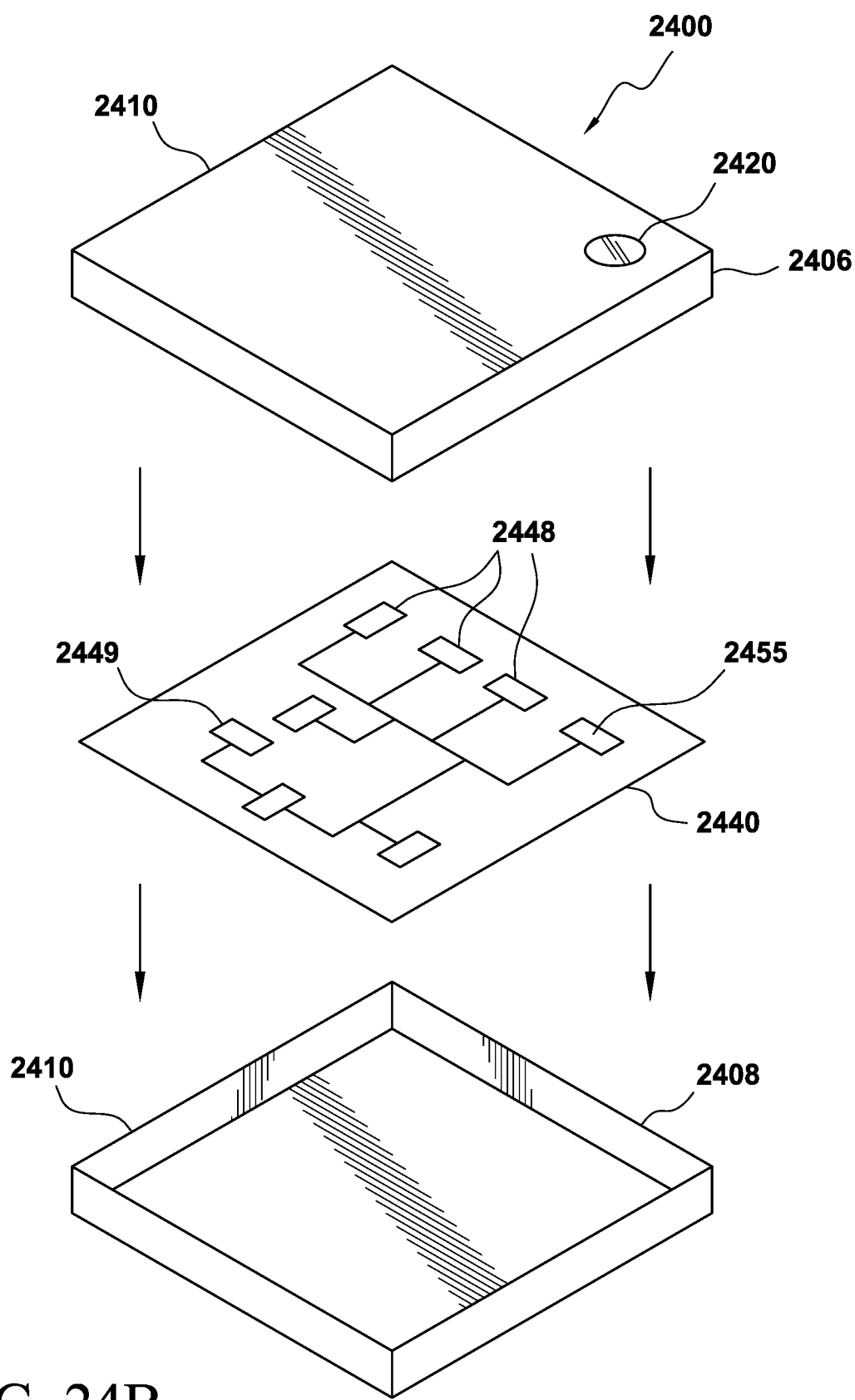
FIG. 24B shows components of a sensor device in accordance with an embodiment.

FIG. 24B shows components of the sensor device of FIG. 2400. Sensor device 2400 includes an upper portion 2406 and a lower portion 2408 of housing 2410. Sensor device 2400 also includes a printed circuit board (PCB) 2440. PCB 2440 includes a plurality of elements 2448, which may include circuit components such as resistors, capacitors, amplifiers, etc., and/or one or more sensors adapted to obtain measurements relating to one or more characteristics such as temperature, salinity, conductivity, motion, etc. For example, PCB 2440 may include one or more of the following: a temperature sensor, a salinity sensor, a conductivity sensor, a motion sensor, a pH sensor, an acceleration sensor, a sonic sensor, etc. In one embodiment, at least one of elements 2448 is a processor adapted to receive measurement data and analyze the measurement data. PCB 2440 also includes a transceiver 2449, which may include an antenna capable of sending and receiving data via wireless communication, for example. In another embodiment, PCB 2440 includes a transmitter. PCB may also include a battery. PCB 2440 also includes a humidity sensor 2455. When housing 2410 is closed, humidity sensor 2455 is located under or proximate hole 2420 such that humidity (water vapor) that enters through hole 2420 is detected by humidity sensor 2455.

PCB 2440 fits into bottom portion 2408. Upper portion 2406 fits onto lower portion 2408, creating a protective seal.

In another embodiment, a sensor device includes a housing that includes an upper portion and a lower portion (such as upper portion 2406 and lower portion 2408). The upper portion and lower portion are adapted to engage and create a partial seal. For example, the upper portion may have first threads that engage with second threads of the lower portion. However, the connection between the upper and lower portions is not a seal. An opening exists between the upper and lower portions that allows water vapor to pass between the exterior and interior of the sensor device but does not allow liquid to pass between the exterior and interior.

Figure 25:
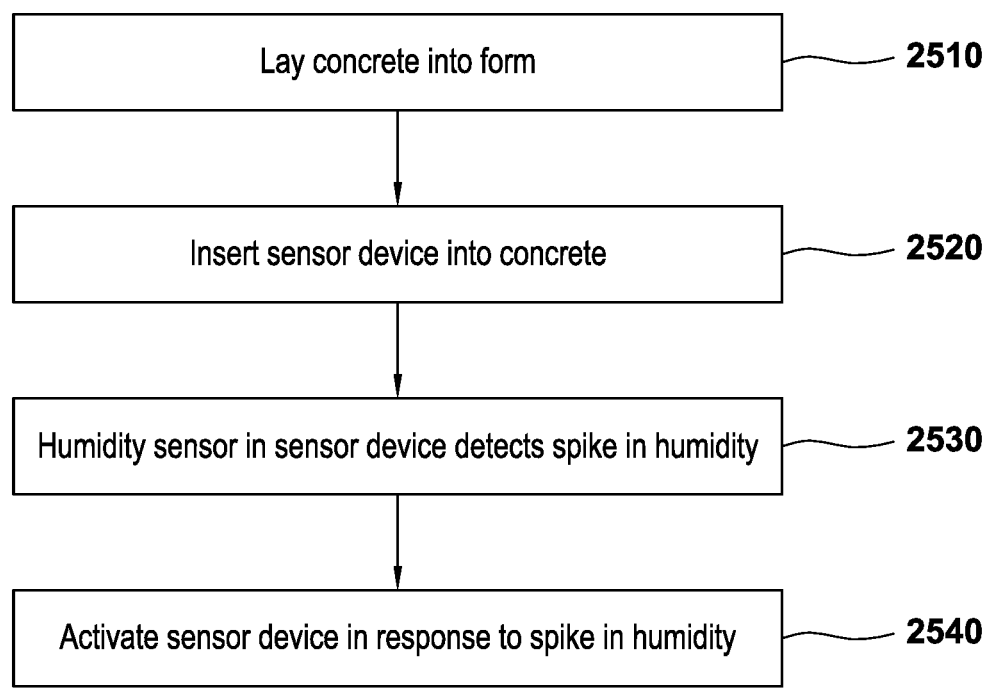
FIG. 25 is a flowchart of a method of detecting humidity in a concrete mixture in accordance with an embodiment.
Figure 26A:
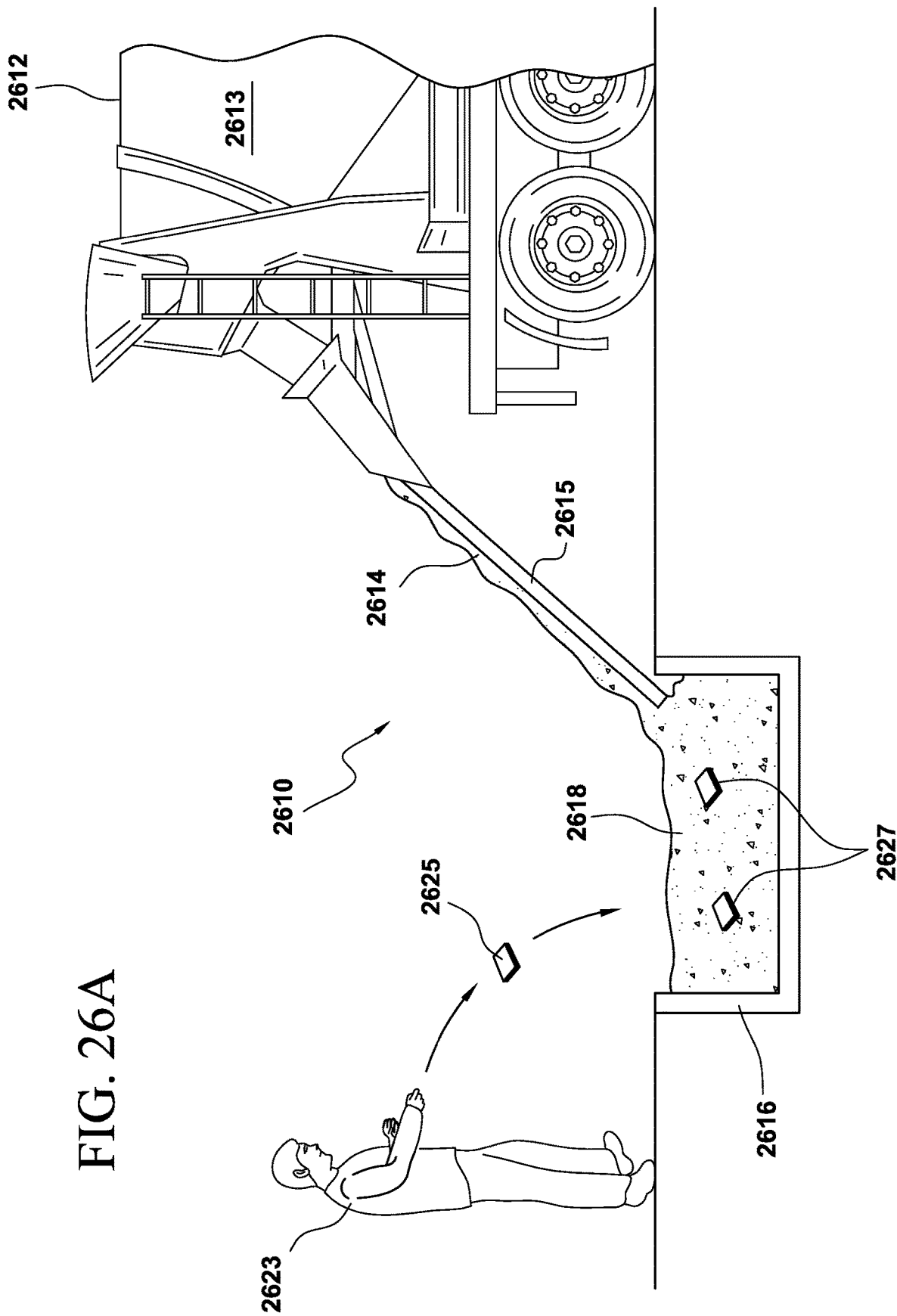
FIG. 26A shows a construction site in accordance with an embodiment.

FIG. 25 is a flowchart of a method of activating a sensor device in accordance with an embodiment. At step 2510, concrete is laid in a form to create a desired structure. FIG. 26A shows a construction site 2610 in accordance with an embodiment. Site 2610 includes a concrete mixing truck 2612 having a drum 2613. Concrete 2614 is poured down a chute 2615 and deposited in a form 2616. The form 2616 thus contains concrete 2618 forming a desired structure.

In the illustrative embodiment, a technician has access to one or more sensor devices that are similar to sensor device 2400 shown in FIG. 24B. Each of these sensor devices is deactivated. When a sensor device is deactivated, any sensors within the sensor device capable of generating data pertaining to various characteristics of concrete (e.g., temperature, salinity, pH, conductivity, etc.) are not activated and do not generate measurement data. The transmitter (e.g., transmitter 2449) within the sensor device does not transmit data. However, even when the sensor device is deactivated, the humidity sensor 2455 continues to function and generates measurements of humidity.

In another embodiment, when a sensor device is deactivated, the transceiver (e.g., transceiver 2449) is active and transmits the humidity measurements generated by humidity sensor 2445 to a remote device (such as data manager 1935). The remote device may be adapted to respond to the humidity measurements and activate the sensor device fully based on the humidity measurements received.

Returning to FIG. 25, at step 2520, a sensor device is inserted into the concrete. In the illustrative embodiment of FIG. 26A, a technician 2623 at the construction site drops or throws a sensor device 2625 into the concrete 2618 in form 2616. For example, sensor device 2625 may be a sensor device similar to sensor device 2400 of FIG. 24B. Prior to the moment when the technician picks up sensor device 2625 and throws it into concrete 2618, the sensor device is deactivated. As seen in FIG. 26A, a plurality of sensor devices 2627 may be inserted into concrete 2618.

Referring to FIG. 24B, before the sensor device 2625 is inserted into the concrete 2618, water vapor enters the sensor device (e.g., through opening or hole 2420). Consequently, the humidity sensor in the sensor device (e.g., humidity sensor 2455 of FIG. 24B) detects a first level of humidity representing the humidity of the surrounding environment.

After sensor device 2625 is inserted (dropped, thrown, etc.) into concrete 2618, water vapor within the concrete enters into sensor device 2625 (through the opening or hole 2420). Consequently, humidity sensor 2455 of sensor device 2625 detects the humidity of the concrete. Typically, the humidity of the concrete is higher than the humidity of the surrounding environment.

Accordingly, at step 2530, a spike in humidity is detected. For example, a processor 2448 on PCB 2440 (in sensor device 2625) may detect a spike in humidity based on predetermined criteria. For example, humidity sensor 2455 may transmit humidity measurements to processor 2448 on PCB 2440, and the processor 2448 may determine that the humidity has experienced a spike defined as a change from a first predetermined level to a second predetermined level; alternatively a spike in humidity may be defined as any change in humidity that exceeds a predetermined amount. Other methods may be used to detect a spike in humidity.

Figure 26B:
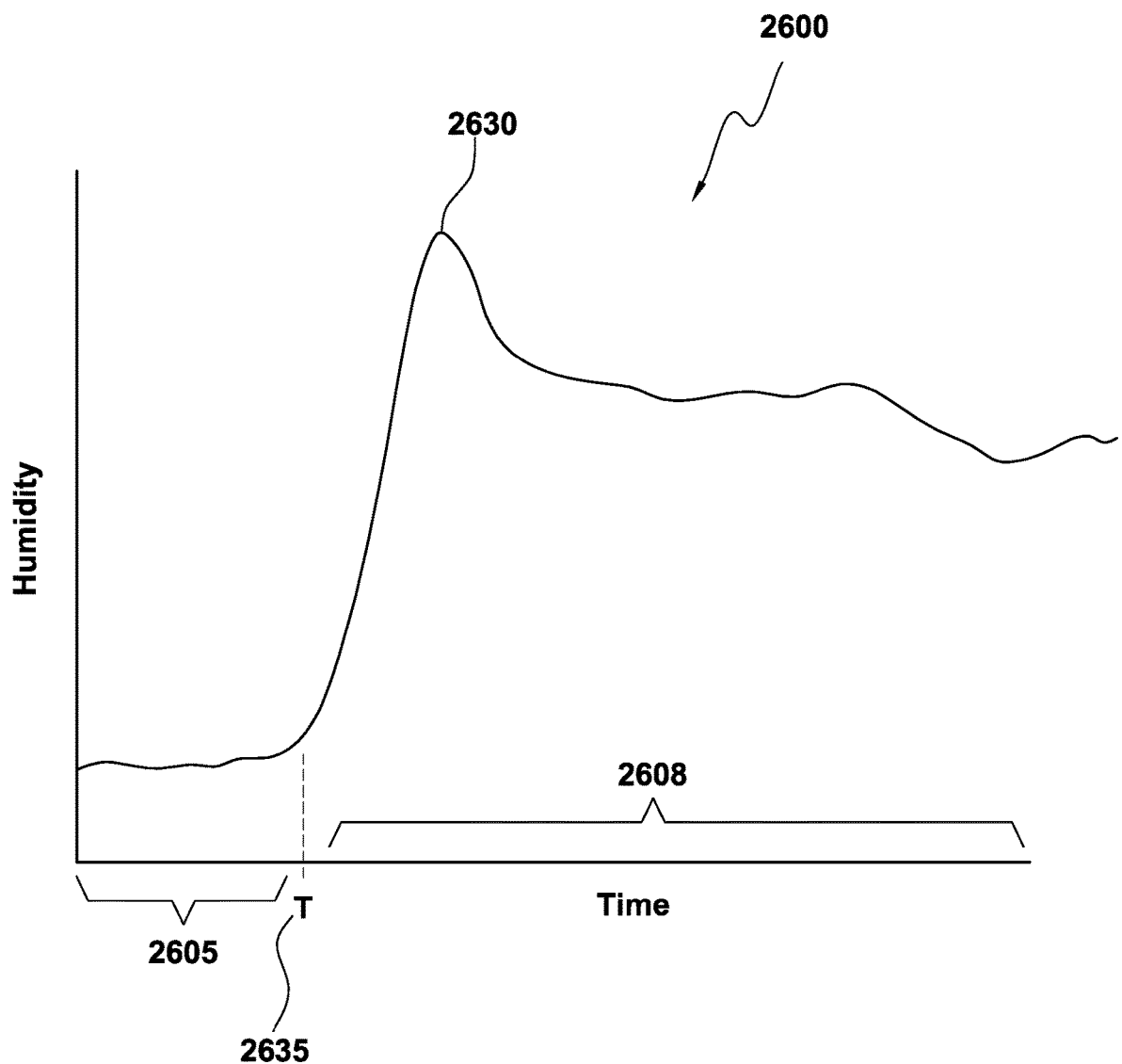
FIG. 26B is a graph showing humidity measurements versus time in accordance with an embodiment.

FIG. 26B shows a graph illustrating humidity measurements obtained by a sensor device in accordance with an embodiment. Specifically, graph 2600 shows humidity measurements obtained by sensor device 2625 versus time. Referring to graph 2600, region 2605 represents the time before the sensor device is inserted into the concrete mixture. During this time, the humidity sensor 2455 detects the humidity of the surrounding environment, which has a first level of humidity (which may vary slightly). At the moment the sensor device is inserted into concrete 2618, the humidity (water vapor) of the concrete enters opening 2420 and is detected by humidity sensor 2455. Because the humidity of concrete 2618 is significantly higher than the humidity of the surrounding air, humidity sensor 2455 detects a spike in humidity when it is inserted into concrete 2618. As a result, the humidity measurements rise to a peak 2630 and then decrease slightly to a second level that is significantly higher than those associated with region 2605. The region 2608 represents the time after the sensor device was inserted into the concrete mixture.

In one embodiment, a time associated with the spike in humidity detected by the sensor device may be determined based on the humidity measurements. This determined time may be used as time zero (T=0) to represent the moment when the sensor device was inserted into the concrete mixture. Mathematical methods of determining a starting time for a significant change in humidity measurements are known. For example, the data may be analyzed and an inflection point in the data may be determined. Alternatively, a curve associated with the humidity measurements may be examined and a point at which the slope of the curve exceeds a predetermined level may be selected as time zero. Other methods may be used. In the illustrative embodiment of FIG. 26B, a time T (2635) is determined based on the spike in the humidity measurements.

Referring again to FIG. 25, at step 2540, the sensor device is activated in response to the spike in the humidity measurements. In the illustrative embodiment, processor 2448 on PCB 2440 activates the sensor device by activating other sensors and components on PCB 2440 in response to the detection of the humidity spike. In another embodiment, a remote device, such as data manager 1935 (communicating with the sensor device via the Internet), may activate the sensor device.

Thus, the sensor device 2625 is activated when humidity sensor 2455 detects the spike in humidity. Specifically, other components and sensors of the sensor device are activated. For example, other sensors (such as sensors capable of detecting temperature, salinity, pH, conductivity, etc.) are activated and begin to measure various characteristics of the concrete mixture. Transceiver 2449 begins to transmit the measurement data.

The inventors have further observed that a sonic signal detected by a sensor device typically experiences a drop in magnitude when the sensor device is first inserted into a wet concrete mixture. Sonic signals (sound waves) typically travel more easily through air than through wet concrete. Thus, if a sensor begins in the surrounding air (e.g., the sensor is held by a technician) and then is inserted into a wet concrete mixture, any sonic sensor on the sensor device that is monitoring sonic signals typically experiences signal loss starting at the moment the sensor device is inserted into the wet concrete mixture. The inventors have determined that this signal loss can be utilized to determine when to activate a sensor device.

Figure 26C:
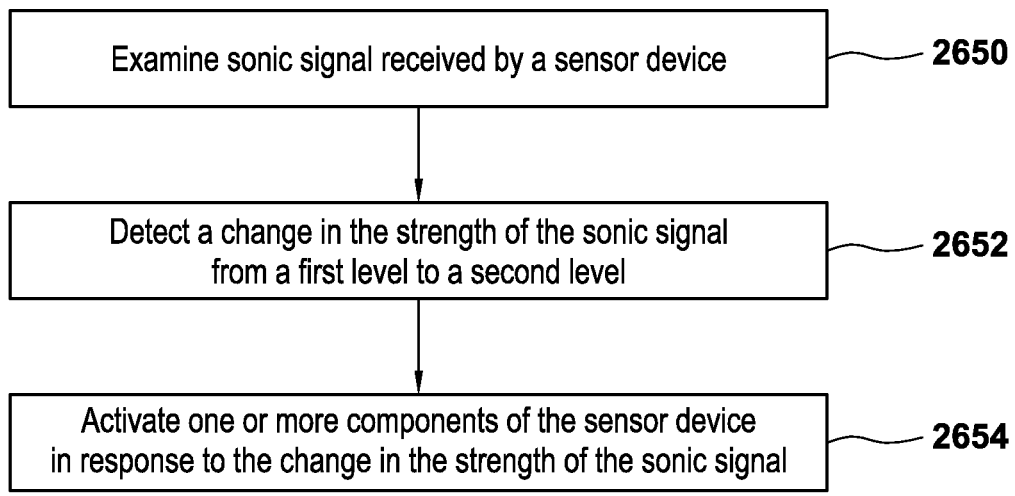
FIG. 26C is a flowchart of a method in accordance with an embodiment.

FIG. 26C is a flowchart showing a method of activating components of a sensor device in accordance with another embodiment. At step 2650, a sonic signal (e.g., a sound wave) received by a sensor device is examined. Referring again to the illustrative embodiment of FIG. 26A, suppose that sensor device 2625 includes a sonic sensor adapted to detect sonic signals (sound waves). A processor of sensor device 2625 monitors and analyzes the sonic signals received. For example, sensor device 2625 may include elements similar to elements 2448 on PCB 2440; the elements may include a sonic sensor and a processor. Alternatively, the sonic signals detected may be transmitted wirelessly to a remote processor adapted to analyze the sonic signals.

FIG. 26D shows a graph 2670 of a sonic signal 2675 that may be detected by a sonic sensor on a sensor device in accordance with an embodiment. In the illustrative embodiment, the sonic sensor begins to detect sonic signals at time T0. The sensor device is held by a technician at time T0 until about time T1. During the period P1 between time T0 and time T1, the sonic signal 2675 has a magnitude (in decibels) around a first initial level, reflecting the sonic signals (including background noise, talking, and any other noises) in the air surrounding the technician.

Suppose now that the technician inserts the sensor device into a concrete mixture at about time T1. At step 2652, a change in the strength of the sonic signal (sound wave) from a first level to a second level is detected. Specifically, after the sensor is embedded in the concrete mixture, the sonic signal detected by the sonic sensor on the sensor device decreases in strength. Thus, referring to graph 2670, the strength of the sonic signal 2675 decreases after time T1 (associated with point 2683) to a second level. The sonic signal displays a signal strength having a second level (which is lower than the first level) between approximately T1 and approximately time T2. The processor of the sensor device 2625 determines that a decrease in the strength of the sonic signal has been detected.

At step 2654, one or more components of the sensor device are activated in response to the change in the strength of the sonic signal. In response to the determination that the strength of the sonic signal has decreased from the first level to the second level, one or more components of the sensor device 2625 are activated. For example, one or more of a temperature sensor, a humidity sensor, a salinity sensor, an accelerometer, a pH sensor, a conductivity sensor, etc., on sensor device 2625 may be activated.

As the concrete mixture dries, the properties of the concrete mixture may change; for example, the dry concrete mixture may transmit sound signals more easily than the wet concrete. As a result, the sonic sensor on the sensor device 2625 may detect an increase in the strength of the sonic signals as the concrete sets. In the illustrative embodiment of FIG. 26D, the strength of sonic signal 2675 increases starting at about time T2 (associated with point 2696 on graph 2670). The strength of sonic signal 2675 rises to a third level (different from the second level). One or more components of the sensor device 2625 may be activated based on the detection of the signal from the second level to the third level.

Figure 27A:
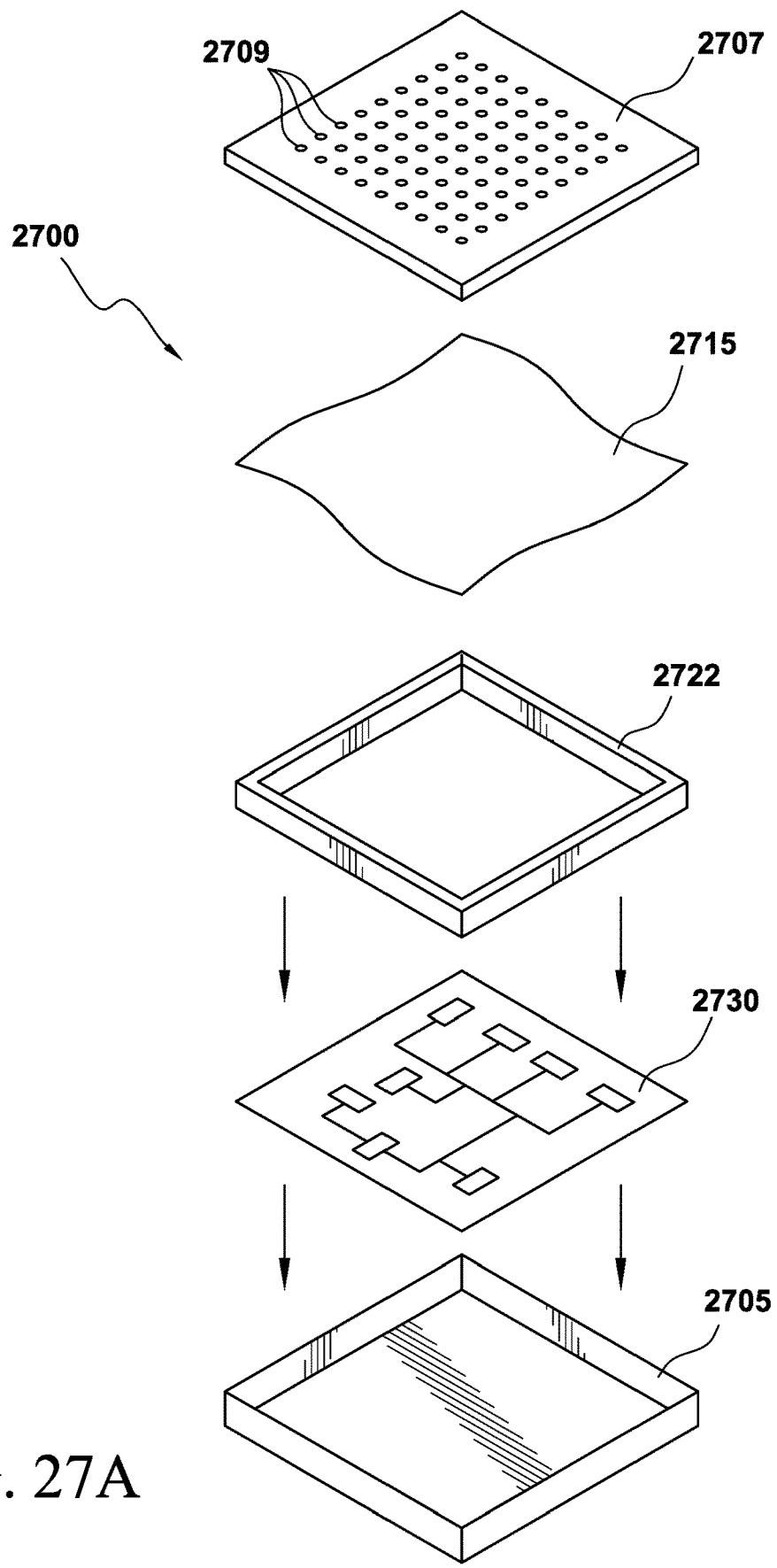
FIGS. 27A-27C show components of a sensor device in accordance with another embodiment.
Figure 27B:
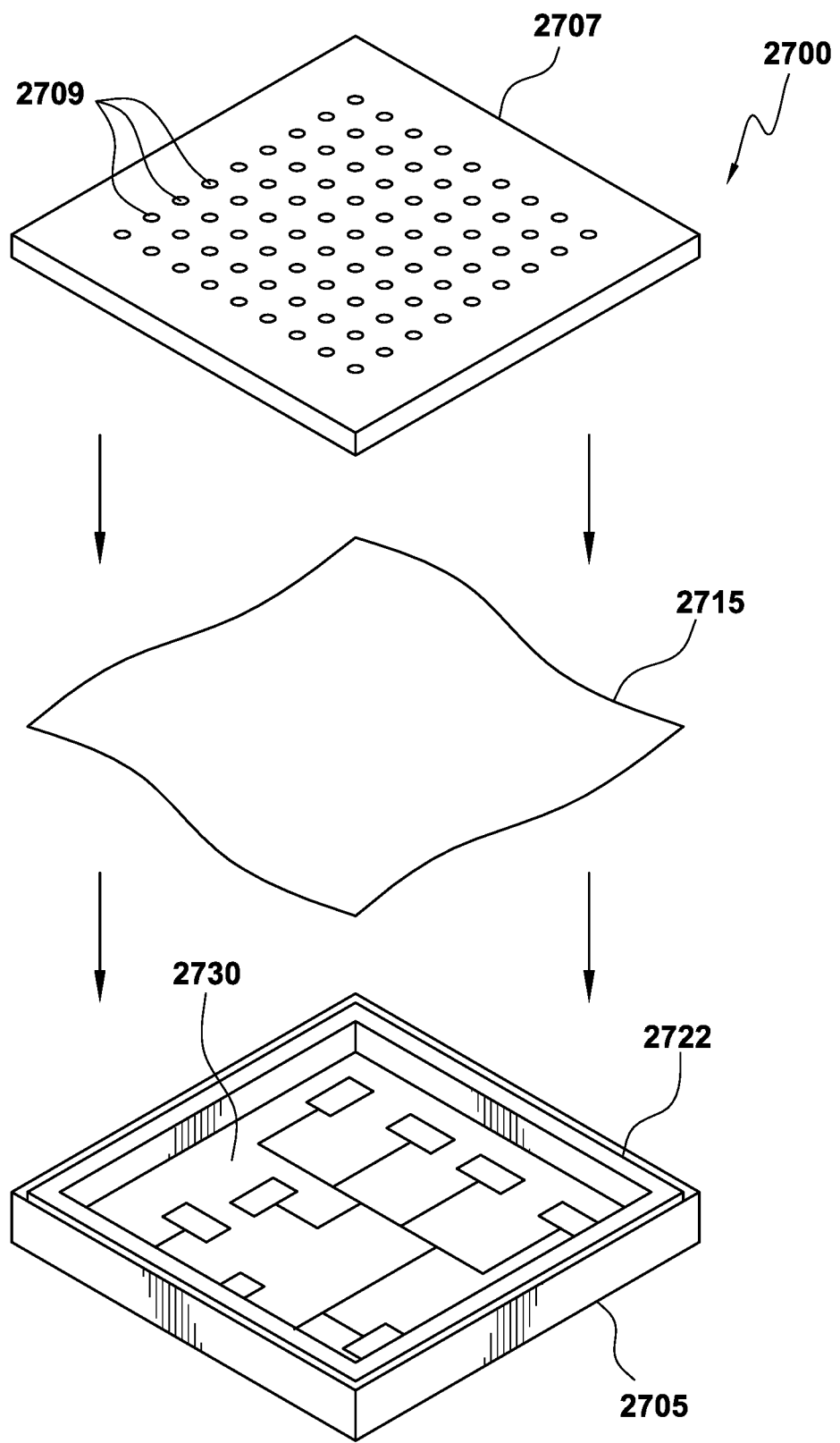
Figure 27C:
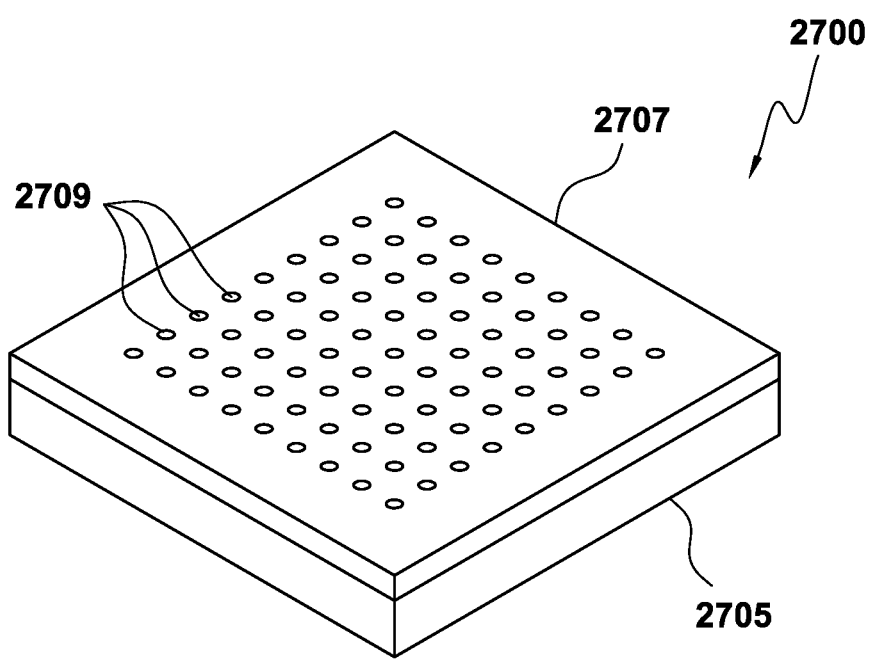

FIGS. 27A-27C show components of a sensor device in accordance with another embodiment. As shown in FIG. 27A, sensor device 2700 includes a housing that includes an upper portion 2707 and a lower portion 2705. Upper portion 2707 and lower portion 2705 may be formed from plastic, metal, or other material. Sensor device 2700 also includes a waterproof layer 2715, a support 2722, and a sensor component 2730.

Upper portion 2707 of housing includes a plurality of holes 2709. In the illustrative embodiment of FIG. 27A, upper portion 2707 includes seventy-two holes arranged in an 8×9 array. In other embodiments, upper portion 2707 of the housing may include any number of holes arranged in any configuration.

Each hole may be any size. For example, each hole may between 0.5 and 6.0 millimeters wide. The holes are adapted to allow humidity to pass through from the exterior of sensor device 2700 to the interior of the sensor device. In some embodiments, the holes may allow liquid and/or concrete to pass through. In other embodiments, the holes do not allow liquid or concrete to pass through.

Waterproof layer 2715 is made of a waterproof, breathable material that allows humidity (water vapor) to pass through the layer but does not allow liquid or concrete to pass through. For example, waterproof layer 2715 may be made waterproof, breathable fabric membrane such as Gore-Tex or other similar material.

Sensor component 2730 includes one or more sensors adapted to measure one or more characteristics of a surrounding material (such as concrete, water, etc.) Sensor component 2730 may be, for example, a printed circuit board (PCB) containing circuit components such as resistors, capacitors, amplifiers, etc., and/or one or more sensors adapted to obtain measurements relating to one or more characteristics such as temperature, humidity, salinity, conductivity, motion, etc. Sensor component 2730 may also include a processor. Sensor component 2730 may also include a transceiver, or may include a transmitter and a receiver. Sensor component 2730 may also include a battery. Alternatively, a battery or other power source may be disposed elsewhere in sensor device 2700.

Support 2722 is disposed between sensor component 2730 and waterproof layer 2715. Support 2722 separates waterproof layer 2715 from sensor component 2730 and thereby protects the sensors (and other electronics) of sensor component 2730 from water, liquids, concrete, etc. that may be proximate waterproof layer 2715. Thus support 2722 may maintain a predetermined distance between waterproof layer 2715 and sensor component 2730.

In the illustrative embodiment, sensor device 2700 is assembled by fitting sensor component 2730 into lower portion 2705 of the housing, and placing support 2722 above sensor component 2730, as illustrated in FIGS. 27A and 27B. Waterproof layer 2715 is placed above support 2722, and upper portion 2707 is fitted over lower portion 2705, as illustrated in FIGS. 27B and 27C. Upper portion 2707 and lower portion 2705 may form a seal when fitted together. FIG. 27C shows sensor device 2700 in a fully assembled state.

Figure 28:
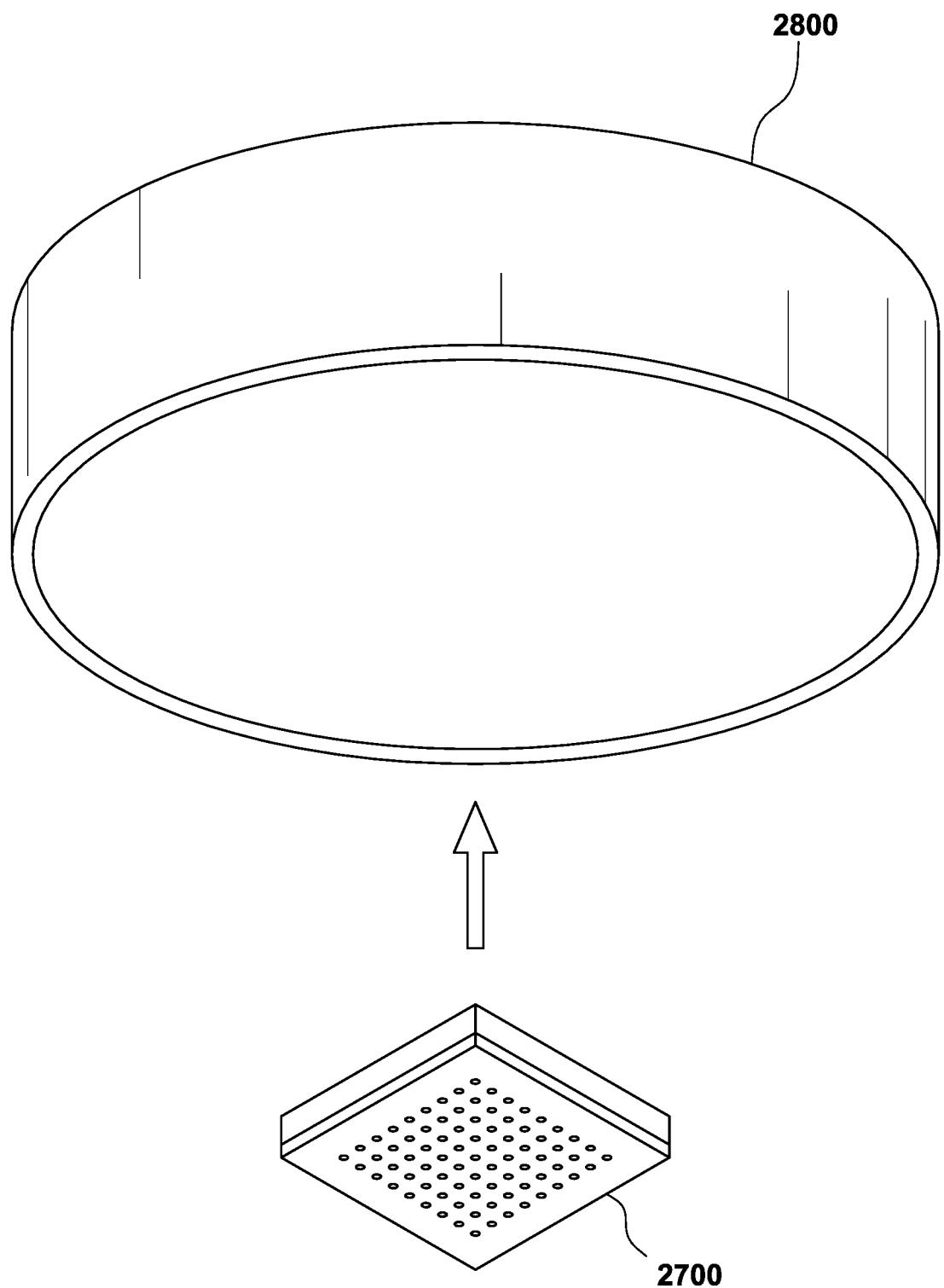
FIG. 28 shows a sensor device and a cap adapted to be placed onto a standard concrete test cylinder in accordance with an embodiment.

In accordance with an embodiment, sensor device 2700 may be attached to a cap adapted to fit onto a standard concrete test cylinder. FIG. 28 shows sensor device 2700 and a cap 2800 adapted to be placed onto a standard concrete test cylinder. For example, sensor device 2700 may be attached to an interior surface of cap 2800 in the manner shown in FIG. 12. In the manner described herein, sensor device 2700 may then obtain measurements relating to one or more characteristics of the concrete mixture in the test cylinder. Sensor device 2700 may transmit the measurement data wirelessly.

It has been observed that certain components of a sensor device such as those described herein can sometimes suffer damage if the sensor device is dropped, thrown, or otherwise experiences a rapid or jarring movement. In particular, it has been observed that if a sensor device is thrown or dropped into a concrete mixture at a construction site, the battery within the sensor device may be damaged by the associated rapid movements. Therefore, a need exists for a sensor device design that protects a battery from rapid, jarring movements that may occur when the sensor device is thrown, dropped, etc.

Figure 29A:
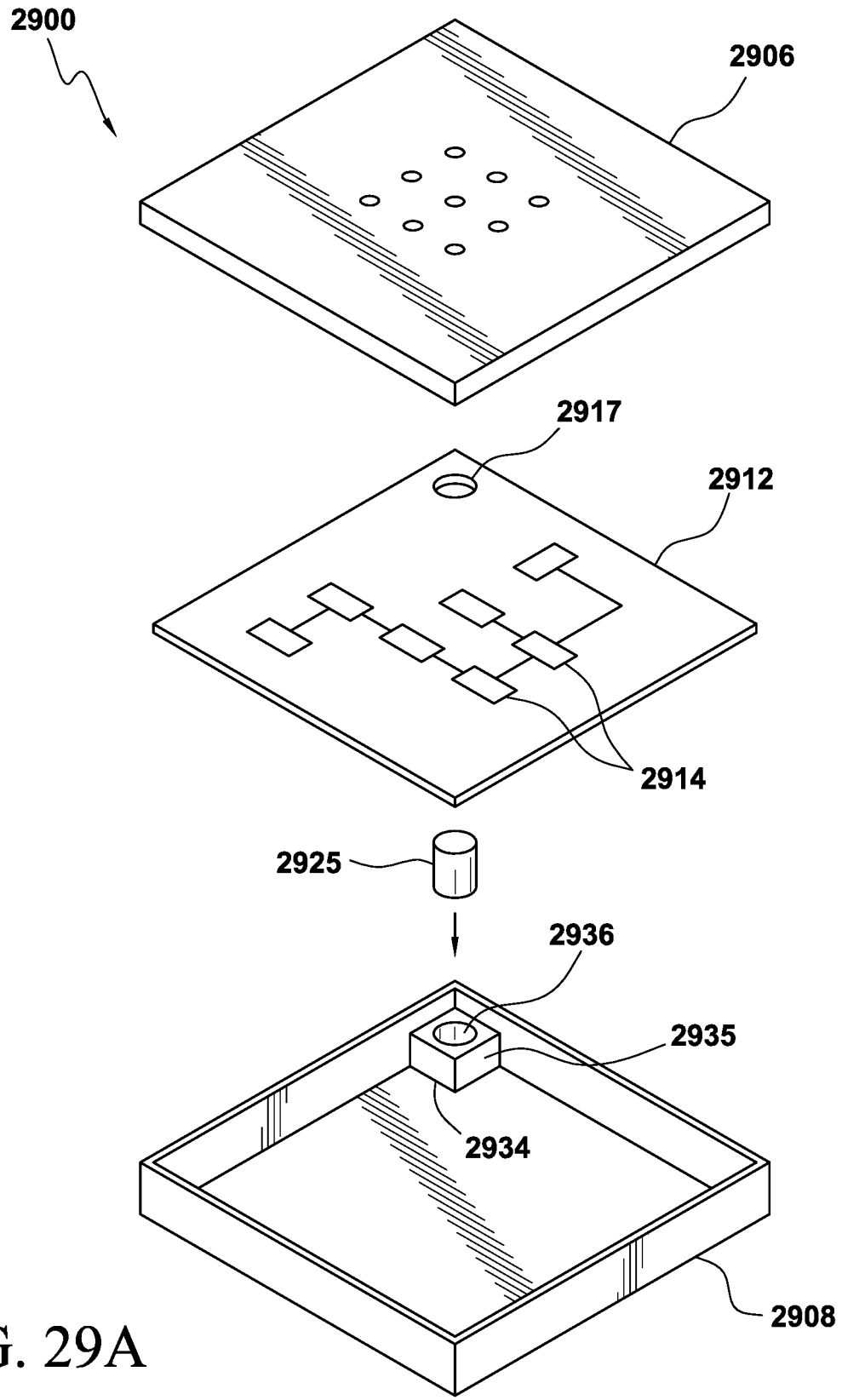
FIGS. 29A-29D show a sensor device in accordance with another embodiment.

FIGS. 29A-29D show a sensor device in accordance with another embodiment. FIG. 29A shows components of a sensor device 2900. Sensor device 2900 includes a housing that includes an upper portion 2906 and a lower portion 2908. Upper portion 2906 may include one or more holes that allow water vapor (but not liquid or concrete) to pass through. Sensor device 2900 also includes a sensor component 2912 which includes one or more sensors. For example, sensor component 2912 may be, for example, a printed circuit board (PCB) containing circuit components such as resistors, capacitors, amplifiers, etc., and/or one or more sensors 2914 adapted to obtain measurements relating to one or more characteristics such as temperature, salinity, conductivity, motion, etc. For example, the sensor component 2912 may include one or more of the following: a temperature sensor, an accelerometer, a pH sensor, an inductance sensor, an impedance or resistivity sensor, a sonic sensor, a pressure sensor, a conductivity sensor, a salinity sensor, a humidity sensor, or an elevation sensor. One example of the temperature sensor is a miniature-sized temperature logger "SMARTBUTTON" (ACR SYSTEMS INC.). In one embodiment, a salinity sensor may include a chloride ion electrode, for example. Sensor component 2912 may also include a transceiver, or may include a transmitter and a receiver.

Sensor component 2917 also includes a hole 2917 in a selected location. In the illustrative embodiment of FIGS. 29A-29D, hole 2917 is proximate a corner of sensor component 2912; however, in other embodiments, hole 2917 may be at a different location on sensor component 2912.

Sensor device 2900 also includes a battery 2925 adapted to provide power to various sensors and other electronic elements of sensor component 2912.

Hole 2917 of sensor component 2912 is adapted to receive battery 2925. Preferably, the size and shape of hole 2917 are selected such that battery 2925 fits snugly through hole 2917 with little or no space between the battery and the edge of the hole.

Lower portion 2908 of the housing includes a casing 2934 disposed in a selected location. While in the illustrative embodiment, casing 2934 is disposed in a corner of the lower portion 2908, in other embodiments, casing 2934 may be located at any selected location of the housing. Casing 2934 includes a solid peripheral portion 2935 and a central cavity 2936. Cavity 2936 is adapted to receive and hold at least a portion of battery 2925. Preferably, the size and shape of cavity 2936 are selected such that battery 2925 fits snugly into cavity 2936 with little or no space between the battery and the side of cavity 2936, to ensure that battery 2925 does not move or shake when placed in the cavity.

Figure 29B:
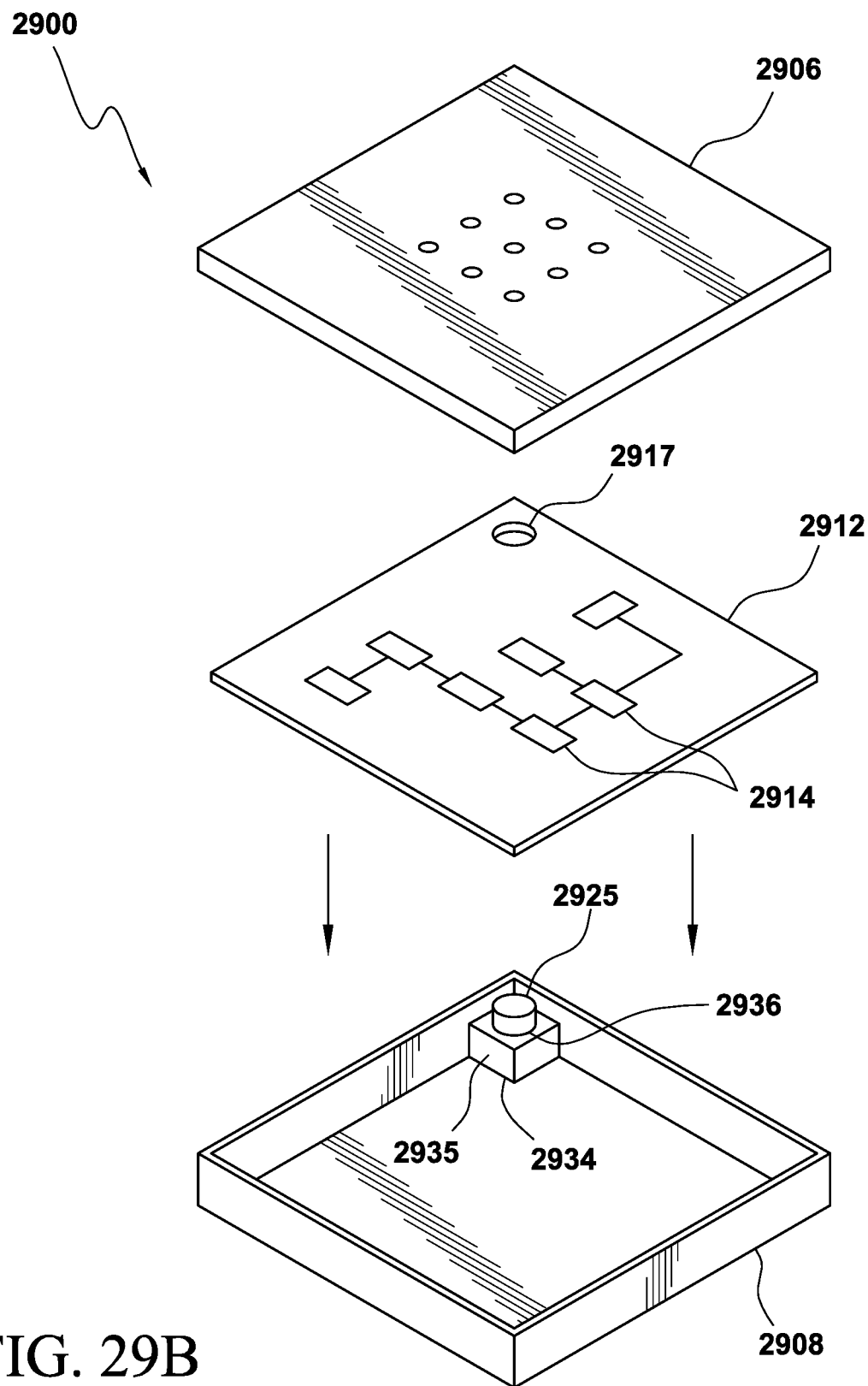
Figure 29C:
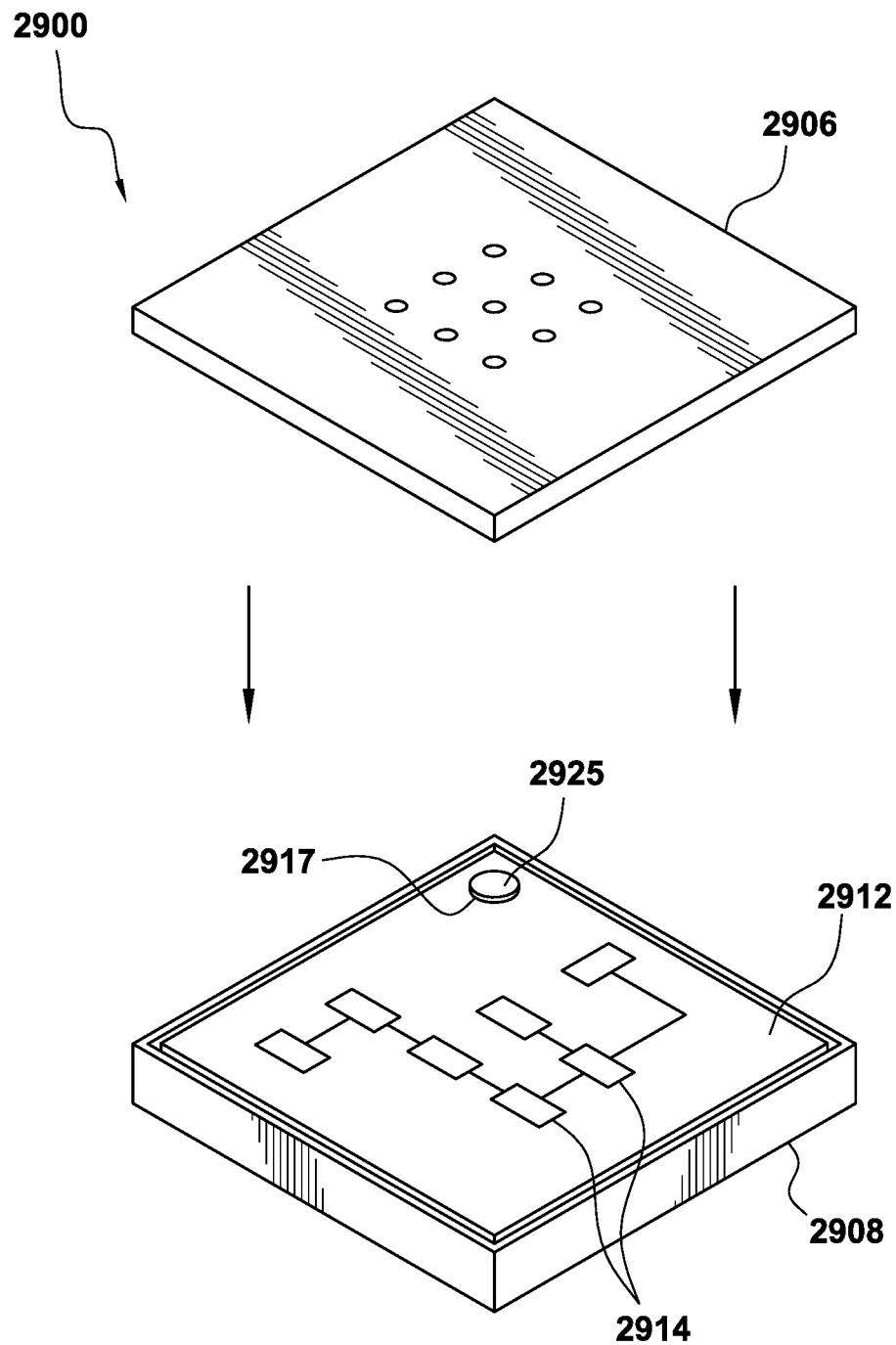
Figure 29D:
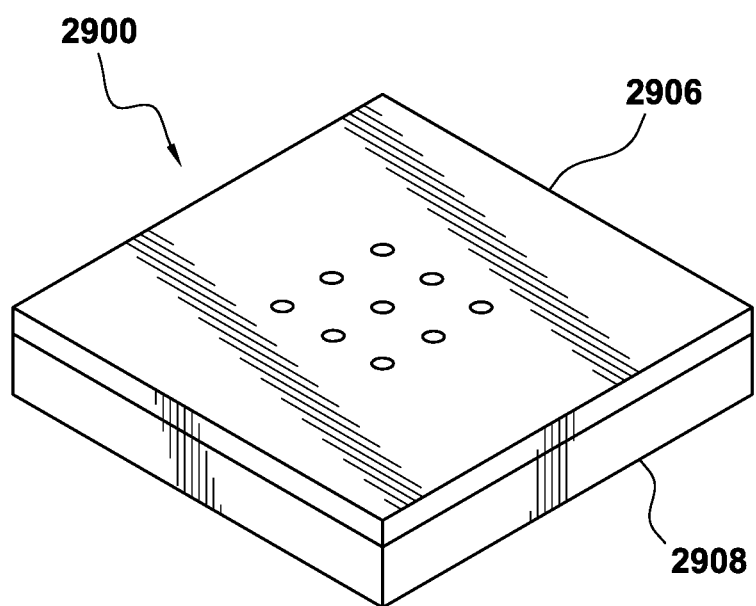

Referring to FIGS. 29B-29D, sensor device 2900 is assembled by placing battery 2925 into cavity 2936. FIG. 29B shows components of sensor device 2900 after battery 2935 has been placed into cavity 2936. Sensor component 2912 is then placed into lower portion 2908 of the housing. Battery 2925 passes through hole 2917, allowing sensor component 2912 to fit into lower portion 2908 of the housing. FIG. 29C shows sensor device 2900 after sensor component 2912 has been placed into lower portion 2908 of the housing. Batter 2925 is visible and may protrude from hole 2917 of sensor component 2912.

Upper portion 2906 of the housing is then secured onto lower portion 2908. Upper portion 2906 and lower portion 2908 may form a seal when fitted together. FIG. 29D shows sensor device 2900 in a fully assembled state.

Advantageously, the placement of battery 2925 within cavity 2936 and hole 2917 secures battery 2925 in place and prevents battery 2925 from moving within sensor device 2900 if sensor device 2900 is moved. This design advantageously protects the battery from being damaged if sensor device 2900 is dropped, thrown, or is otherwise moved in a jarring manner.

Figure 30A:
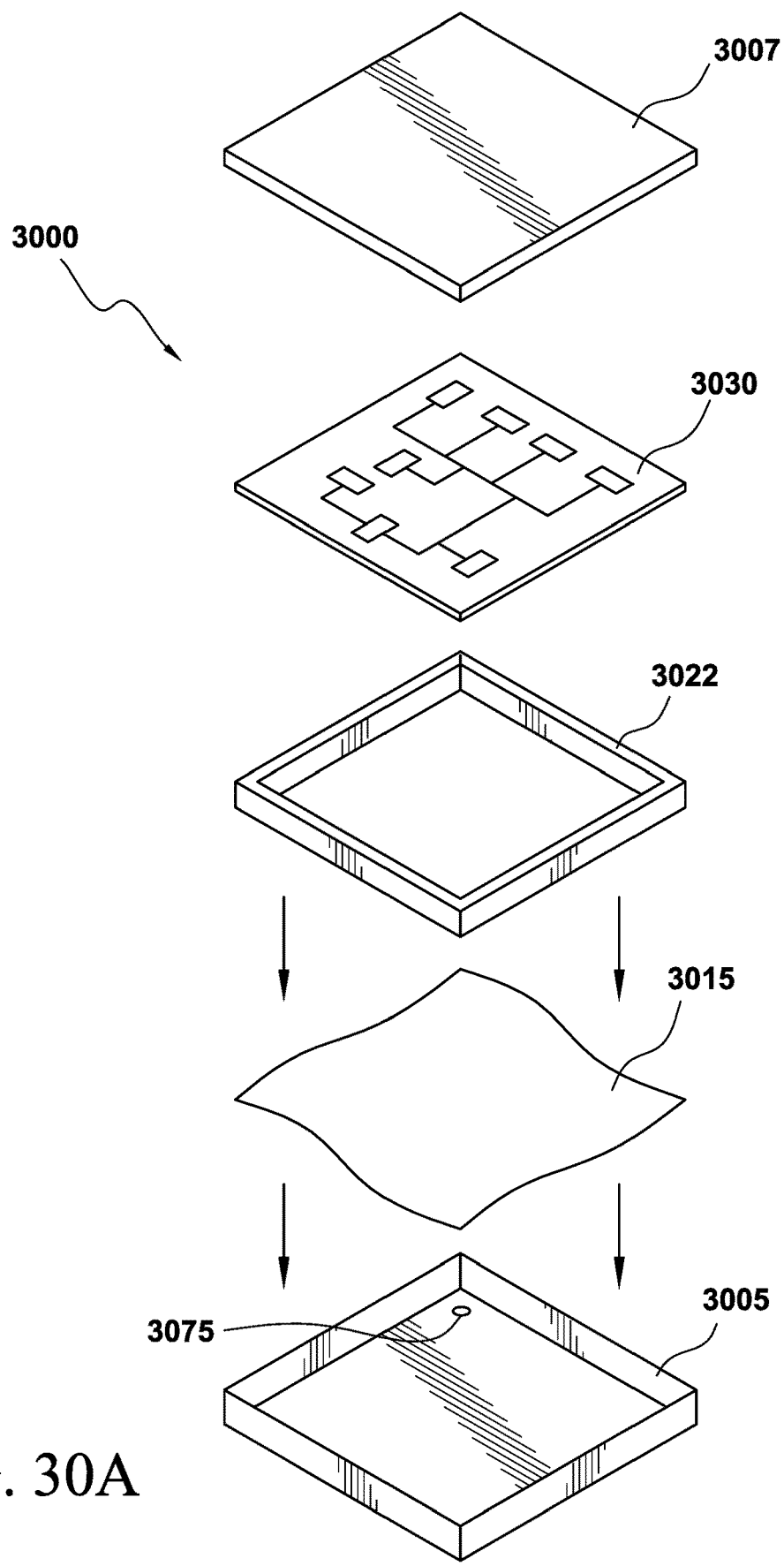
FIGS. 30A-30C show components of a sensor device in accordance with another embodiment.
Figure 30B:
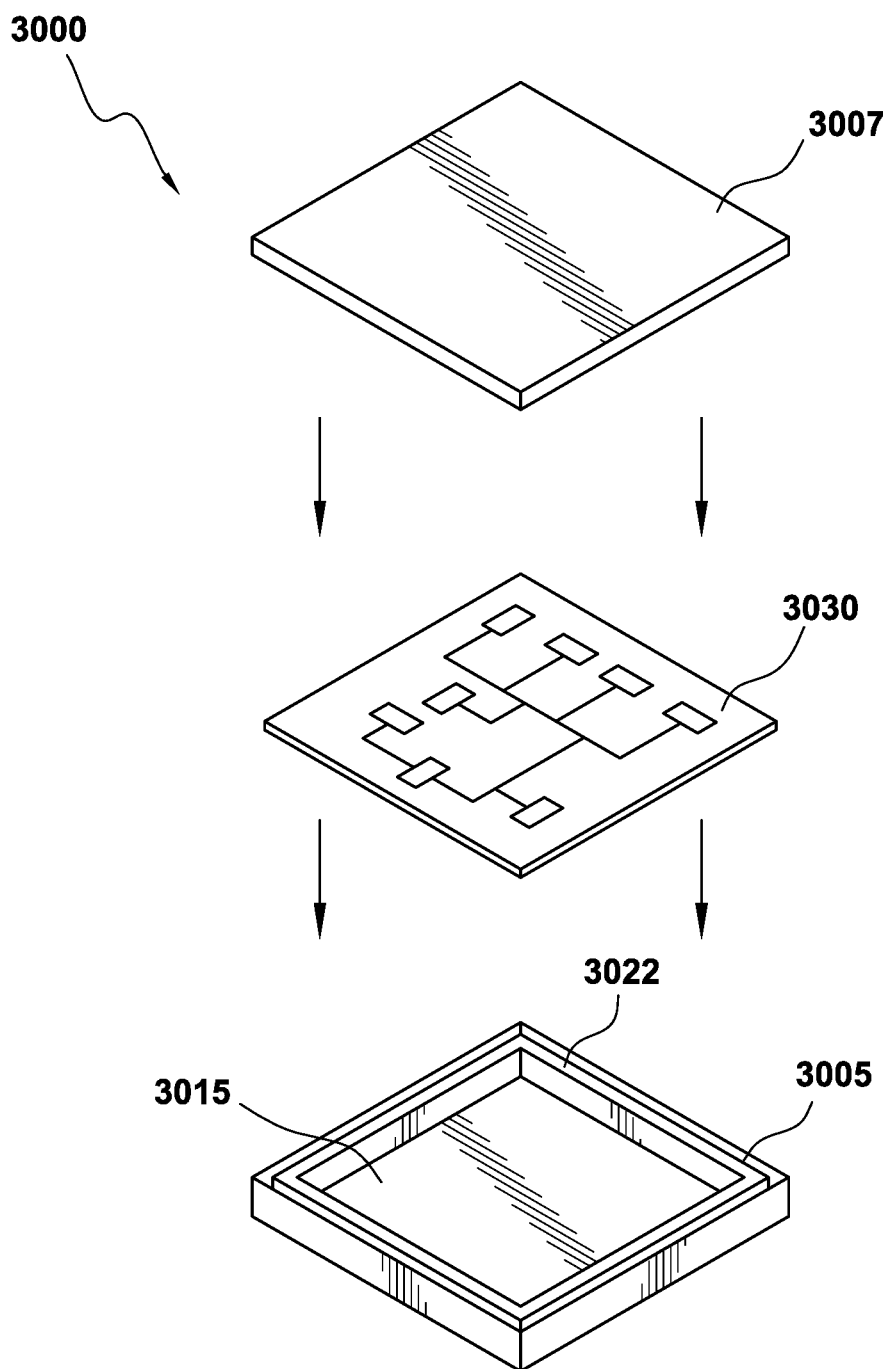
Figure 30C:
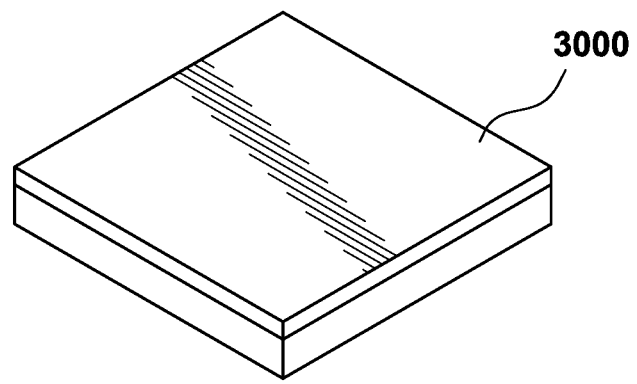

FIGS. 30A-30C show components of a sensor device in accordance with another embodiment. As shown in FIG. 30A, sensor device 3000 includes a housing that includes an upper portion 3007 and a lower portion 3005. Upper portion 3007 and lower portion 3005 may be formed from plastic, metal, or other material. Sensor device 3000 also includes a waterproof layer 3015, a support 3022, and a sensor component 3030.

Upper portion 3007 of housing does not include any holes. Therefore, upper portion 3007 of the housing does not allow humidity to pass through from the exterior of sensor device 3000 to the interior of the sensor device.

Lower portion 3005 includes a single hole 3075 that allows humidity (water vapor) to pass into the interior of sensor device 3000 but does not allow water, concrete, or other liquids to enter. For example, hole 3075 may be a hole having a diameter of between about 1.0 millimeters and 3.0 millimeters, preferably about 2.0 millimeters. Other diameters may be used.

Sensor component 3030 includes one or more sensors adapted to measure one or more characteristics of a surrounding material (such as concrete, water, etc.) Sensor component 3030 may be, for example, a printed circuit board (PCB) containing circuit components such as resistors, capacitors, amplifiers, etc., and/or one or more sensors adapted to obtain measurements relating to one or more characteristics such as temperature, humidity, salinity, conductivity, motion, etc. Sensor component 3030 may also include a processor. Sensor component 3030 may also include a transceiver, or may include a transmitter and a receiver. Sensor component 3030 may also include a battery. Alternatively, a battery or other power source may be disposed elsewhere in sensor device 3000.

Waterproof layer 3015 is made of a waterproof, breathable material that allows humidity (water vapor) to pass through the layer but does not allow liquid or concrete to pass through. For example, waterproof layer 3015 may be made waterproof, breathable fabric membrane such as Gore-Tex or other similar material.

Support 3022 is disposed between sensor component 3030 and waterproof layer 3015. Support 3022 separates waterproof layer 3015 from sensor component 3030 and thereby protects the sensors (and other electronics) of sensor component 3030 from water, liquids, concrete, etc. that may be proximate waterproof layer 3015. Thus support 3022 may maintain a predetermined distance between waterproof layer 3015 and sensor component 3030.

In the illustrative embodiment, sensor device 3000 is assembled by fitting waterproof layer 3015 and support 3022 into lower portion 3005 of the housing, as illustrated in FIGS. 30A-30B. Sensor component 3030 is then placed above support 3022, and upper portion 3007 is fitted over lower portion 3005, as illustrated in FIGS. 30B and 30C. Upper portion 3007 and lower portion 3005 may form a seal when fitted together. FIG. 30C shows sensor device 3000 in a fully assembled state.

Figure 31A:
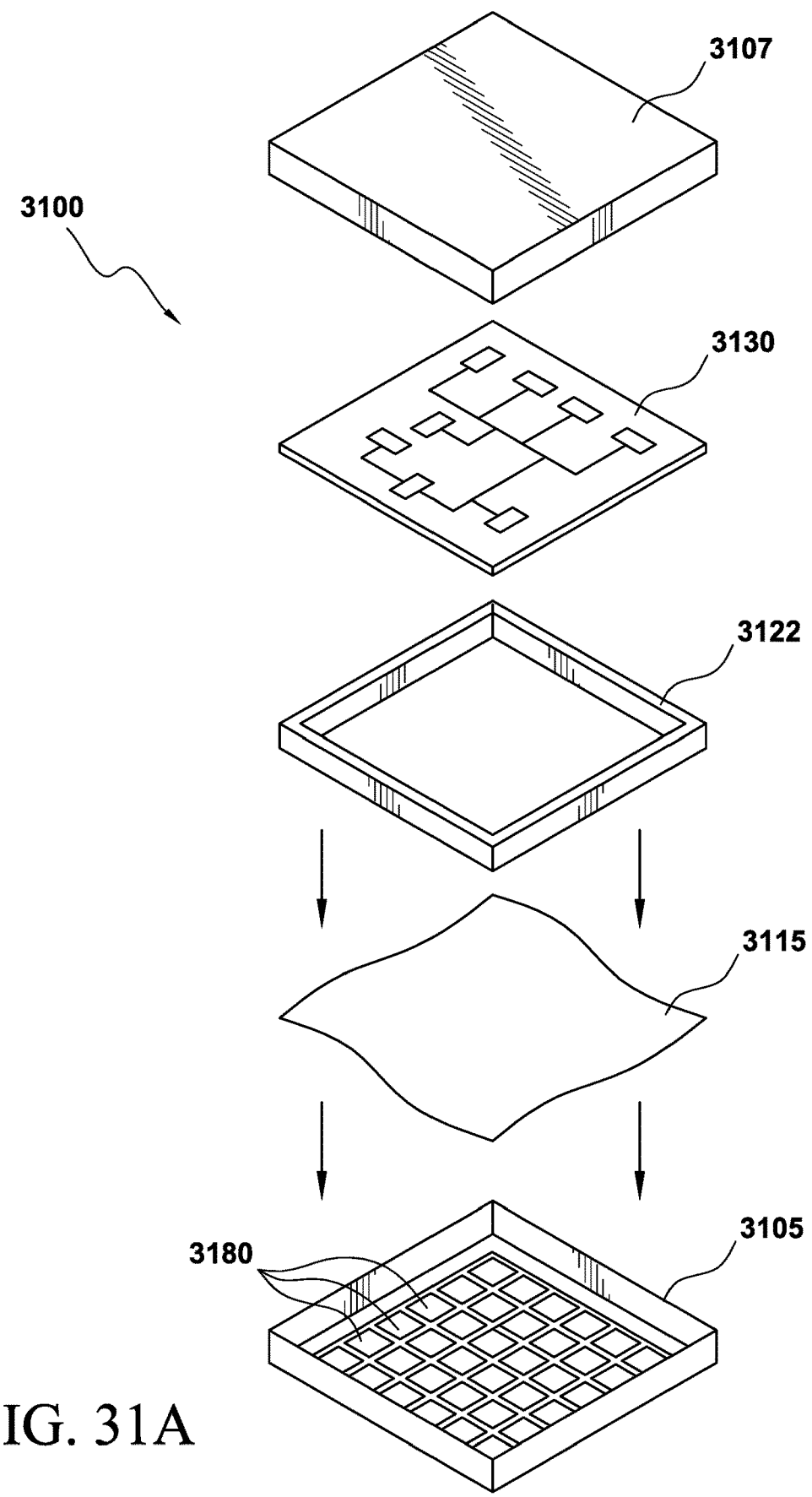
FIGS. 31A-31D show components of a sensor device in accordance with another embodiment.
Figure 31B:
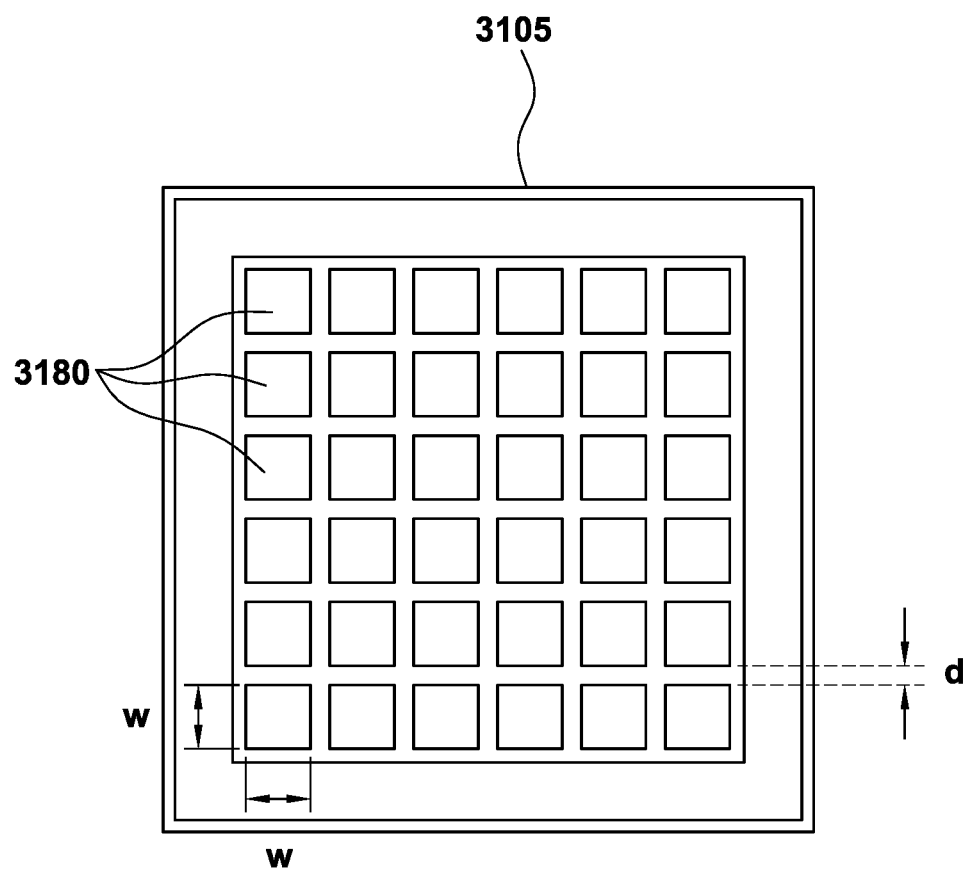

FIGS. 31A-31D show components of a sensor device in accordance with another embodiment. As shown in FIG. 31A, sensor device 3100 includes a housing that includes an upper portion 3107 and a lower portion 3105. Upper portion 3107 and lower portion 3105 may be formed from plastic, metal, or other material. Sensor device 3100 also includes a waterproof layer 3115, a support 3122, and a sensor component 3130.

Upper portion 3107 of housing does not include any holes. Therefore, upper portion 3107 of the housing does not allow humidity to pass through from the exterior of sensor device 3100 to the interior of the sensor device.

Lower portion 3105 includes an array of holes 3180. Holes 3180 allow liquid and humidity (water vapor) to pass into the interior of sensor device 3100. An array of any size may be used. For example, a 5×5 array of holes, a 6×6 array of holes, a 5×6 array of holes, or other configuration may be used. In one embodiment, each hole 3180 may be a square or rectangular hole having sides of length between 5.5 millimeters and 6.5 millimeters, preferably a square hole having sides of length 6.1 millimeters. Other shapes and dimensions may be used. Lower portion 3105 may include an array having holes of uniform shape and size, or may have an array with holes of different shapes and sizes. For example, holes at the corners and around the edges of a 6×5 array may be smaller and/or have shapes that are different from the sizes and shapes of the holes in the center of the array.

Sensor component 3130 includes one or more sensors adapted to measure one or more characteristics of a surrounding material (such as concrete, water, etc.) Sensor component 3130 may be, for example, a printed circuit board (PCB) containing circuit components such as resistors, capacitors, amplifiers, etc., and/or one or more sensors adapted to obtain measurements relating to one or more characteristics such as temperature, humidity, salinity, conductivity, motion, sound, etc. Sensor component 3130 may also include a processor. Sensor component 3130 may also include a transceiver, or may include a transmitter and a receiver. Sensor component 3130 may also include a battery. Alternatively, a battery or other power source may be disposed elsewhere in sensor device 3100.

Waterproof layer 3115 is made of a waterproof, breathable material that allows humidity (water vapor) to pass through the layer but does not allow liquid or concrete to pass through. For example, waterproof layer 3115 may be made waterproof, breathable fabric membrane such as Gore-Tex or other similar material.

Support 3122 is disposed between sensor component 3130 and waterproof layer 3115. Support 3122 separates waterproof layer 3115 from sensor component 3130 and thereby protects the sensors (and other electronics) of sensor component 3130 from water, liquids, concrete, etc. that may be proximate waterproof layer 3115. Thus support 3122 may maintain a predetermined distance between waterproof layer 3115 and sensor component 3130.

Figure 31C:
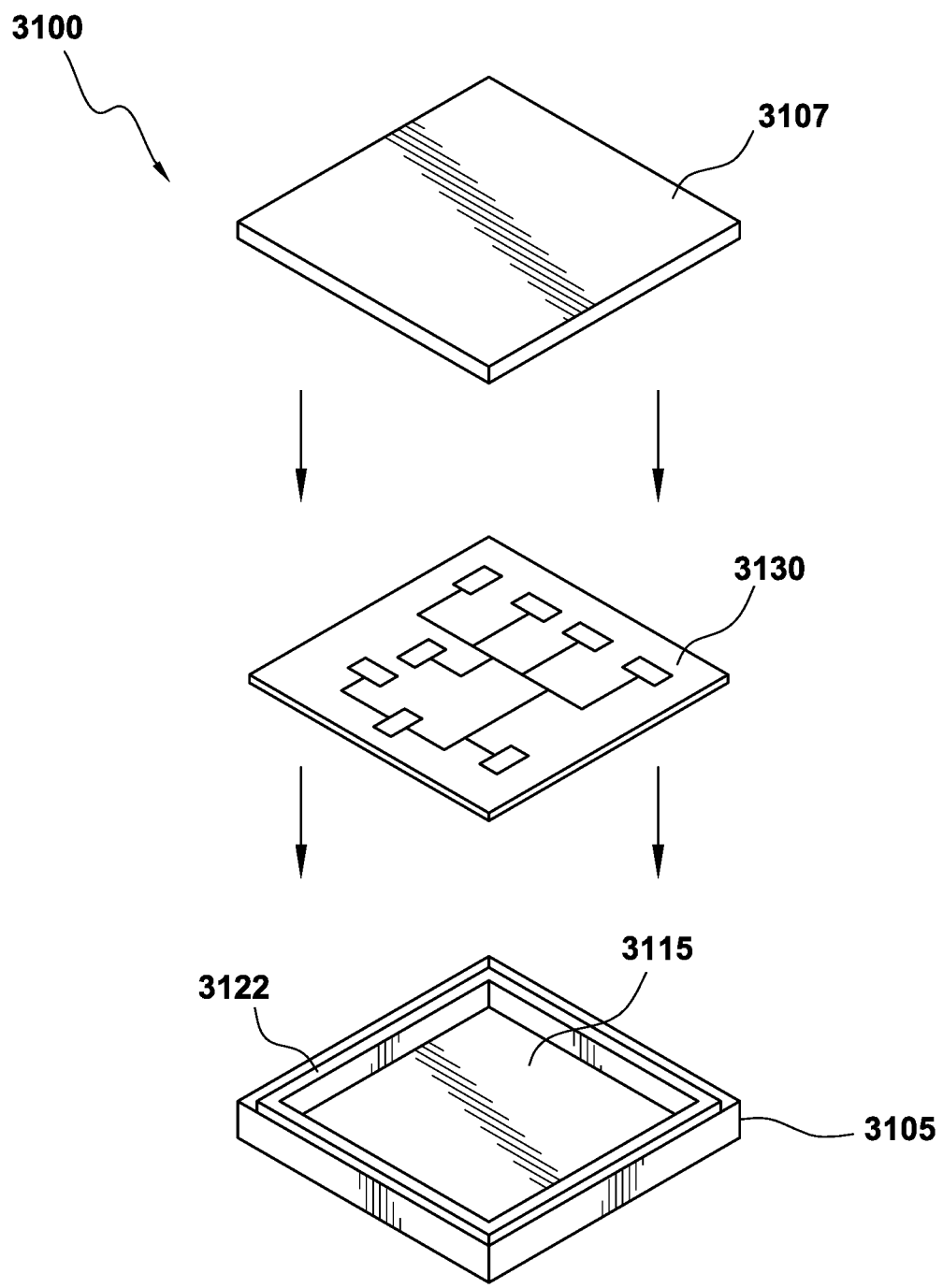
Figure 31D:
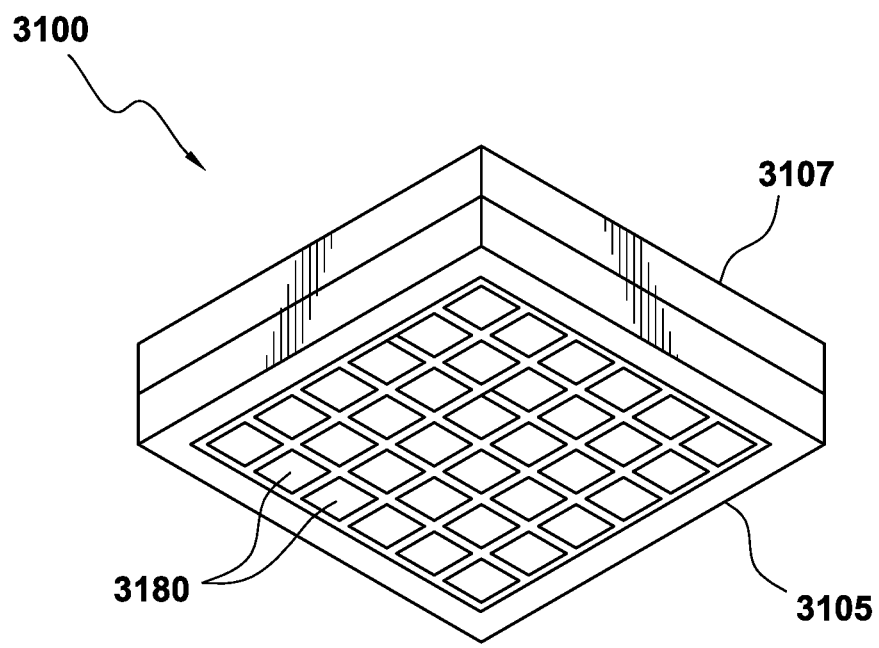

In the illustrative embodiment, sensor device 3100 is assembled by fitting waterproof layer 3115 and support 3122 into lower portion 3105 of the housing, as illustrated in FIGS. 30A and 30C. Sensor component 3130 is then placed above support 3122, and upper portion 3107 is fitted over lower portion 3105, as illustrated in FIGS. 31C and 31D. Upper portion 3107 and lower portion 3105 may form a seal when fitted together. FIG. 31D shows sensor device 3100 in a fully assembled state. Lower portion 3105 and holes 3180 is visible in FIG. 31D.

Figure 32A:
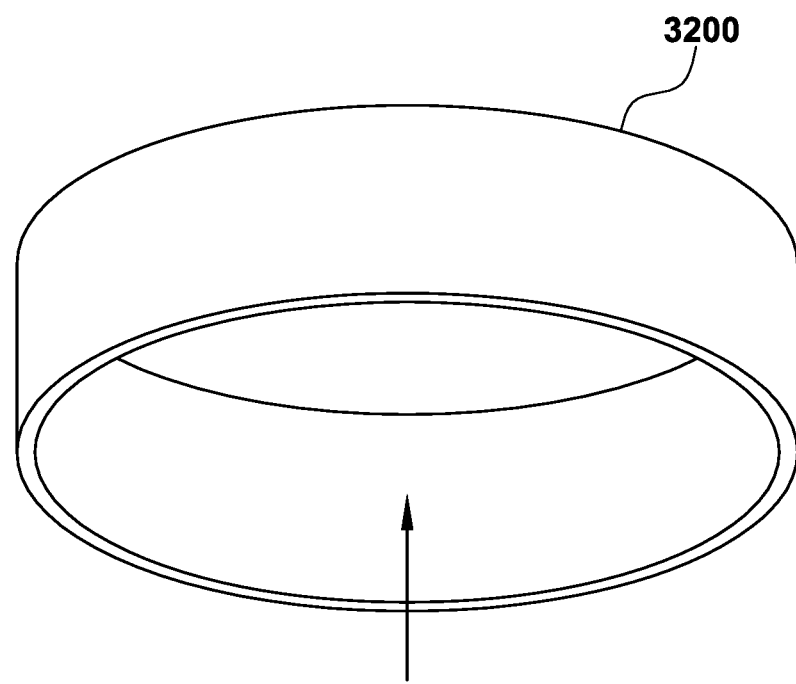
FIG. 32A shows a cap adapted to fit on a standard concrete test cylinder and a sensor device in accordance with an embodiment.
Figure 32B:
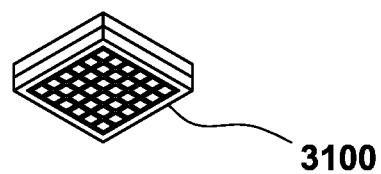
FIG. 32B shows a cap with a sensor device on a standard concrete test cylinder in accordance with an embodiment.
Figure 32B:
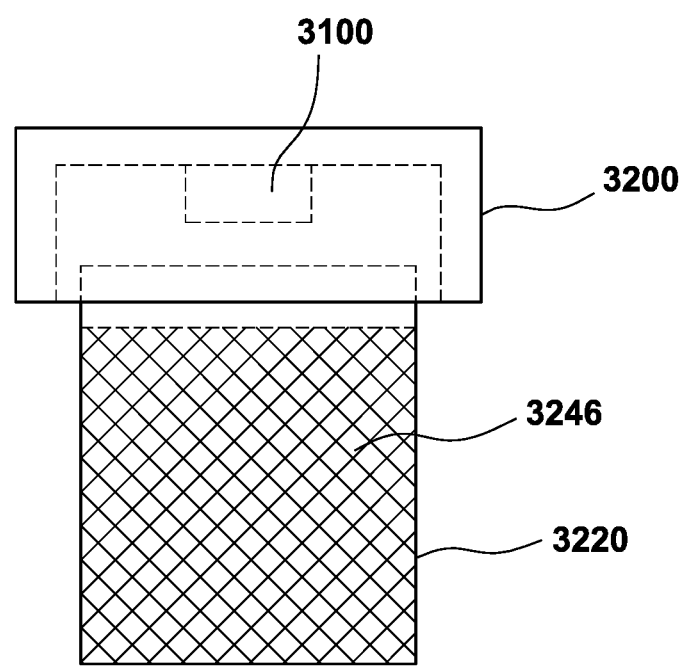

In one embodiment, sensor device 3100 may be attached to an internal surface of a cap adapted to be placed onto a standard test cylinder. FIG. 32A shows a cap and a sensor device in accordance with an embodiment. Cap 3200 is adapted to fit onto the top of a standard concrete test cylinder. Sensor 3100 is attached to an internal surface of cap 3200. Cap 3200 is then placed onto a test cylinder that contains concrete. FIG. 32B shows a cap and a test cylinder in accordance with an embodiment. Sensor device 3100 is attached to the internal surface of the cap 3200. Cap 3200 is fitted onto a test cylinder 3220, which holds a specimen of a concrete mixture 3246. As concrete mixture 3246 dries, sensor device 3100 obtains measurements relating to one or more characteristics of the concrete. For example, sensor device 3100 may obtain data relating to humidity, temperature, etc. Measurement data may be transmitted wirelessly by the sensor device.

Figure 33A:
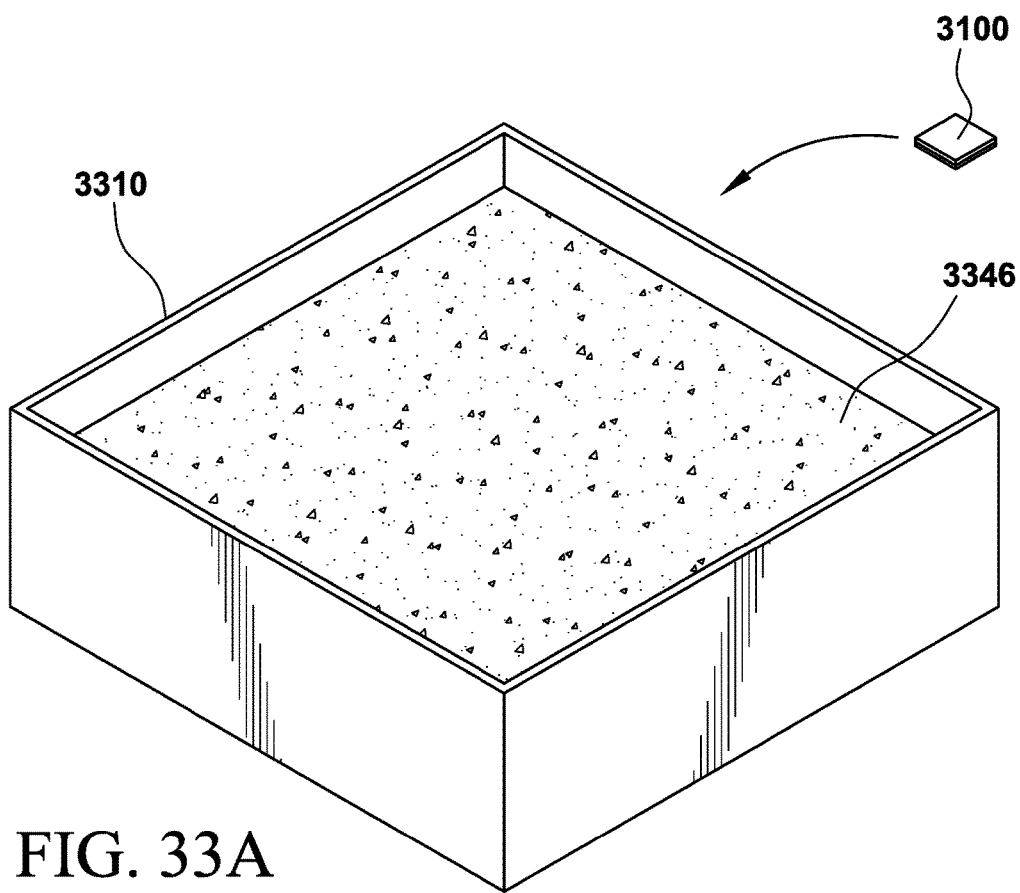
FIG. 33A shows a form containing a concrete mixture and a sensor device in accordance with an embodiment.
Figure 33B:
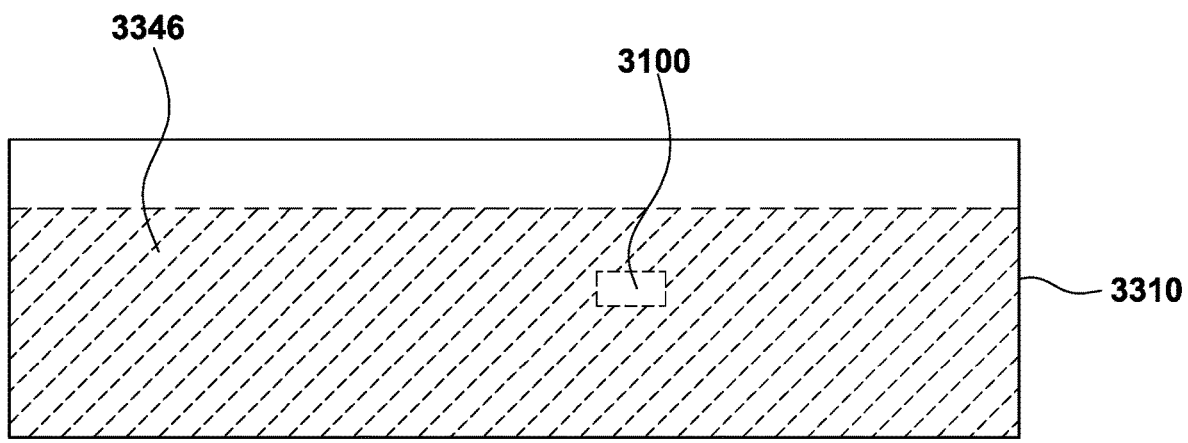
FIG. 33B shows the sensor of FIG. 33A embedded in the concrete mixture within the form of FIG. 33A.

In another embodiment, sensor device 3100 may be inserted into a concrete mixture. FIG. 33A shows a form holding a concrete mixture in accordance with an embodiment. Form 3310 holds a concrete mixture 3346. Sensor device 3100 may be dropped or inserted into concrete mixture 3346. FIG. 33B shows form 3310, concrete mixture 3346, and sensor device 3100 embedded in the concrete mixture in accordance with an embodiment. Sensor device 3100 may obtains measurements relating to one or more characteristics of concrete mixture 3346. Measurement data may be transmitted wirelessly by the sensor device.

In one embodiment, components of a sensor device (such as any of those described herein) may be formed of a thermosetting resin or a thermoplastic.

In one embodiment, a sensor device (such as any of those described herein) may have a housing with a square or rectangular shape, with a first side having a length between about 1.5 inch and about 2.0 inches, a second side having a length between about 1.5 inch and about 2.0 inches, and a thickness between about one-eight inch and one-half inch. In a preferred embodiment, a sensor device has a housing with a square shape with sides having a length of about one and three-fourths (1.75) inches, and a thickness of about three-sixteenth (3/16) inches.

It has been observed that when a sensor device with a transmitter (e.g., antenna) is embedded in a concrete mixture at a depth less than about six (6) inches, the signal transmitted by the sensor device is readily detectable by a remote receiver. However, it has been observed that in some environments, and in some concrete mixtures, when a sensor device is embedded in a concrete mixture at a depth greater than about six (6) inches, the signal strength may rapidly decrease and become undetectable to a receiver outside the concrete mixture. Therefore, there is a need for devices, systems, and methods that enable a sensor device embedded in a concrete mixture at a depth of greater than six inches to be able to transmit a signal that can be detected by a receiver located outside the concrete mixture.

Figure 34A:
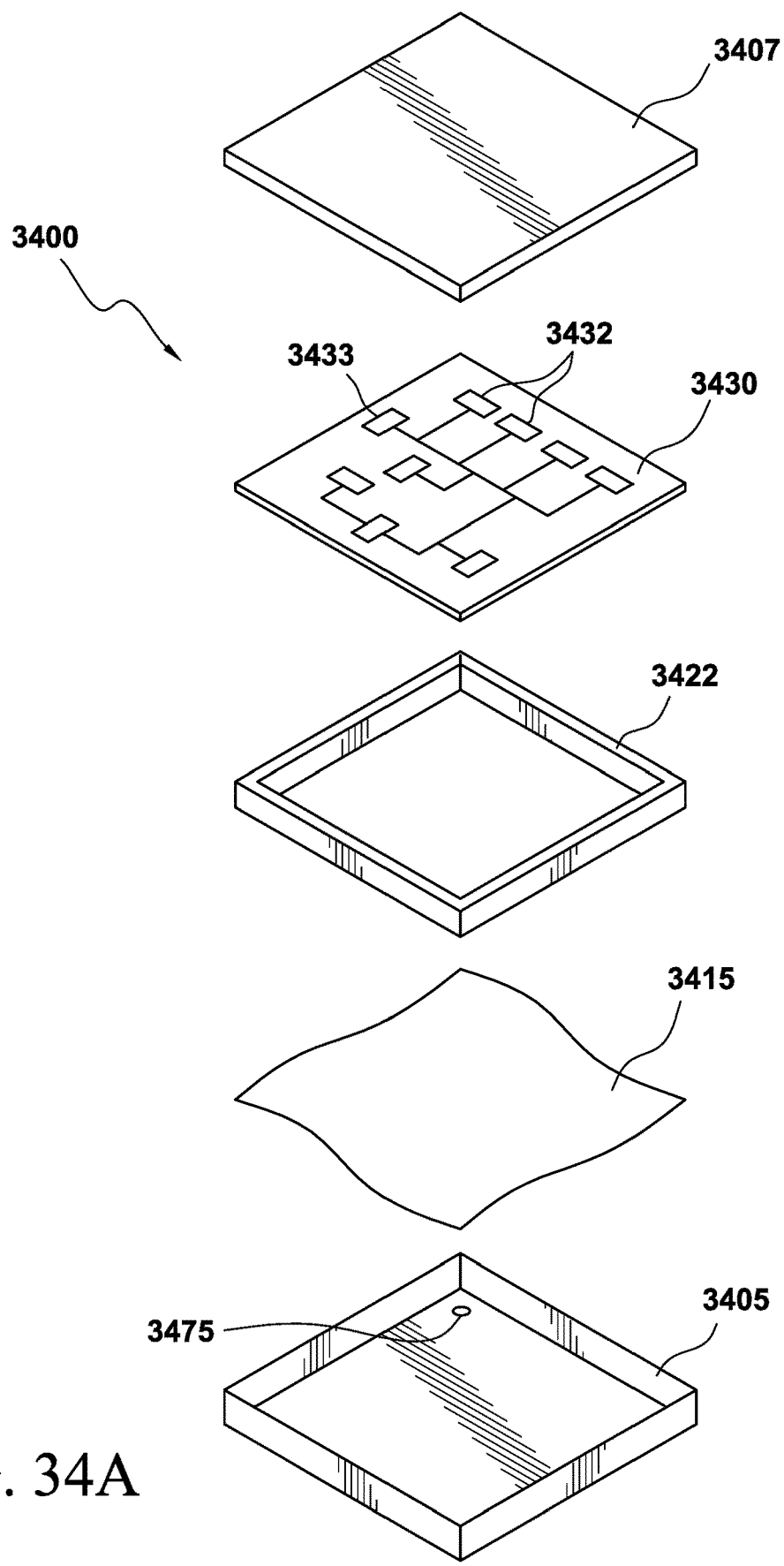
FIG. 34A shows components of a sensor device in accordance with another embodiment.

FIG. 34A shows components of a sensor device in accordance with another embodiment. A sensor device 3400 includes a housing that includes an upper portion 3407 and a lower portion 3405. Upper portion 3407 and lower portion 3405 may be formed from plastic, metal, or other material. Sensor device 3400 also includes a waterproof layer 3415, a support 3422, and a sensor component 3430.

Upper portion 3407 of housing does not include any holes. Therefore, upper portion 3407 of the housing does not allow humidity to pass through from the exterior of sensor device 3400 to the interior of the sensor device.

Lower portion 3405 includes a single hole 3475 that allows humidity (water vapor) to pass into the interior of sensor device 3400 but does not allow water, concrete, or other liquids to enter. For example, hole 3475 may be a hole having a diameter of between about 1.0 millimeters and 3.0 millimeters, preferably about 2.0 millimeters. Other diameters may be used.

Sensor component 3430 includes one or more sensors 3432 adapted to measure one or more characteristics of a surrounding material (such as concrete, water, etc.) Sensor component 3430 may be, for example, a printed circuit board (PCB) containing circuit components such as resistors, capacitors, amplifiers, etc., and/or one or more sensors adapted to obtain measurements relating to one or more characteristics such as temperature, humidity, salinity, conductivity, motion, etc. Sensor component 3430 may also include a processor. Sensor component 3430 includes an antenna 3433 adapted to transmit signals, for example, in the form of electromagnetic radiation having a selected frequency. Sensor component 3430 may also include a receiver and/or a transceiver. For example, antenna 3433 may also be adapted to function as a receiver. Sensor component 3430 may also include a battery. Alternatively, a battery or other power source may be disposed elsewhere in sensor device 3400.

Waterproof layer 3415 is made of a waterproof, breathable material that allows humidity (water vapor) to pass through the layer but does not allow liquid or concrete to pass through. For example, waterproof layer 3415 may be made waterproof, breathable fabric membrane such as Gore-Tex or other similar material.

Support 3422 is disposed between sensor component 3430 and waterproof layer 3415. Support 3422 separates waterproof layer 3415 from sensor component 3430 and thereby protects the sensors (and other electronics) of sensor component 3430 from water, liquids, concrete, etc. that may be proximate waterproof layer 3415. Thus support 3422 may maintain a predetermined distance between waterproof layer 3415 and sensor component 3430.

Figure 34B:
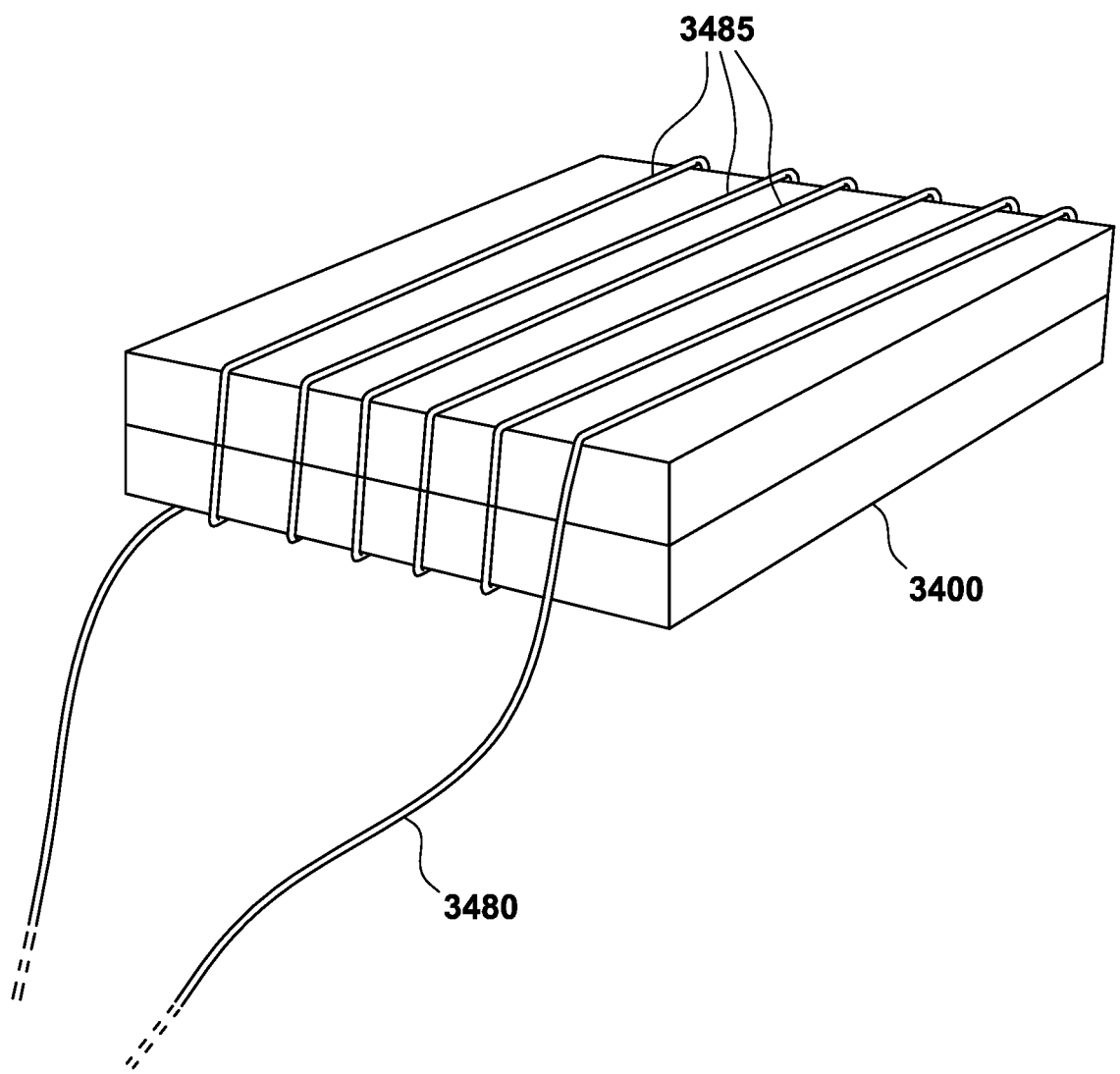
FIG. 34B shows a sensor device and a wire wound around the device, forming a plurality of loops, in accordance with an embodiment.

In accordance with an embodiment, a conductive wire is wound around sensor device 3400 to form coil having a plurality of loops. FIG. 34B shows sensor device 3400 and a wire 3480 wound around the device, forming a plurality of loops 3485, in accordance with an embodiment. Wire 3480 may be formed of any conductive material, such as metal. Wire 3480 may be insulated by a nonconductive material. In another embodiment, wire 3480 is not insulated. In one embodiment, wire 3480 is wound around the sensor device to form at least five (5) loops.

When the antenna 3433 within sensor device 3400 transmits a signal by generating electromagnetic radiation, loops 3485 function as an induction coil, and a current is generated in wire 3480 (due to electromagnetic induction). In particular, when antenna 3433 (within sensor device 3400) transmits a first signal in the form of electromagnetic radiation, an electrical current related to the first signal is generated within wire 3480. Wire 3480 may therefore serve as an antenna to transmit communication signals from sensor device 3400.

Figure 34C:
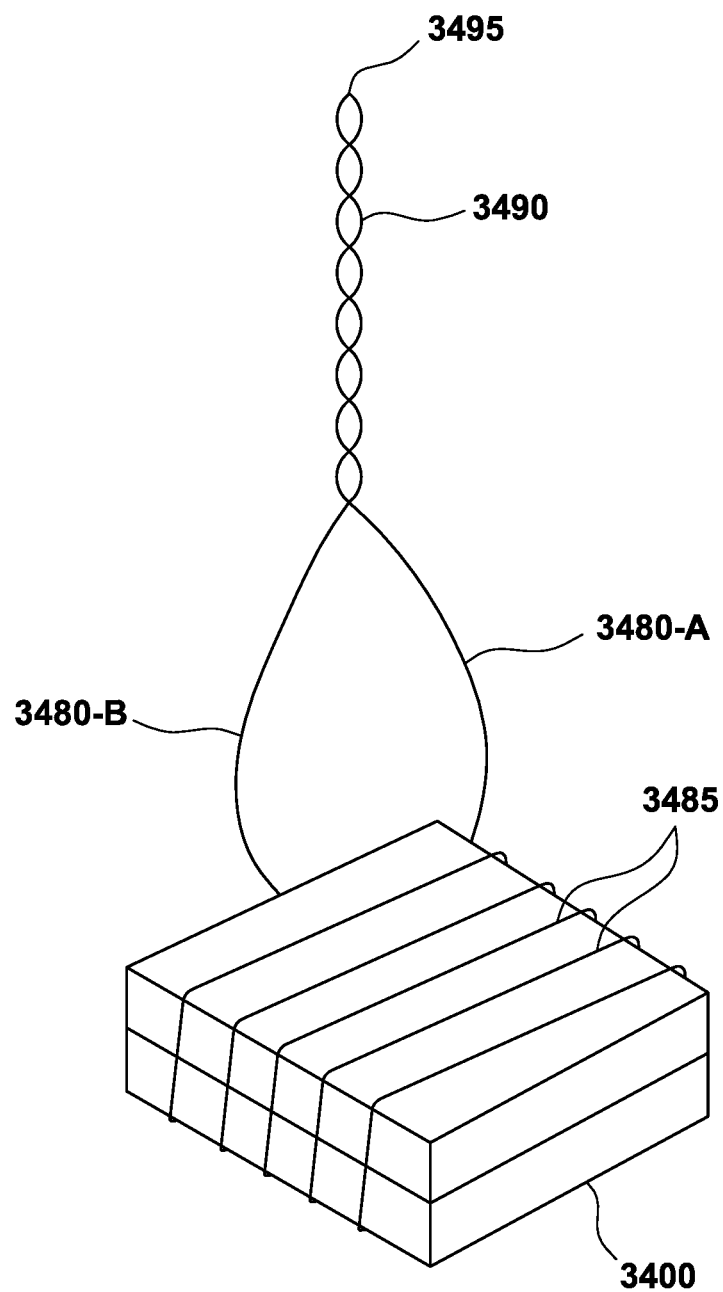
FIG. 34C shows sensor device and a coil having plurality of loops in accordance with an embodiment.

In accordance with an embodiment, the ends of wire 3480 are twisted together and connected to form a circuit. The twisted wire is used as an antenna to boost and/or transmit the signal generated by the antenna 3433 in sensor 3400. FIG. 34C shows sensor device 3400 and a coil having a plurality of loops 3485 in accordance with an embodiment. Two ends 3480-A and 3480-B of wire 3480 are twisted together to form a twisted wire 3490. The ends if the wire are connected at connection 3495, forming a circuit.

Figure 35:
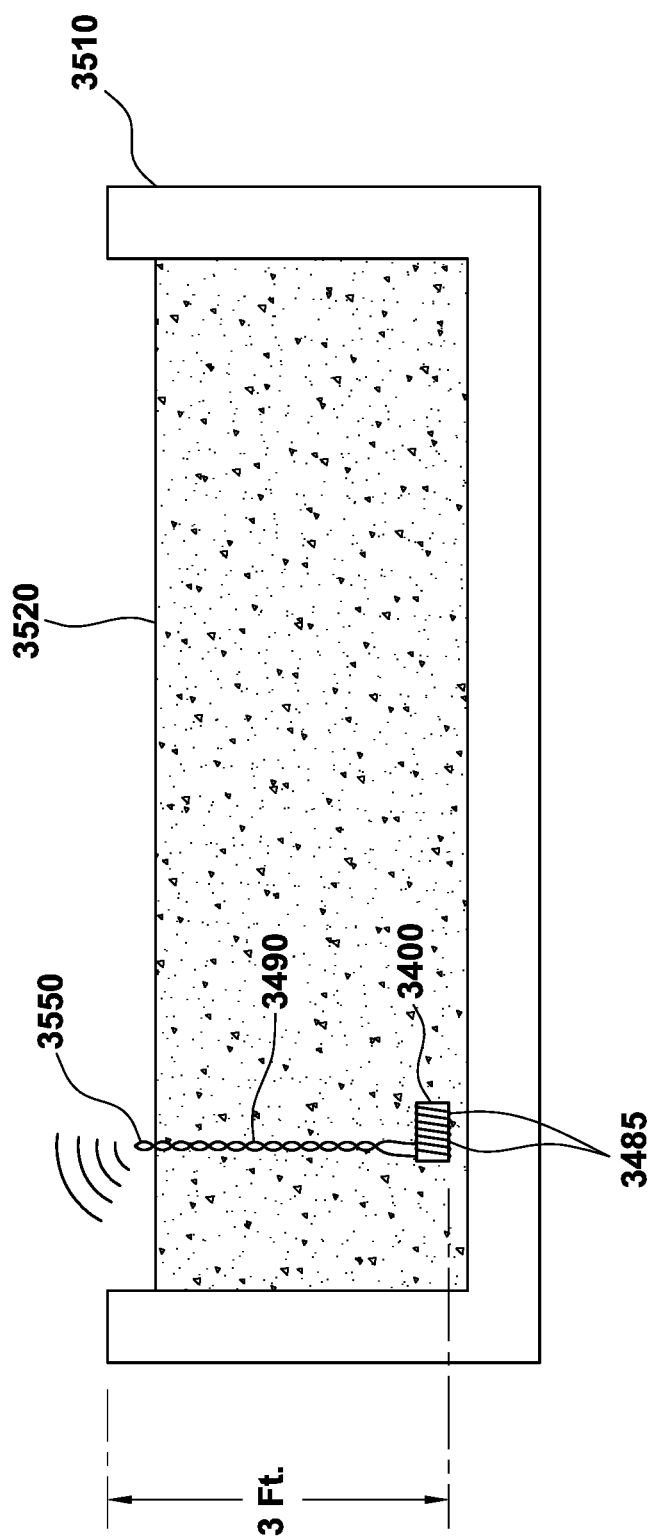
FIG. 35 shows a form containing a concrete mixture in accordance with an embodiment.

FIG. 35 shows a form containing a concrete mixture in accordance with an embodiment. Concrete mixture 3520 has a depth greater than three (3) feet. Sensor device 3400, with coil loops 3485 is embedded in concrete mixture 3520 at a depth of three (3) feet. Twisted wire 3490 is positioned so that it extends from the sensor device to the surface of concrete mixture 3520. A portion 3550 of twisted wire 3490 projects above the surface of the concrete mixture and is exposed to the surrounding environment.

In accordance with an embodiment, sensor device 3400 obtains measurements of selected characteristics of concrete mixture 3520 (such as temperature, humidity, etc.) and transmits a first electromagnetic signal representing the measurement data, via antenna 3433 (within sensor device 3400). Coil loops 3485 function as an inductive coil and generate an electrical current related to the first signal. The twisted wire 3490 operates as an antenna and transmits a second electromagnetic signal based on the first signal; the second signal may be received by a remote receiver and provided to a processor for storage and/or analysis.

It has also been observed that a sensor device with an external wire coil and antenna, such as that shown in FIG. 34C may be used to measure the purity level of water and other liquids. For example, in one embodiment, a sensor device includes a wire coil and antenna formed from a metal wire with no insulation. The sensor device is placed in a body of water (or other liquid) and the twisted wire antenna is positioned so that a portion of the antenna extends above the surface of the water. The sensor device measures one or more characteristics of the water (or other liquid) and transmits the measurement data via an antenna within the sensor device. A current is induced in the metal wire coil and an electromagnetic signal related to the current is transmitted via the portion of the twisted wire antenna that is exposed above the surface of the water. It has been observed that the strength of the signal transmitted via the twisted wire antenna varies depending on the level of impurities in the water. In particular, it has been observed that a signal having a higher strength is produced when the level of impurities in the water is low, and that a signal having lower strength (or no signal at all) is transmitted when the level of impurities in the water is high.

Figure 36:
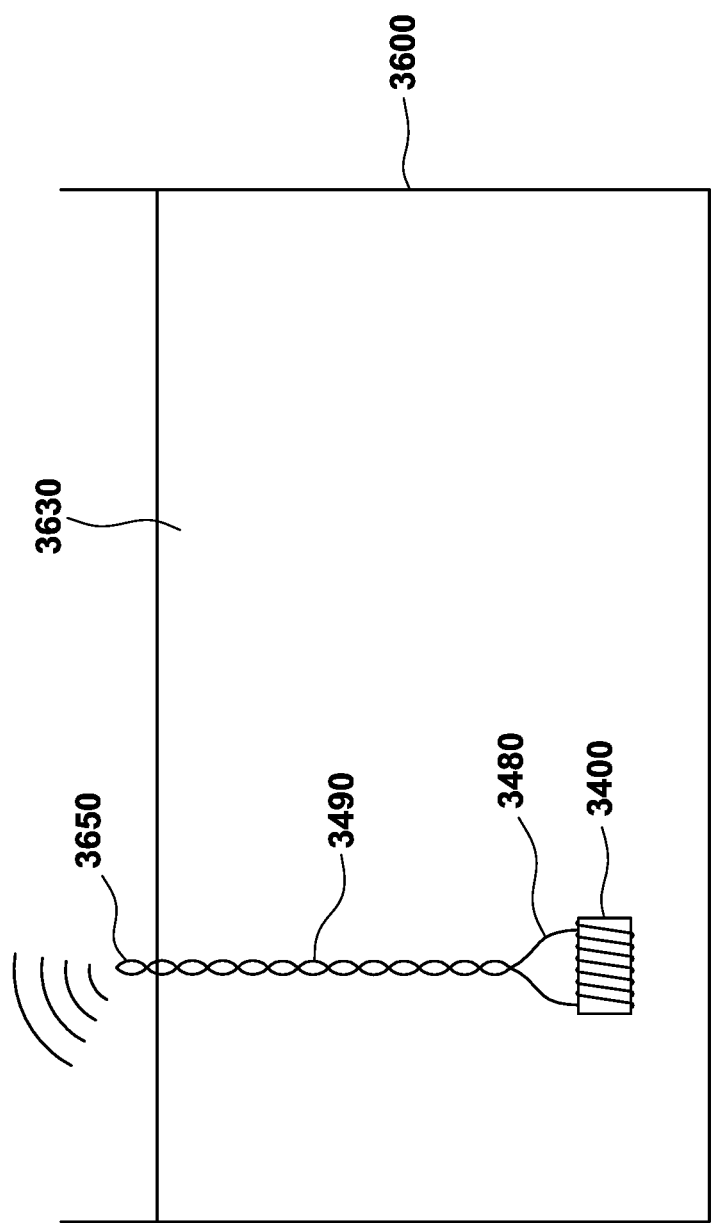
FIG. 36 shows a container of water holding a body of water in accordance with an embodiment.

FIG. 36 shows a container of water 3600 holding water 3630 in accordance with an embodiment. In other embodiments, other types of liquids may be used. Sensor device 3400 is positioned in the water 3630. A wire 3480 is wrapped around sensor device 3400 to form a coil having a plurality of loops. The ends of wire 3480 are twisted to form an antenna; a portion 3650 of antenna 3490 extends above the surface of water 3630. Wire 3480 is a metal wire with no insulation. Other conductive materials may be used. As sensor device 3400 transmits measurement data, an electric current is generated in the wire coil surrounding sensor device. The electric current is related to the signal produced by the sensor device, and produces an electromagnetic signal which is transmitted via antenna 3490 to convey the measurement data. Specifically, portion 3650 of antenna 3490 transmits the signal.

In one embodiment, the strength of the signal produced by antenna 3490 is measured and used to determine a level of impurities in water 3630. For example, if little or no signal is produced by antenna 3490, it may be determined that the level of impurities is high. If the strength of the signal is high, it may be determined that the level of impurities in water 3630 is low.

Thus, in one embodiment, a method is provided. A sensor with an external wire coil and antenna is submerged in a body of water. A portion of the wire antenna is exposed above the surface of the water. The sensor device generates a first electromagnetic signal. A current is generated in the wire coil due to electromagnetic induction. A second electromagnetic signal is transmitted by the wire antenna. The second electromagnetic signal generated is transmitted to a processor. The processor may analyze the strength of the second signal and determine a level of impurities in the water based on the strength of the second signal.

In accordance with another embodiment, a sensor device includes a housing and at least one wire extending from the housing. The sensor device is embedded in a concrete mixture. The sensor device obtains measurements of one or more characteristics of the concrete mixture, such as temperature, humidity, etc.

The at least one wire functions as an antenna. A signal containing the information relating to the measurements of the one or more characteristics is transmitted via the wire.

In various embodiments, a sensor may have one wire, two wires, or more than two wires extending from the housing and functioning as antennas.

In one embodiment, the portion of the wire that is external to the housing has a selected length. The signal containing the measurement information has a wavelength related to the length of the wire. Advantageously, a relationship between the length of the wire and the wavelength of the signal is selected to cause resonance in the wire and thereby boost the strength of the signal.

Advantageously, the relationship between the wire length and signal wavelength of a sensor embedded in a concrete mixture may increase the strength of a signal received from the sensor, for example, by a Wifi router located at a selected distance from the concrete mixture. As a result, the WiFi router may receive a higher quality signal and/or be positioned at a larger distance from the concrete mixture.

Various relationships between the wire length and signal wavelength may be used. For example, in accordance with an embodiment, the length of the wire external to the housing is one-half the wavelength of the signal transmitted via the wire. In another embodiment, the length of the wire is equal to one-fourth the wavelength of the signal. In another embodiment, the length of the wire is equal to the wavelength of the signal. In another embodiment, the length of the wire is twice the wavelength of the signal. In other embodiments, the length of the wire is equal to a selected multiple of the wavelength. Other relationships may be used.

Figure 37:
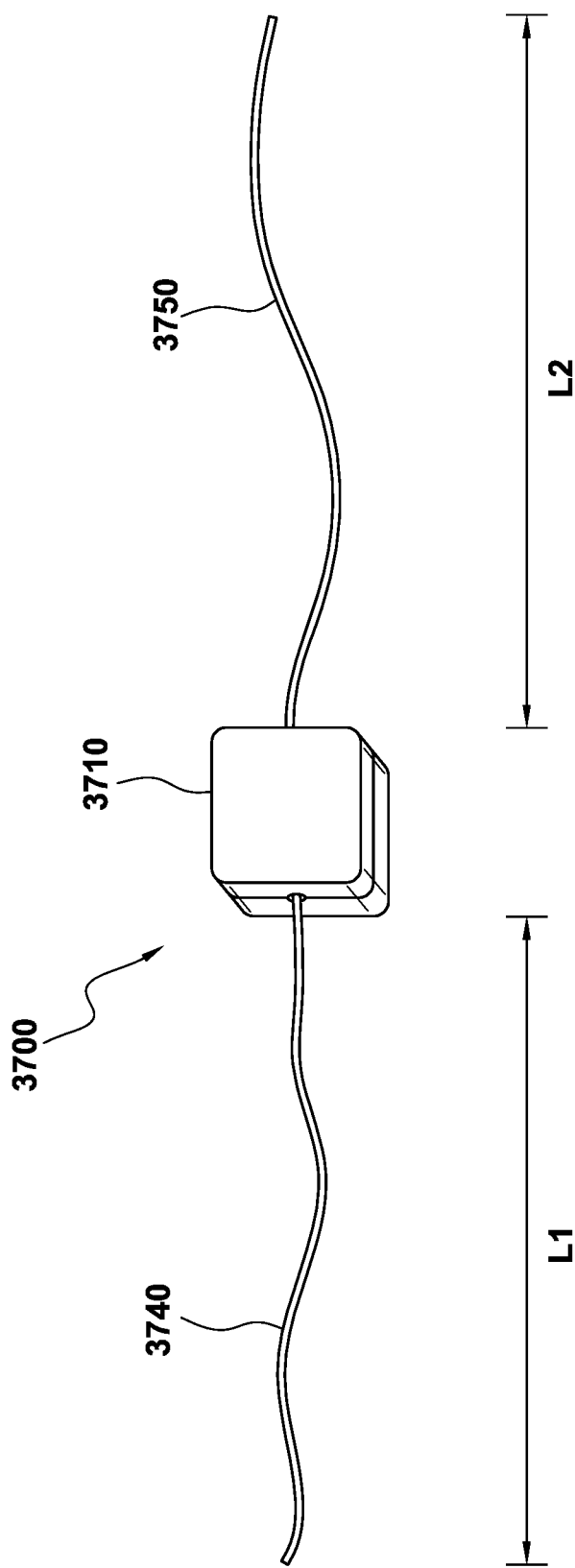
FIG. 37 shows a sensor device in accordance with an embodiment.

FIG. 37 shows a sensor device in accordance with an embodiment. Sensor 3700 includes a housing 3710, a first wire 3740 extending from the housing, and a second wire 3750 extending from the housing. The wires may be insulated, or may not have insulation. Sensor device 3700 includes one or more sensors adapted to obtain measurements relating to a concrete mixture. The length of the portion of first wire 3740 that is external to housing 3710 is L1. The length of the portion of second wire 3750 that is external to housing 3710 is L2.

Figure 38:
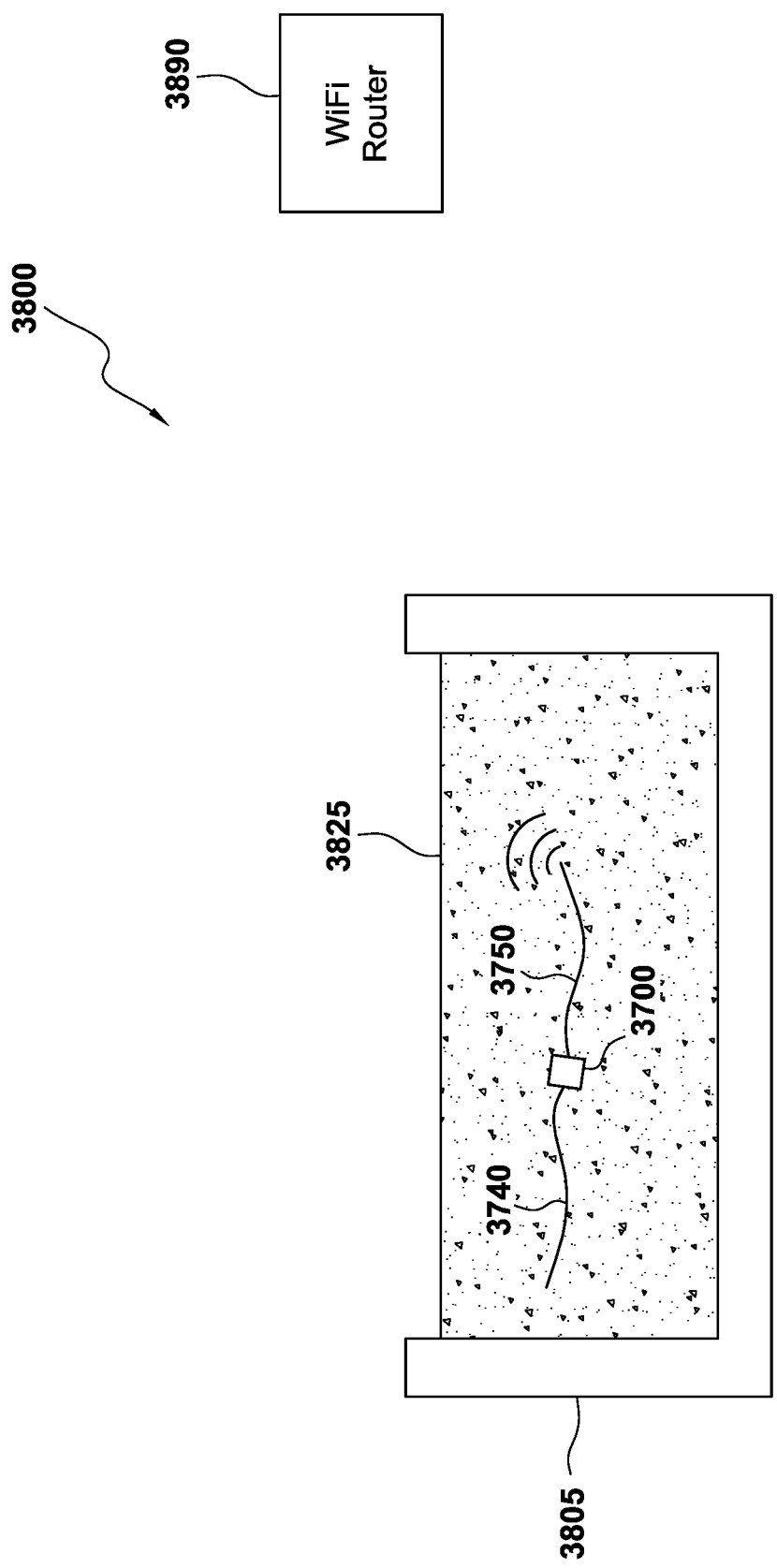
FIG. 38 shows a communication system in accordance with an embodiment.

FIG. 38 shows a communication system in accordance with an embodiment. Communication system 3800 includes sensor device 3700 and a WiFi router 3890. A form 3805 contains a concrete mixture 3825. Sensor device 3700 is embedded in concrete mixture 3825. Wires 3740 and 3750 are also embedded in concrete mixture 3825. Wires 3740 and 3750 transmit signals relating to measurements obtained by sensor device 3700. WiFi router 3890 is located at a selected distance from sensor device 3700. WiFi router 3890 receives signals from sensor device 3700 and transmits them, for example, to a second device, or to a network.

Figure 39:
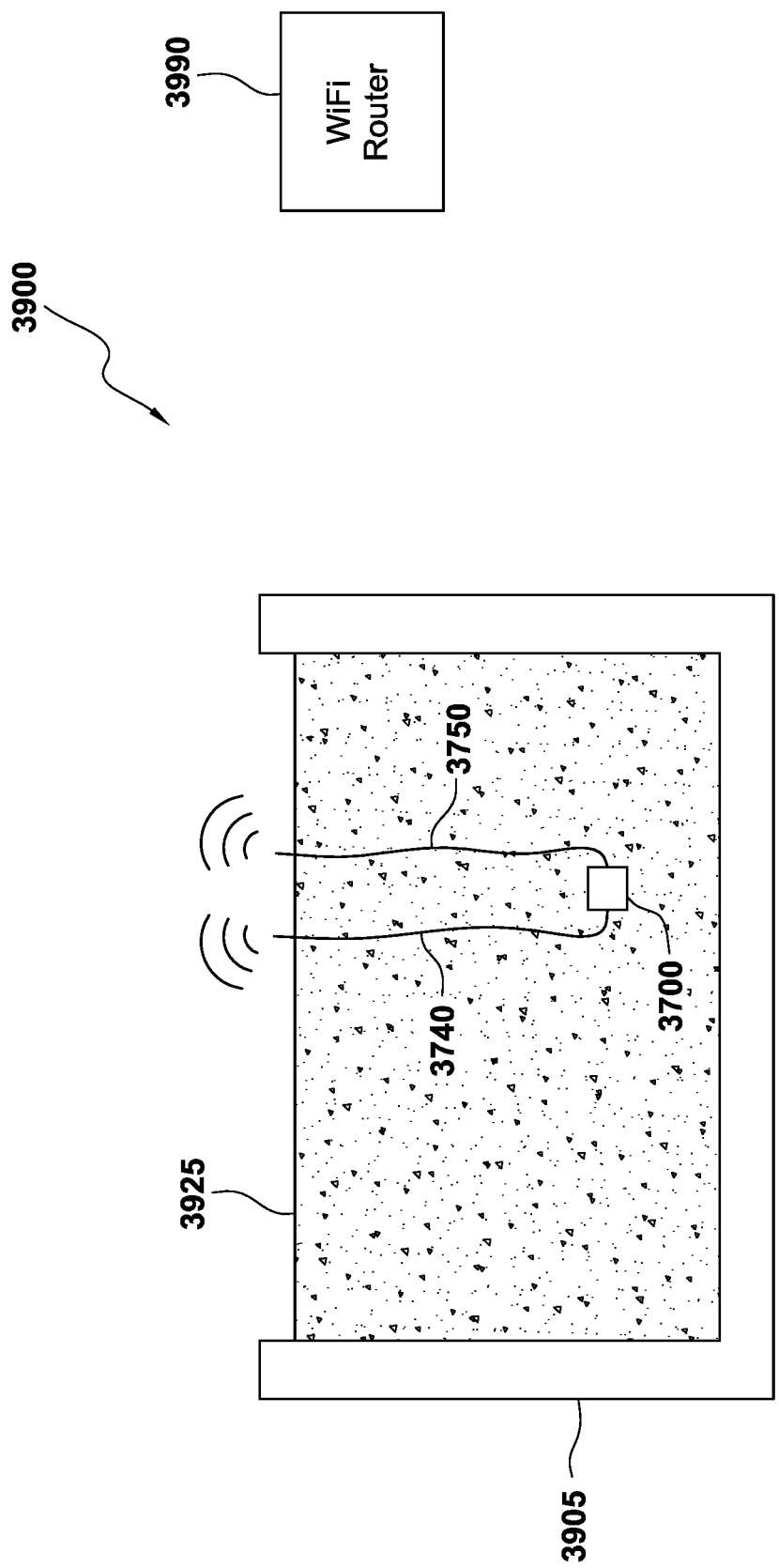
FIG. 39 shows a communication system in accordance with an embodiment.

FIG. 39 shows a communication system in accordance with another embodiment. Communication system 3900 includes sensor device 3700 and a WiFi router 3990. A form 3905 contains a concrete mixture 3925. Sensor device 3700 is embedded in concrete mixture 3925. Wires 3740 and 3750 are also embedded in concrete mixture 3925. Wires 3740 and 3750 are arranged so that they extend from sensor device 3700 up to and above the surface of concrete mixture 3925. Wires 3740 and 3750 transmit signals relating to measurements obtained by sensor device 3700. WiFi router 3990 is located at a selected distance from sensor device 3700. WiFi router 3990 receives signals from sensor device 3700 and transmits them, for example, to a second device, or to a network.

Figure 40:
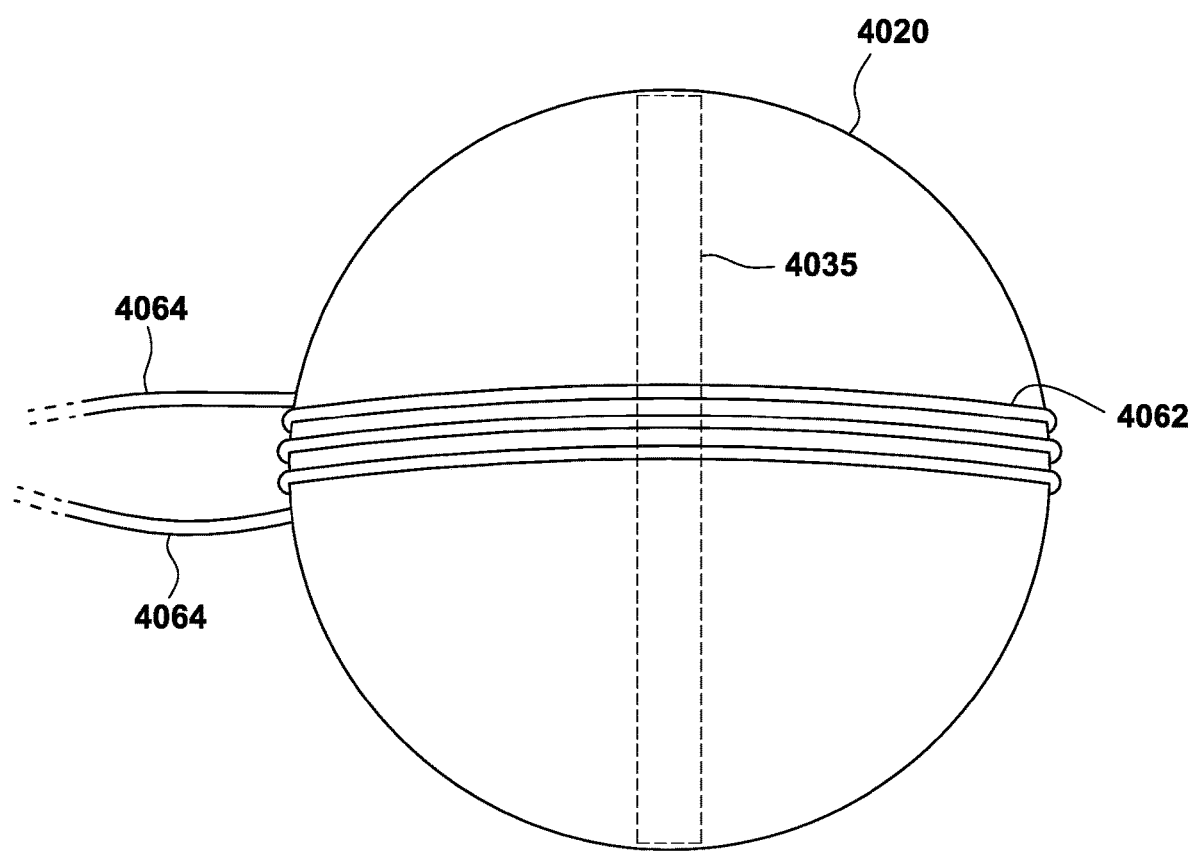
FIG. 40 shows a sensor device in accordance with another embodiment.

FIG. 40 shows a sensor device in accordance with another embodiment. The sensor device includes a shell 4020 that may comprise plastic, for example, or another material. Shell 4020 may include two or more portions and may be sealed, for example. A printed circuit board (PCB) 4035 that holds one or more sensors (e.g., humidity, temperature sensors, etc.) is disposed inside shell 4020. PCB 4035 also includes an antenna adapted to transmit a signal containing measurement information. A wire is wound around shell 4020 to form a plurality of coils 4062. The wire is formed of a conductive material. First and second ends 4064 of the wire extend from shell 4020. In one embodiment, the length of the wire wound around shell 4020 is related to the wavelength of a signal transmitted by PCB 4035 (e.g., one-half the wavelength of the signal, one-fourth the wavelength of the signal, etc.).

Figure 41:
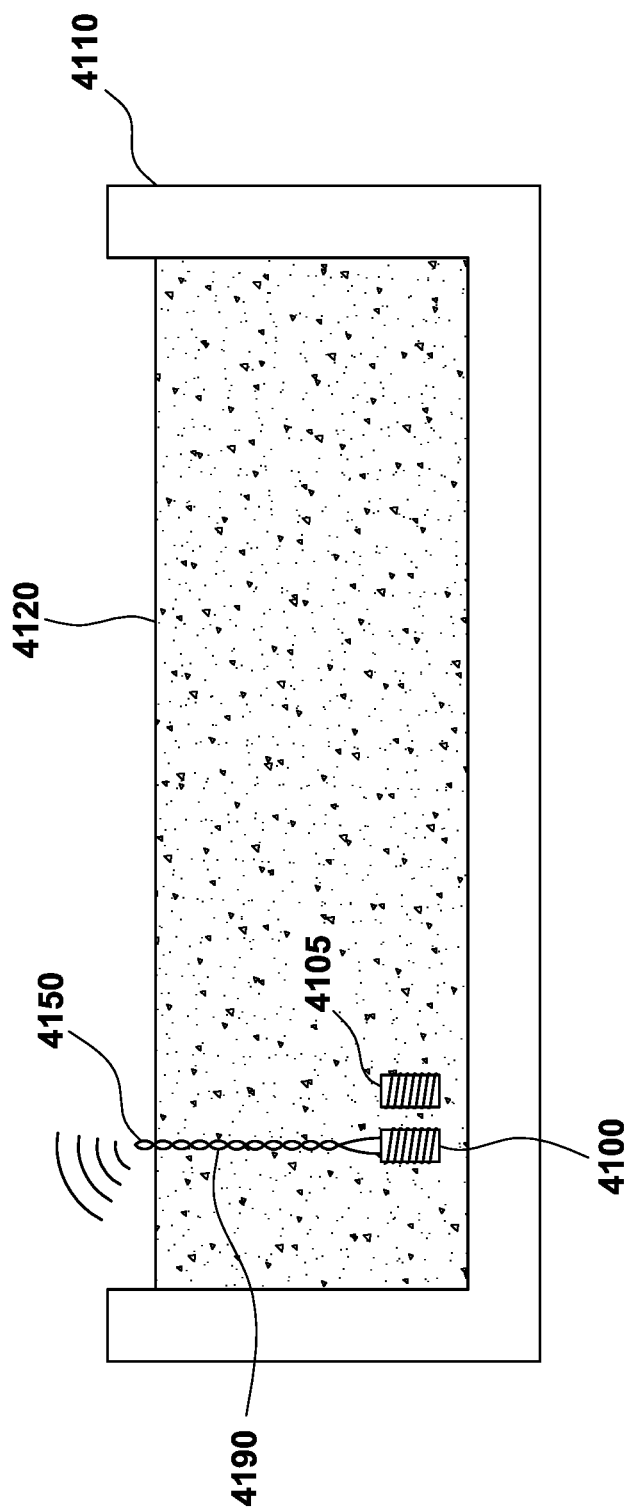
FIG. 41 shows a concrete mixture containing several sensor devices in accordance with an embodiment.

FIG. 41 shows a concrete mixture containing several sensor devices in accordance with an embodiment. Form 4110 includes a concrete mixture 4120. A first sensor device 4100 with a plurality of coils and an antenna 4190 is embedded at a selected depth in the concrete mixture. A portion 4150 of antenna 4190 extends above the surface of the concrete mixture. A second sensor device 4105 has a second plurality of coils but does not have a wire extending above the surface of the concrete. Second sensor device 4105 is embedded in the concrete proximate to or adjacent to first sensor device 4100. For example, the two sensors may touch each other. Alternatively, the two sensors may be separated by a small distance (e.g., less than one inch). The coils of first sensor device 4100 respond to first signals generated by a printed circuit board inside sensor device 4100; the first signal (or a related signal) is transmitted via antenna 4190 to a remote device. The coils of sensor device 4100 also respond to second signals generated by a printed circuit board inside second sensor device 4105, and the antenna 4190 transmits the second signals (or a related signal) via antenna 4190. For example, antenna 4190 may transmit the signals to a WiFi station.

Figure 42:
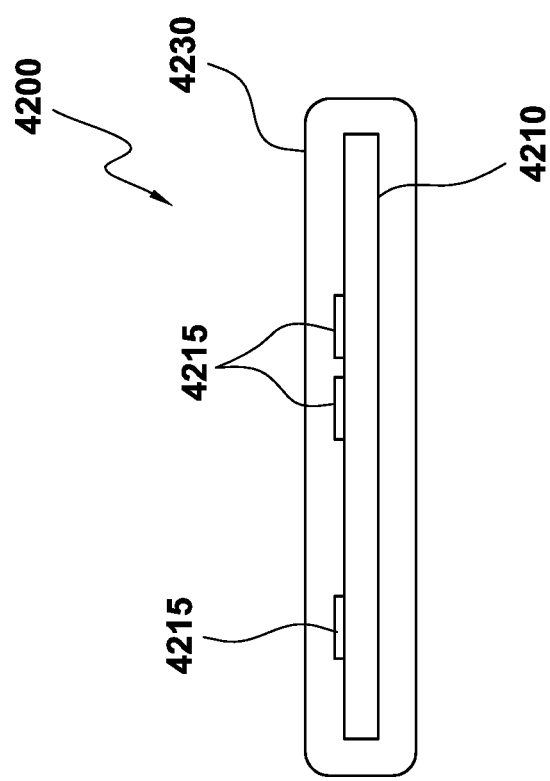
FIG. 42 shows a cross-section of a sensor device in accordance with an embodiment.

In accordance with another embodiment, a sensor device includes a printed circuit board with sensors coated entirely or partially with a protective material. FIG. 42 shows a cross-section of a sensor device in accordance with an embodiment. Sensor device 4200 includes a printed circuit board (PCB) 4210 that includes a plurality of sensors 4215. Sensors 4215 may include, for example, temperature sensors, humidity sensors, salinity sensors, conductivity sensors, motion sensors, pH sensors, etc. All or a portion of the surface of PCB 4210 is covered by a protective coating material 4230, which may be rubber or plastic, for example. The protective coating material may be waterproof, for example. The coating material protects the sensors on PCB 4210 from water, for example.

In one example, sensor device 4200 may be formed by applying a liquid rubber material to the surface of PCB 4210. In another embodiment, a liquid plastic material may be applied.

Figure 43:
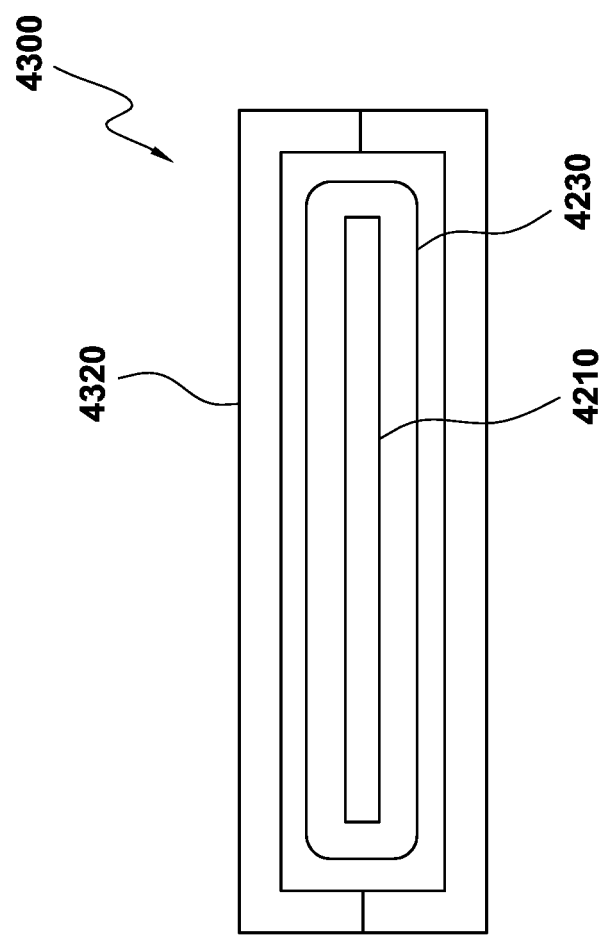
FIG. 43 shows a sensor device in accordance with another embodiment.

FIG. 43 shows a sensor device in accordance with another embodiment. Sensor device 4300 includes PCB 4210, which is covered by material layer 4230 and encased in a case 4320. Case 4320 may be formed of plastic, for example.

Figure 44:
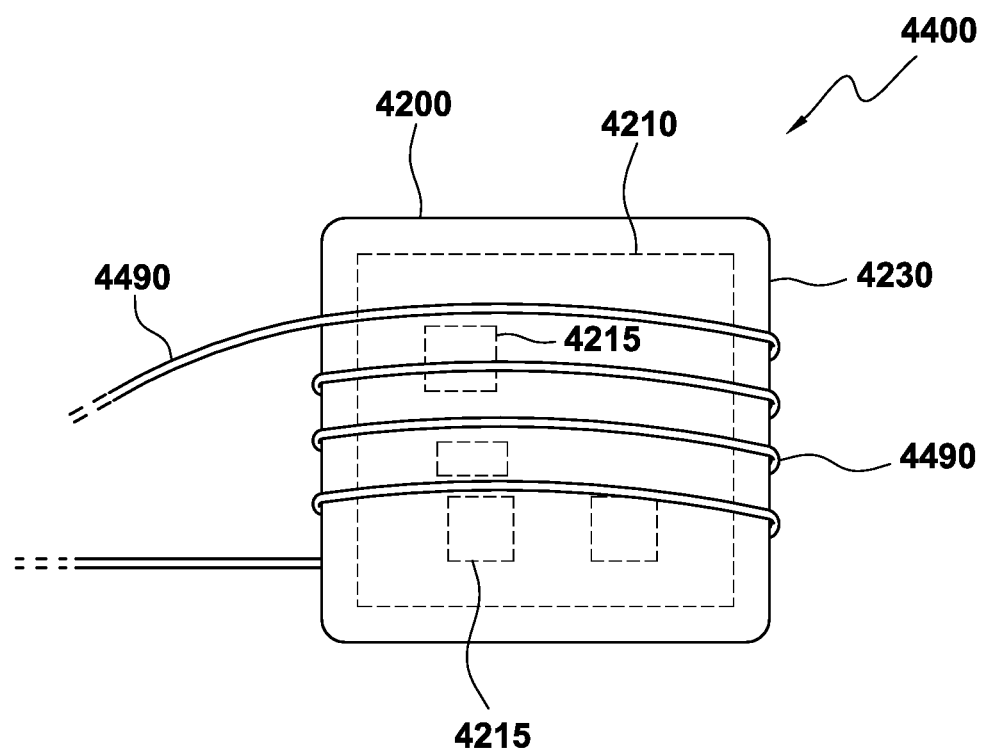
FIG. 44 shows a sensor device in accordance with another embodiment.

FIG. 44 shows a sensor device in accordance with another embodiment. Sensor device 4400 includes PCB 4210 (with sensors 4215), which is covered by material layer 4230. Sensor device 4400 also includes a wire 4490 wound around PCB 4210 and material layer 4230, forming a plurality of coils. Wire 4490 is formed of a conductive material. First and second ends of the wire may be used as an antenna, for example.

As mentioned above, in various embodiments, predictions of maturity, strength, and other characteristics may be generated based on measurement data received from one or more sensing devices. Relationships between curing temperature of a concrete mixture and the maturity of the concrete mixture, and between curing temperature of a concrete mixture and the strength of the concrete mixture are well-known. For example, relationships between curing temperature of a concrete mixture and the maturity of the concrete mixture, and between curing temperature of a concrete mixture and the strength of the concrete mixture are discussed in several standards established by ASTM International such as ASTM 1074. Additional examples of relationships between curing temperature and strength and between curing temperature and maturity are found in Burg, Ronald G., "The Influence of Casting and Curing Temperature on The Properties of Fresh and Hardened Concrete," Portland Cement Association: Research and Development Bulletin, ISBN 0-89312-143-6, Skokie, Ill., 1996.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A system comprising:
a sensor device comprising a housing, a sensor adapted to generate measurement data relating to a characteristic of a concrete mixture, and a transmitting device adapted to transmit a first signal based on the measurement data, the sensor and the transmitting device being disposed in the housing;
a conductive wire forming a coil having a plurality of loops around the housing;
wherein the coil is adapted to generate an electric current in response to the first signal;
wherein the coil is adapted to transmit a second signal based on the electric current.

2. The system of claim 1, wherein the coil includes at least five loops.

3. The system of claim 1, wherein the conductive wire comprises a metal.

4. The system of claim 3, wherein the conductive wire comprises an insulated metal wire.

5. The system of claim 1, wherein the characteristic is one of: temperature, sonic signal strength, acceleration, motion, pH, inductance, impedance, resistivity, pressure, conductivity, salinity, humidity, and elevation.

6. The system of claim 1, wherein the sensor device comprises a printed circuit board having a plurality of sensors.

7. The system of claim 6, wherein the plurality of sensors include one of: a temperature sensor, a sonic sensor, an acceleration sensor, a motion sensor, a pH sensor, an inductance sensor, an impedance sensor, a resistivity sensor, a pressure sensor, a conductivity sensor, a salinity sensor, a humidity sensor, and an elevation sensor.

8. The system of claim 1, wherein the sensor device is covered by a layer of a protective material.

9. A sensor device comprising:
a housing;
a sensor adapted to obtain a measurement;
a wire extending from the housing, the wire having a length, the wire adapted to function as an antenna; and
a transmitter adapted to transmit a signal via the wire, the signal having a wavelength selected based on the length of the wire.

10. The sensor device of claim 9, wherein the signal includes information relating to the measurement.

11. The sensor device of claim 9, wherein the wavelength of the signal is one of: twice the length of the wire, the length of the wire, one-half the length of the wire, and one-fourth the length of the wire.

12. A communication system comprising:
a concrete mixture;
the sensor device of claim 9, wherein the sensor device is embedded in the concrete mixture; and
a wireless router adapted to receive signals from the sensor device.

13. The communication system of claim 12, wherein the wire is entirely below a surface of the concrete mixture.

14. The communication system of claim 12, wherein the wire extends above a surface of the concrete mixture.

15. The communication system of claim 12, wherein the sensor includes one of a temperature sensor, an accelerometer, a pH sensor, an inductance sensor, an impedance or resistivity sensor, a sonic sensor, a pressure sensor, a conductivity sensor, a salinity sensor, a humidity sensor, and an elevation sensor.

16. A device comprising:
a printed circuit board comprising a first edge, a second edge, a surface located between the first and second edges, one or more sensors adapted to obtain measurement data, and a first antenna adapted to transmit a first signal based on the measurement data, the first antenna disposed between the first and second edges;
a layer of a waterproof protective material covering at least a portion of the printed circuit board; and
a conductive wire having a first portion that is wound around the first edge, the second edge, and the first antenna of the printed circuit board to form a plurality of coils, and a second portion that functions as a second antenna;
wherein:
the plurality of coils of the conductive wire responds to the first signal due to inductive coupling, thereby generating a second signal; and
the second antenna transmits the second signal.

17. The device of claim 16, wherein the device is embedded in a concrete mixture.

18. A system comprising:
a concrete mixture;
the sensor device of claim 16 embedded in the concrete mixture; and
a wireless router disposed at a selected distance from the concrete mixture.

19. The sensor device of claim 16, wherein the waterproof protective layer comprises one of rubber and plastic.

20. The sensor device of claim 16, wherein the printed circuit board comprises one of a temperature sensor, a humidity sensor, an accelerometer, a pH sensor, an inductance sensor, an impedance or resistivity sensor, a sonic sensor, a pressure sensor, a conductivity sensor, a salinity sensor, and an elevation sensor.

* * * * *